(12) United States Patent
Bolli et al.

(10) Patent No.: US 8,148,410 B2
(45) Date of Patent: Apr. 3, 2012

(54) THIOPHENE DERIVATIVES AS AGONISTS OF S1P1/EDG1

(75) Inventors: Martin Bolli, Allschwil (CH); Cyrille Lescop, Kembs (FR); Boris Mathys, Pratteln (CH); Claus Mueller, Weil am Rhein (DE); Oliver Nayler, Arlesheim (CH); Beat Steiner, Dornach (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 47 days.

(21) Appl. No.: 12/747,280

(22) PCT Filed: Dec. 9, 2008

(86) PCT No.: PCT/IB2008/055156
§ 371 (c)(1),
(2), (4) Date: Jun. 10, 2010

(87) PCT Pub. No.: WO2009/074950
PCT Pub. Date: Jun. 18, 2009

(65) Prior Publication Data
US 2010/0261702 A1    Oct. 14, 2010

(30) Foreign Application Priority Data

Dec. 10, 2007 (WO) ................ PCT/IB2007/054991

(51) Int. Cl.
*A61K 31/381* (2006.01)
*A61K 31/4245* (2006.01)
*A61K 31/41* (2006.01)
*C07D 271/06* (2006.01)
*C07D 271/10* (2006.01)
*C07D 285/16* (2006.01)
*C07D 409/04* (2006.01)

(52) U.S. Cl. ........ 514/363; 514/364; 514/444; 548/125; 548/131; 549/59; 549/60

(58) Field of Classification Search .................. 514/364, 514/363, 444; 548/125, 131; 549/59, 60
See application file for complete search history.

(56) References Cited

U.S. PATENT DOCUMENTS

| | | | |
|---|---|---|---|
| 6,090,804 | A | 7/2000 | Kimura et al. |
| 7,605,269 | B2 | 10/2009 | Bolli et al. |
| 7,723,378 | B2 | 5/2010 | Bolli et al. |
| 7,750,040 | B2 | 7/2010 | Bolli et al. |
| 2007/0043014 | A1 | 2/2007 | Doherty et al. |
| 2008/0113961 | A1 | 5/2008 | Nishi et al. |
| 2008/0194670 | A1 | 8/2008 | Bolli et al. |
| 2008/0200535 | A1 | 8/2008 | Ohmori et al. |
| 2008/0300294 | A1 | 12/2008 | Bolli et al. |
| 2009/0005421 | A1 | 1/2009 | Bolli et al. |
| 2010/0048648 | A1 | 2/2010 | Bolli et al. |
| 2010/0075946 | A1 | 3/2010 | Bolli et al. |
| 2010/0204198 | A1 | 8/2010 | Bolli et al. |
| 2010/0240717 | A1 | 9/2010 | Bolli et al. |

FOREIGN PATENT DOCUMENTS

| | | |
|---|---|---|
| DE | 1092929 | 11/1960 |
| EP | 0921123 | 6/1999 |
| EP | 1873153 | 1/2008 |
| JP | 2008120794 | 5/2008 |
| WO | WO 91/15583 | 10/1991 |
| WO | WO 99/46277 | 9/1999 |
| WO | WO 03/062248 | 7/2003 |
| WO | WO 03/062252 | 7/2003 |
| WO | WO 2004/035538 | 4/2004 |
| WO | WO 2005/032465 | 4/2005 |
| WO | WO 2005/058848 | 6/2005 |
| WO | WO/2006/047195 | 5/2006 |
| WO | WO 2006/114400 | 11/2006 |
| WO | WO 2006/115188 | 11/2006 |
| WO | WO 2006/131336 | 12/2006 |
| WO | WO 2007/001973 | 1/2007 |
| WO | WO 2007/080542 | 7/2007 |
| WO | WO 2007/085451 | 8/2007 |
| WO | WO 2008/023783 | 2/2008 |
| WO | WO 2008/029306 | 3/2008 |
| WO | WO 2008029306 A2 * | 3/2008 |
| WO | WO 2008/076356 | 6/2008 |
| WO | WO 2008/091967 | 7/2008 |
| WO | WO 2009/151529 | 12/2009 |

OTHER PUBLICATIONS

Horuk et al., The Journal of Biological Chemistry vol. 5(12), (2001), p. 4199-4204.*

Abdel-Magid, A.F., et al., "Reductive Amination of Aldehydes and Ketones with Sodium Triacetoxyborohydride. Studies on Direct and Indirect Reductive Amination Procedures", J. Org. Chem., vol. 61, pp. 3849-3862, (1996).

Battistuzzi, G., et al., "3-Arylpropanoate Esters through the Palladium-Catalyzed Reaction of Aryl Halides with Acrolein Diethyl Acetal", Synlett, vol. 8, pp. 1133-1136, (2003).

Benkeser, R.A., et al., "Additivity of Electrical Effects in Aromatic Electrophilic Substitutions as Determined by Desilylation Reactions", J. Am. Chem. Soc., vol. 80, pp. 5289-5293, (1958).

Boschelli, D.H., et al., "Synthesis and Src Kinase Inhibitory Activity of 2-Pheyl- and 2-Thienyl-7-phenylaminothieno[3,2-b]pyridine-6-carbonitriles", J. Med. Chem., vol. 48, pp. 3891-3902, (2005).

(Continued)

Primary Examiner — Yong Chu
(74) Attorney, Agent, or Firm — Hoxie & Associates LLC

(57) ABSTRACT

The invention relates to novel thiophene derivatives (I), their preparation and their use as pharmaceutically active compounds. Said compounds particularly act as immunomodulating agents. Formula (I).

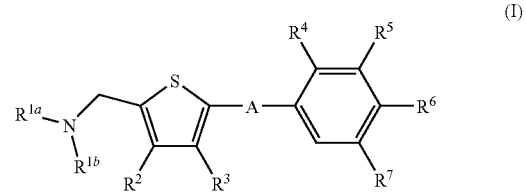

15 Claims, No Drawings

OTHER PUBLICATIONS

Brain, C.T., et al., "Novel procedure for the synthesis of 1,3,4-oxadiazoles from 1,2-diacylhydrazines using polymer-supported Burgess reagent under microwave conditions", Tetrahedron Lett., vol. 40, pp. 3275-3278, (1999).

Carpenter, A.J., et al., "Chemoselective Protection of Heteroaromatic Aldehydes as Imidazolidine Derivatives. Preparation of 5-Substituted Furan- and Thiophene-2-Carboxaldehydes via Metallo-Imidazolidine Intermediates", Tetrahedron, vol. 41, pp. 3803-3812, (1985).

Chakraborti, A.K., et al., "One-Pot Synthesis of Nitriles from Aldehydes Under Microwave Irradiation: Influence of the Medium and Mode of Microwave Irradiation on Product Formation", Tetrahedron, vol. 55, pp. 13265-13268, (1999).

Choong, I.C., et al., "Identification of Potent and Selective Small-Molecule Inhibitors of Caspase-3 through the Use of Extended Tethering and Structure-Based Drug Design", J. Med. Chem., vol. 45, pp. 5005-5022, (2002).

Constantino, G., et al., "Stereoselective Synthesis and Preliminary Evaluation of (+)- and (−)-3-methyl-5-carboxy-thien-2-yl-glycine (3-MATIDA): Identification of (+)-3-MATIDA as a Novel mGluR1 Competitive Antagonist", Il Farmaco, vol. 59, pp. 93-99, (2004).

Cui, J., et al., "Design and Synthesis of Highly Constrained Factor Xa Inhibitors: Amidine-Substituted Bis(benzoyl)-[1,3]-diazepan-2-ones and Bis(benzylidene)-bis(gem-dimethyl)cycloketones", Biorg. Med. Chem., vol. 11, pp. 3379-3392 (2003).

Detty, M.R., et al., "Studies toward Alkylthiophene-2-Carboxaldehydes. Reduction of 3-Alkenylthiophenes with Triethylsilane/Trifluoroacetic Acid. Regioselectivity in Formylation Reactions of 3-Alkylthiophenes", Heterocycles, vol. 40, pp. 925-937, (1995).

Doyle, M.P., et al., "Alkyl Nitrite-Metal Halide Deamination Reactions. 2. Substitutive Deamination of Arylamines by Alkyl Nitrites and Copper (II) Halides. A Direct and Remarkably Efficient Conversion of Arylamines to Aryl Halides", J. Org. Chem., vol. 42, pp. 2426-2429, (1977).

Gangloff, A.R., et al., "Synthesis of 3,5-disubstituted-1,2,4-oxadiazoles using tetrabutylammonium fluoride as a mild and efficient catalyst", Tetrahedron Lett., vol. 42, pp. 1441-1443, (2001).

Garcia, M.A., et al., "Synthesis, Biological Evaluation, and Three-Dimensional Quantitative Structure-Activity Relationship Study of Small-Molecule Positive Modulators of Adrenomedullin", J. Med. Chem., vol. 48, pp. 4068-4075, (2005).

Gould, N.P., et al., "Dianions of Methylated Thiophene-2-Carboxylic Acids: Their Formation and Reactivity", J. Org. Chem., vol. 45, pp. 4528-4530, (1980).

Gould, P.L., "Salt Selection for Basic Drugs", International Journal of Pharmaceutics, vol. 33, pp. 201-217, (1986).

Greene, T.W., et al., Protective Groups in Organic Synthesis, 2nd Edition, Wiley New York, (1991).

Hamze, A., et al., "Synthesis of Various 3-Substituted 1,2,4-Oxadiazole-Containing Chiral â3- and r-Amino Acids from Fmoc-Protected Aspartic Acid", J. Org. Chem., vol. 68, pp. 7316-7321, (2003).

Hla, T., et al., "An Abundant Transcript Induced in Differentiating Human Endothelial Cells Encodes a Polypeptide with Structural Similarities to G-protein-coupled Receptors", Biol. Chem., vol. 265, pp. 9308-9313, (1990).

John, E.O., et al., "Reactions of (Difluoroamino)difluoroacetonitrile and (Difluoroamino) difluoroacetamidoxime", Inorganic Chemistry, vol. 27, pp. 3100-3104, (1988).

Kaboudin, B., et al., "One-Pot Synthesis of 1,2,4-Oxadiazoles Mediated by Microwave Irradiation Under Solvent-Free Condition", Heterocycles, vol. 60, No. 10, pp. 2287-2292, (2003).

Kiryanov, A. A., et al., "Synthesis of 2-Alkoxy-Substituted Thiophenes, 1,3-Thiazoles, and Related S-Heterocycles via Lawesson's Reagent-Mediated Cyclization under Microwave Irradiation: Applications for Liquid Crystal Synthesis", J. Org. Chem., vol. 66, pp. 7925-7929, (2001).

Kocienski, P. J., Protecting Groups, Thieme Stuttgart, (1994).

Meyer, E., et al., "Synthesis of New 1,2,4- and 1,3,4-Oxadiazole Derivatives", Synthesis, No. 6, pp. 899-905, (2003).

Poulain, R.F., et al. "Parallel synthesis of 1,2,4-oxadiazoles from carboxylic acids using an improved, uronium-based, activation", Tetrahedron Lett., vol. 42, pp. 1495-1498, (2001).

Remington, The Science and Practice of Pharmacy, $21^{st}$ Edition (2005), Part 5, "Pharmaceutical Manufacturing" [published by Lippincott Williams & Wilkins].

Roth, B., et al., "2,4-Diamino-5-benzylpyrimidines and Analogues as Antibacterial Agents. 9. Lipophilic Trimethoprim Analogues as Antigonococcal Agents", J. Med. Chem., vol. 31, pp. 122-129, (1988).

Shilai, M., et al., "Selective Metallation of Thiophene and Thiazole Rings with Magnesium Amide Base", J. Chem. Soc. Perkin Trans. 1, pp. 442-444, (2001).

Smith, T.E., et al., "Effects of Base, Electrophile, and Substrate on the Selective Alkylation of Heteroaromatic Systems", Heterocycles, vol. 57, pp. 1211-1217, (2002).

Srivastava, R.M., et al., Synthesis of 3-Aryl-5-[Thien-3-Yl Methyl]-1,2,4-Oxadiazoles, Synthetic Commun., vol. 29, pp. 1437-1450, (1999).

Suzuki, T., et al., "Synthesis of the Selective 5-Hydroxytryptamine4 (5-$HT_4$) Receptor Agonist (+)-(S)-2-Chloro-5-methoxy-4-[5-(2-piperidylmethyl)-1,2,4-oxadiazol-3-yl]aniline", Chem. Pharm. Bull., vol. 47, No. 1, pp. 120-122, (1999).

Trapani, G., et al., "Propofol Analogues. Synthesis, Relationships between Structure and Affinity at $GABA_A$ Receptor in Rat Brain, and Differential Electrophysiological Profile at Recombinant Human $GABA_A$ Receptors". J. Med. Chem., vol. 41, pp. 1846-1854, (1998).

Wynberg, H., et al., "The Synthesis of 1H,3H-Thieno[3,4-c]thiophene", J. Org. Chem., vol. 29, pp. 1919-1921, (1964).

Zanon, J., et al., "Copper-Catalyzed Domino Halide Exchange-Cyanation of Aryl Bromides", J. Am. Chem. Soc., vol. 125, pp. 2890-2891, (2003).

Zhang, Y., et al., "Synthesis, Optical, and Electrochemical Properties of a New Family of Dendritic Oligothiophenes", J. Org. Chem., vol. 71, pp. 9475-9483, (2006).

* cited by examiner

THIOPHENE DERIVATIVES AS AGONISTS OF S1P1/EDG1

CROSS REFERENCE TO RELATED APPLICATIONS

This application is a United States National Stage Application under 35 USC §371 of PCT/IB2008/055156, filed Dec. 9, 2008, which claims the benefit of International Application No. PCT/IB2007/054991, filed Dec. 10, 2007 the contents of each of which are incorporated herein by reference.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol Chem.* 265 (1990), 9308-9313; WO 91/15583 published Oct. 17, 1991; WO 99/46277 published Sep. 16, 1999. The potency and efficacy of the compounds of Formula (I) are assessed using a GTPγS assay to determine $EC_{50}$ values and by measuring the circulating lymphocytes in the rat after oral administration, respectively (see in Examples).

i) The invention relates to novel thiophene compounds of the Formula (I),

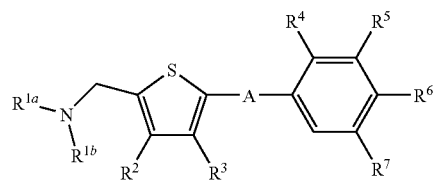

Formula (I)

wherein
A represents

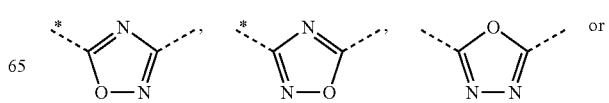

or

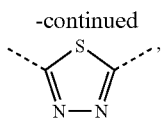

wherein the asterisks indicate the bond that is linked to the thiophene group of Formula (I);

$R^{1a}$ represents $C_{1-5}$-alkyl, $C_{3-5}$-cycloalkyl, or 2-hydroxyethyl;

$R^{1b}$ represents hydrogen or $C_{1-3}$-alkyl;

or $R^{1a}$ and $R^{1b}$, together with the nitrogen to which they are attached, form an azetidine, a pyrrolidine, a piperidine, or a morpholine ring;

$R^2$ represents hydrogen or $C_{1-2}$-alkyl;

$R^3$ represents hydrogen or $C_{1-2}$-alkyl;

$R^4$ represents hydrogen, $C_{1-2}$-alkyl, methoxy, or halogen;

$R^5$ represents hydrogen, $C_{1-4}$-alkyl, or $C_{1-4}$-alkoxy;

$R^6$ represents hydroxy-$C_{1-4}$-alkyl, di-(hydroxy-$C_{1-4}$-alkyl)-$C_{1-4}$-alkyl, 2,3-dihydroxypropyl, —$CH_2$—$(CH_2)_n$—$NR^{61}R^{62}$, —$CH_2$—$(CH_2)_n$—$NHCOR^{64}$, —$CH_2$—$(CH_2)_n$—$NHSO_2R^{63}$, —$CH_2$—$CH_2$—COOH, —$CH_2$—$CH_2$—$CONR^{61}R^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, —$CH_2$—CH(OH)—$CH_2$—$NR^{61}R^{62}$, —$CH_2$—CH(OH)—$CH_2$—$NHCOR^{64}$, —$CH_2$—CH(OH)—$CH_2$—$NHSO_2R^{63}$, —CO—$NHR^{61}$, hydroxy, hydroxy-$C_{2-4}$-alkoxy, di-(hydroxy-$C_{1-4}$-alkyl)-$C_{1-4}$-alkoxy, 2,3-dihydroxypropoxy, 2-hydroxy-3-methoxy-propoxy, —$OCH_2$—$(CH_2)_m$—$NR^{61}R^{62}$, —$OCH_2$—$(CH_2)_m$—NH-$COR^{64}$, —$OCH_2$—$(CH_2)_m$—$NHSO_2R^{63}$, 2-[(azetidine-3-carboxylic acid)-1-yl]-ethoxy, 2-[(pyrrolidine-2-carboxylic acid)-1-yl]-ethoxy, 2-[(pyrrolidine-3-carboxylic acid)-1-yl]-ethoxy, —$OCH_2$—CH(OH)—$CH_2$—$NR^{61}R^{62}$, —$OCH_2$—CH(OH)—$CH_2$—$NHCOR^{64}$, —$OCH_2$—CH(OH)—$CH_2$—$NHSO_2R^{63}$, 3-[(azetidine-3-carboxylic acid)-1-yl]-2-hydroxypropoxy, 2-hydroxy-3-[(pyrrolidine-2-carboxylic acid)-1-yl]-propoxy, 2-hydroxy-3-[(pyrrolidine-3-carboxylic acid)-1-yl]-propoxy, —$NR^{61}R^{62}$, —NHCO—$R^{64}$, or —$SO_2NH$—$R^{61}$;

$R^{61}$ represents hydrogen, methyl, ethyl, 2-hydroxyethyl, 2-hydroxy-1-hydroxymethyl-ethyl, 2,3-dihydroxy-propyl, 2-$C_{1-2}$-alkoxyethyl, 3-hydroxypropyl, 2-aminoethyl, 2-($C_{1-4}$-alkylamino)ethyl, 2-(di-($C_{1-4}$-alkyl)amino)ethyl, carboxymethyl, ($C_{1-4}$-alkylcarboxy)methyl, 2-carboxyethyl, or 2-($C_{1-4}$-alkylcarboxy)ethyl;

$R^{62}$ represents hydrogen or methyl;

$R^{63}$ represents methyl, ethyl, methylamino, ethylamino, or dimethylamino;

$R^{64}$ represents hydroxymethyl, 2-hydroxyethyl, aminomethyl, methylaminomethyl, dimethylaminomethyl, 2-aminoethyl, or 2-methylamino-ethyl;

m represents the integer 1 or 2;

n represents 0, 1, or 2; and $R^7$ represents hydrogen, $C_{1-2}$-alkyl, or halogen.

The general terms used hereinbefore and hereinafter preferably have, within this disclosure, the following meanings, unless otherwise indicated:

The term "$C_{x-y}$-alkyl" (x and y each being an integer) refers to a saturated straight or branched hydrocarbon chain with x to y carbon atoms. For example, a $C_{1-5}$-alkyl group contains from one to five carbon atoms. Representative examples of $C_{1-5}$-alkyl groups include methyl, ethyl, n-propyl, iso-propyl, n-butyl, iso-butyl, sec-butyl, tert-butyl, n-pentyl, iso-pentyl, 3-pentyl, and 2,2,2-trimethylethyl. Preferred examples of $C_{1-5}$-alkyl groups are methyl, ethyl, n-propyl, iso-propyl, n-butyl, iso-butyl, and 3-pentyl. Preferred examples of $C_{1-4}$-alkyl groups are methyl, ethyl, n-propyl, iso-propyl, n-butyl, and iso-butyl. Preferred examples of $C_{1-3}$-alkyl groups are methyl and ethyl.

The term "$C_{x-y}$-alkoxy" (x and y each being an integer) refers to an alkyl-O— group wherein the alkyl group refers to a straight or branched hydrocarbon chain with x to y carbon atoms. For example, a $C_{1-4}$-alkoxy group contains from one to four carbon atoms and includes methoxy, ethoxy, n-propoxy, iso-propoxy, n-butoxy, iso-butoxy, sec-butoxy, and tert-butoxy. Preferred examples of $C_{2-4}$-alkoxy groups are ethoxy, n-propoxy, and iso-propoxy.

The term "$C_{x-y}$-cycloalkyl" (x and y each being an integer) refers to a saturated cyclic hydrocarbon ring system with x to y carbon ring atoms. For example, a $C_{3-5}$-cycloalkyl group contains from three to five carbon ring atoms and thus includes cyclopropyl, cyclobutyl, and cyclopentyl. Analogously, "$C_{3-4}$-cycloalkyl" includes cyclopropyl and cyclobutyl.

The term "halogen" means fluoro, chloro, bromo or iodo (preferably fluoro or chloro; especially preferred chloro).

ii) A particular embodiment of the invention relates to thiophene derivatives according to embodiment i), wherein A represents

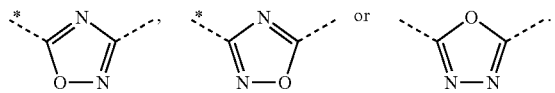

iii) Another particular embodiment of the invention relates to thiophene derivatives according to embodiment i), wherein A represents

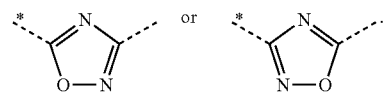

iv) Another particular embodiment of the invention relates to thiophene derivatives according to embodiment i), wherein A represents

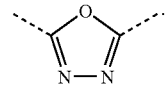

v) Another particular embodiment of the invention relates to thiophene derivatives according to any one of the embodiments i) to iv), wherein $R^{1a}$ represents $C_{4-5}$-alkyl.

vi) Another particular embodiment of the invention relates to thiophene derivatives according to any one of the embodiments i) to iv), wherein $R^{1a}$ represents $C_{1-4}$-alkyl, $C_{3-4}$-cycloalkyl, or 2-hydroxyethyl, and $R^{1b}$ represents $C_{1-3}$-alkyl; or $R^{1a}$ and $R^{1b}$, together with the nitrogen to which they are attached, form an azetidine or a pyrrolidine ring.

vii) Another particular embodiment of the invention relates to thiophene derivatives according to any one of the embodiments i) to iv), wherein $R^{1a}$ represents $C_{1-4}$-alkyl and $R^{1b}$ represents $C_{1-2}$-alkyl.

viii) Another particular embodiment of the invention relates to thiophene derivatives according to any one of the embodiments i) to vii), wherein $R^2$ represents $C_{1-2}$-alkyl.

ix) Another particular embodiment of the invention relates to thiophene derivatives according to any one of the embodiments i) to vii), wherein $R^2$ represents methyl.

x) Another particular embodiment of the invention relates to thiophene derivatives according to any one of the embodiments i) to ix), wherein $R^3$ represents hydrogen.

xi) Another particular embodiment of the invention relates to thiophene derivatives according to any one of the embodiments i) to x), wherein $R^4$ represents methoxy, and $R^5$ and $R^7$ represent hydrogen.

xii) Another particular embodiment of the invention relates to thiophene derivatives according to any one of the embodiments i) to x), wherein $R^4$ represents hydrogen, $R^5$ represents $C_{1-3}$-alkyl or methoxy, and $R^7$ represents $C_{1-2}$-alkyl or chloro.

xiii) Another particular embodiment of the invention relates to thiophene derivatives according to any one of the embodiments i) to x), wherein $R^4$ represents hydrogen, $R^5$ represents $C_{1-2}$-alkyl or methoxy, and $R^7$ represents methyl or chloro.

xiv) Another particular embodiment of the invention relates to thiophene derivatives according to any one of the embodiments i) to x), wherein $R^4$ represents hydrogen, $R^5$ represents ethyl or methoxy, and $R^7$ represents methyl or chloro.

xv) Another particular embodiment of the invention relates to thiophene derivatives according to any one of the embodiments i) to x), wherein $R^4$ represents hydrogen, $R^5$ represents ethyl, and $R^7$ represents methyl.

xvi) Another particular embodiment of the invention relates to thiophene derivatives according to any one of the embodiments i) to xv), wherein $R^6$ represents di-(hydroxy-$C_{1-4}$-alkyl)-$C_{1-4}$-alkyl, 2,3-dihydroxypropyl, —$CH_2$—$(CH_2)_n$—$NHCOR^{64}$, —$CH_2$—$(CH_2)_n$—$NHSO_2R^{63}$, —$CH_2$—$CH_2$—COOH, —$CH_2$—$CH_2$—$CONR^{61}R^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, —$CH_2$—CH(OH)—$CH_2$—$NR^{61}R^{62}$, —$CH_2$—CH(OH)—$CH_2$—$NHCOR^{64}$, —$CH_2$—CH(OH)—$CH_2$—$NHSO_2R^{63}$, —CO—$NHR^{61}$, hydroxy-$C_{2-4}$-alkoxy, di-(hydroxy-$C_{1-4}$-alkyl)-$C_{1-4}$-alkoxy, 2,3-dihydroxypropoxy, 2-hydroxy-3-methoxy-propoxy, —$OCH_2$—$(CH_2)_m$—$NR^{61}R^{62}$, —$OCH_2$—$(CH_2)_m$—$NHCOR^{64}$, —$OCH_2$—$(CH_2)_m$—$NHSO_2R^{63}$, 2-[(azetidine-3-carboxylic acid)-1-yl]-ethoxy, 2-[(pyrrolidine-2-carboxylic acid)-1-yl]-ethoxy, 2-[(pyrrolidine-3-carboxylic acid)-1-yl]-ethoxy, —$OCH_2$—CH(OH)—$CH_2$—$NR^{61}R^{62}$, —$OCH_2$—CH(OH)—$CH_2$—$NHCOR^{64}$, —$OCH_2$—CH(OH)—$CH_2$—$NHSO_2R^{63}$, 3-[(azetidine-3-carboxylic acid)-1-yl]-2-hydroxypropoxy, 2-hydroxy-3-[(pyrrolidine-2-carboxylic acid)-1-yl]-propoxy, 2-hydroxy-3-[(pyrrolidine-3-carboxylic acid)-1-yl]-propoxy, or —$NR^{61}R^{62}$.

xvii) Another particular embodiment of the invention relates to thiophene derivatives according to any one of the embodiments i) to xv), wherein $R^6$ represents —$CH_2$—$CH_2$—COOH, —$CH_2$—$CH_2$—$CONR^{61}R^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, hydroxy, hydroxy-$C_{2-4}$-alkoxy, di-(hydroxy-$C_{1-4}$-alkyl)-$C_{1-4}$-alkoxy, 2,3-dihydroxypropoxy, —$OCH_2$—$(CH_2)_m$—$NR^{61}R^{62}$, —$OCH_2$—$(CH_2)_m$—$NHCOR^{64}$, —$OCH_2$—$(CH_2)_m$—$NHSO_2R^{63}$, 2-[(azetidine-3-carboxylic acid)-1-yl]-ethoxy, 2-[(pyrrolidine-2-carboxylic acid)-1-yl]-ethoxy, 2-[(pyrrolidine-3-carboxylic acid)-1-yl]-ethoxy, —$OCH_2$—CH(OH)—$CH_2$—$NR^{61}R^{62}$, —$OCH_2$—CH(OH)—$CH_2$—$NHCOR^{64}$, —$OCH_2$—CH(OH)—$CH_2$—$NHSO_2R^{63}$, 3-[(azetidine-3-carboxylic acid)-1-yl]-2-hydroxypropoxy, 2-hydroxy-3-[(pyrrolidine-2-carboxylic acid)-1-yl]-propoxy, or 2-hydroxy-3-[(pyrrolidine-3-carboxylic acid)-1-yl]-propoxy.

xviii) Another particular embodiment of the invention relates to thiophene derivatives according to any one of the embodiments i) to xv), wherein $R^6$ represents —$CH_2$—$CH_2$—$CONR^{61}R^{62}$, hydroxy, hydroxy-$C_{2-4}$-alkoxy, di-(hydroxy-$C_{1-4}$-alkyl)-$C_{1-4}$-alkoxy, 2,3-dihydroxypropoxy, —$OCH_2$—$(CH_2)_m$—$NR^{61}R^{62}$, —$OCH_2$—$(CH_2)_m$—$NHCOR^{64}$, —$OCH_2$—$(CH_2)_m$—$NHSO_2R^{63}$, —$OCH_2$—CH(OH)—$CH_2$—$NR^{61}R^{62}$, —$OCH_2$—CH(OH)—$CH_2$—$NHCOR^{64}$, or —$OCH_2$—CH(OH)—$CH_2$—$NHSO_2R^{63}$.

xix) Another particular embodiment of the invention relates to thiophene derivatives according to any one of the embodiments i) to xv), wherein $R^6$ represents di-(hydroxy-$C_{1-4}$-alkyl)-$C_{1-4}$-alkoxy, 2,3-dihydroxypropoxy, —$OCH_2$—$(CH_2)_m$—$NR^{61}R^{62}$, —$OCH_2$—$(CH_2)_m$—$NHCOR^{64}$, —$OCH_2$—CH(OH)—$CH_2$—$NR^{61}R^{62}$, or —$OCH_2$—CH(OH)—$CH_2$—$NHCOR^{64}$.

xx) Another particular embodiment of the invention relates to thiophene derivatives according to any one of the embodiments i) to xv), wherein $R^6$ represents di-(hydroxy-$C_{1-4}$-alkyl)-$C_{1-4}$-alkoxy, 2,3-dihydroxypropoxy, —$OCH_2$—CH(OH)—$CH_2$—$NR^{61}R^{62}$, or —$OCH_2$—CH(OH)—$CH_2$—$NHCOR^{64}$.

xxi) Another particular embodiment of the invention relates to thiophene derivatives according to any one of the embodiments i) to xv), wherein $R^6$ represents 2,3-dihydroxypropoxy or —$OCH_2$—CH(OH)—$CH_2$—$NHCOR^{64}$.

xxii) Another particular embodiment of the invention relates to thiophene derivatives according to any one of the embodiments i) to xv), wherein $R^6$ represents hydroxy-$C_{1-4}$-alkyl, 2,3-dihydroxypropyl, —$CH_2$—$(CH_2)_n$—$NR^{61}R^{62}$, —$CH_2$—$(CH_2)_n$—$NHCOR^{64}$, —$CH_2$—$(CH_2)_n$—$NHSO_2R^{63}$, —$CH_2$—$CH_2$—COOH, —$CH_2$—$CH_2$—$CONR^{61}R^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, —$CH_2$—CH(OH)—$CH_2$—$NR^{61}R^{62}$, —$CH_2$—CH(OH)—$CH_2$—$NHCOR^{64}$, —$CH_2$—CH(OH)—$CH_2$—$NHSO_2R^{63}$, —CO—$NHR^{61}$, hydroxy, hydroxy-$C_{2-4}$-alkoxy, 2,3-dihydroxypropoxy, —$OCH_2$—$(CH_2)_m$—$NR^{61}R^{62}$, —$OCH_2$—CH(OH)—$CH_2$—$NR^{61}R^{62}$, —$OCH_2$—CH(OH)—$CH_2$—$NHCOR^{64}$, 3-[(azetidine-3-carboxylic acid)-1-yl]-2-hydroxypropoxy, 2-hydroxy-3-[(pyrrolidine-2-carboxylic acid)-1-yl]-propoxy, 2-hydroxy-3-[(pyrrolidine-3-carboxylic acid)-1-yl]-propoxy, —$NR^{61}R^{62}$, —NHCO—$R^{64}$, or —$SO_2NH$—$R^{61}$.

xxiii) Another particular embodiment of the invention relates to thiophene derivatives according to any one of the embodiments i) to xviii), and xxii), wherein $R^{63}$ represents methyl or methylamino.

xxiv) Another particular embodiment of the invention relates to thiophene derivatives according to any one of the embodiments i) to xx), xxii), and xxiii), wherein $R^{61}$ represents methyl, 2-hydroxyethyl, carboxymethyl, or 2-carboxyethyl.

xxv) Another particular embodiment of the invention relates to thiophene derivatives according to any one of the embodiments i) to xx), and xxii) to xxiv), wherein $R^{62}$ represents hydrogen.

xxvi) Another particular embodiment of the invention relates to thiophene derivatives according to any one of the embodiments i) to xxv), wherein $R^{64}$ represents hydroxymethyl or 2-hydroxyethyl.

xxvii) A further embodiment of the invention relates to thiophene derivatives according to embodiment i), wherein A represents

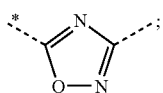

$R^{1a}$ represents $C_{1-5}$-alkyl or 2-hydroxyethyl;
$R^{1b}$ represents hydrogen or $C_{1-3}$-alkyl;
or $R^{1a}$ and $R^{1b}$, together with the nitrogen to which they are attached, form an azetidine, a pyrrolidine, a piperidine, or a morpholine ring;
$R^2$ represents hydrogen or $C_{1-2}$-alkyl;
$R^3$ represents hydrogen or $C_{1-2}$-alkyl;
$R^4$ represents hydrogen;
$R^5$ represents $C_{1-4}$-alkyl;
$R^6$ represents hydroxy-$C_{1-4}$-alkyl, —$CH_2$—$CH_2$—COOH, hydroxy, 2,3-dihydroxypropoxy, or —$OCH_2$—$CH(OH)$—$CH_2$—$NHCOR^{64}$;
$R^{64}$ represents hydroxymethyl; and
$R^7$ represents $C_{1-2}$-alkyl.

The compounds of Formula (I) may contain one or more stereogenic or asymmetric centers, such as one or more asymmetric carbon atoms. The compounds of Formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to salts, especially pharmaceutically acceptable salts, of a compound of Formula (I), as appropriate and expedient.

Salts are preferably the pharmaceutically acceptable salts of the compounds of Formula (I).

The term "pharmaceutically acceptable salts" refers to non-toxic, inorganic or organic acid and/or base addition salts. Reference can be made to "Salt selection for basic drugs", Int. J. Pharm. (1986), 33, 201-217.

Examples of preferred compounds are selected from the group consisting of:

N-(3-{4-[5-(5-dimethylaminomethyl-thiophen-2-yl)-[1,2,4]oxadiazol-3-yl]-2,6-dimethyl-phenoxy}-2-hydroxy-propyl)-2-hydroxy-acetamide;
3-[2,6-dimethyl-4-(5-{4-methyl-5-[(methyl-propyl-amino)-methyl]-thiophen-2-yl}-[1,2,4]oxadiazol-3-yl)-phenoxy]-propane-1,2-diol;
N-(3-{2,6-dimethyl-4-[5-(4-methyl-5-methylaminomethyl-thiophen-2-yl)-[1,2,4]oxadiazol-3-yl]-phenoxy}-2-hydroxy-propyl)-2-hydroxy-acetamide;
2-hydroxy-N-[2-hydroxy-3-(4-{5-[5-(isopropylamino-methyl)-4-methyl-thiophen-2-yl]-[1,2,4]oxadiazol-3-yl}-2,6-dimethyl-phenoxy)-propyl]-acetamide;
N-(3-{4-[5-(5-dimethylaminomethyl-4-methyl-thiophen-2-yl)-[1,2,4]oxadiazol-3-yl]-2,6-dimethyl-phenoxy}-2-hydroxy-propyl)-2-hydroxy-acetamide;
N-{3-[2,6-dimethyl-4-(5-{4-methyl-5-[(methyl-propyl-amino)-methyl]-thiophen-2-yl}-[1,2,4]oxadiazol-3-yl)-phenoxy]-2-hydroxy-propyl}-2-hydroxy-acetamide;
2-hydroxy-N-(2-hydroxy-3-{4-[5-(5-{[(2-hydroxy-ethyl)-methyl-amino]-methyl}-4-methyl-thiophen-2-yl)-[1,2,4]oxadiazol-3-yl]-2,6-dimethyl-phenoxyl-propyl)-acetamide;
N-(3-{4-[5-(5-{[ethyl-(2-hydroxy-ethyl)-amino]-methyl}-4-methyl-thiophen-2-yl)-[1,2,4]oxadiazol-3-yl]-2,6-dimethyl-phenoxy}-2-hydroxy-propyl)-2-hydroxy-acetamide;
N-(3-{2,6-dimethyl-4-[5-(4-methyl-5-pyrrolidin-1-ylmethyl-thiophen-2-yl)-[1,2,4]oxadiazol-3-yl]-phenoxy}-2-hydroxy-propyl)-2-hydroxy-acetamide;
N-(3-{2,6-dimethyl-4-[5-(4-methyl-5-piperidin-1-ylmethyl-thiophen-2-yl)-[1,2,4]oxadiazol-3-yl]-phenoxy}-2-hydroxy-propyl)-2-hydroxy-acetamide;
3-{4-[5-(5-diethylaminomethyl-4-methyl-thiophen-2-yl)-[1,2,4]oxadiazol-3-yl]-2,6-dimethyl-phenyl}-propionic acid;
N—((S)-3-{4-[5-(5-dimethylaminomethyl-4-methyl-thiophen-2-yl)-[1,2,4]oxadiazol-3-yl]-2-ethyl-6-methyl-phenoxy}-2-hydroxy-propyl)-2-hydroxy-acetamide;
N—{(S)-3-[2-ethyl-4-(5-{5-[(ethyl-methyl-amino)-methyl]-4-methyl-thiophen-2-yl}-[1,2,4]oxadiazol-3-yl)-6-methyl-phenoxy]-2-hydroxy-propyl}-2-hydroxy-acetamide;
N—{(S)-3-[2-ethyl-6-methyl-4-(5-{4-methyl-5-[(methyl-propyl-amino)-methyl]-thiophen-2-yl}-[1,2,4]oxadiazol-3-yl)-phenoxy]-2-hydroxy-propyl}-2-hydroxy-acetamide;
N—{(S)-3-[4-(5-{5-[(butyl-methyl-amino)-methyl]-4-methyl-thiophen-2-yl}-[1,2,4]oxadiazol-3-yl)-2-ethyl-6-methyl-phenoxy]-2-hydroxy-propyl}-2-hydroxy-acetamide;
N—{(S)-3-[2-ethyl-4-(5-{5-[(isobutyl-methyl-amino)-methyl]-4-methyl-thiophen-2-yl}-[1,2,4]oxadiazol-3-yl)-6-methyl-phenoxy]-2-hydroxy-propyl}-2-hydroxy-acetamide;
N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-2-hydroxy-acetamide;
N—{(S)-3-[2-ethyl-4-(5-{5-[(ethyl-propyl-amino)-methyl]-4-methyl-thiophen-2-yl}-[1,2,4]oxadiazol-3-yl)-6-methyl-phenoxy]-2-hydroxy-propyl}-2-hydroxy-acetamide;
N—{(S)-3-[2-ethyl-4-(5-{5-[(ethyl-isopropyl-amino)-methyl]-4-methyl-thiophen-2-yl}-[1,2,4]oxadiazol-3-yl)-6-methyl-phenoxy]-2-hydroxy-propyl}-2-hydroxy-acetamide;
N—{(S)-3-[4-(5-{5-[(butyl-ethyl-amino)-methyl]-4-methyl-thiophen-2-yl}-[1,2,4]oxadiazol-3-yl)-2-ethyl-6-methyl-phenoxy]-2-hydroxy-propyl}-2-hydroxy-acetamide;
3-[4-(5-{5-[(butyl-methyl-amino)-methyl]-4-methyl-thiophen-2-yl}-[1,2,4]oxadiazol-3-yl)-2-ethyl-6-methyl-phenyl]-propionic acid; and
3-{4-[5-(5-diethylaminomethyl-4-methyl-thiophen-2-yl)-[1,2,4]oxadiazol-3-yl]-2-ethyl-6-methyl-phenyl}-propionic acid.

Examples of preferred compounds are further selected from the group consisting of:

N—((S)-3-{4-[5-(5-dimethylaminomethyl-thiophen-2-yl)-[1,2,4]oxadiazol-3-yl]-2,6-dimethyl-phenoxy}-2-hydroxy-propyl)-2-hydroxy-acetamide;
N—((R)-3-{4-[5-(5-dimethylaminomethyl-thiophen-2-yl)-[1,2,4]oxadiazol-3-yl]-2,6-dimethyl-phenoxy}-2-hydroxy-propyl)-2-hydroxy-acetamide;
(S)-3-[2,6-dimethyl-4-(5-{4-methyl-5-[(methyl-propyl-amino)-methyl]-thiophen-2-yl}-[1,2,4]oxadiazol-3-yl)-phenoxy]-propane-1,2-diol;
(R)-3-[2,6-dimethyl-4-(5-{4-methyl-5-[(methyl-propyl-amino)-methyl]-thiophen-2-yl}-[1,2,4]oxadiazol-3-yl)-phenoxy]-propane-1,2-diol;
N—((S)-3-{2,6-dimethyl-4-[5-(4-methyl-5-methylaminomethyl-thiophen-2-yl)-[1,2,4]oxadiazol-3-yl]-phenoxy}-2-hydroxy-propyl)-2-hydroxy-acetamide;
N—((R)-3-{2,6-dimethyl-4-[5-(4-methyl-5-methylaminomethyl-thiophen-2-yl)-[1,2,4]oxadiazol-3-yl]-phenoxy}-2-hydroxy-propyl)-2-hydroxy-acetamide;

2-hydroxy-N—[(S)-2-hydroxy-3-(4-{5-[5-(isopropylamino-methyl)-4-methyl-thiophen-2-yl]-[1,2,4]oxadiazol-3-yl}-2,6-dimethyl-phenoxy)-propyl]-acetamide;
2-hydroxy-N—[(R)-2-hydroxy-3-(4-{5-[5-(isopropylamino-methyl)-4-methyl-thiophen-2-yl]-[1,2,4]oxadiazol-3-yl}-2,6-dimethyl-phenoxy)-propyl]-acetamide;
N—((S)-3-{4-[5-(5-dimethylaminomethyl-4-methyl-thiophen-2-yl)-[1,2,4]oxadiazol-3-yl]-2,6-dimethyl-phenoxy}-2-hydroxy-propyl)-2-hydroxy-acetamide;
N—((R)-3-{4-[5-(5-dimethylaminomethyl-4-methyl-thiophen-2-yl)-[1,2,4]oxadiazol-3-yl]-2,6-dimethyl-phenoxy}-2-hydroxy-propyl)-2-hydroxy-acetamide;
N—{(S)-3-[2,6-dimethyl-4-(5-{4-methyl-5-[(methyl-propyl-amino)-methyl]-thiophen-2-yl}-[1,2,4]oxadiazol-3-yl)-phenoxy]-2-hydroxy-propyl}-2-hydroxy-acetamide;
N—{(R)-3-[2,6-dimethyl-4-(5-{4-methyl-5-[(methyl-propyl-amino)-methyl]-thiophen-2-yl}-1,2,4]oxadiazol-3-yl)-phenoxy]-2-hydroxy-propyl}-2-hydroxy-acetamide;
2-hydroxy-N—((S)-2-hydroxy-3-{4-[5-(5-{[(2-hydroxy-ethyl)-methyl-amino]-methyl}-4-methyl-thiophen-2-yl)-[1,2,4]oxadiazol-3-yl]-2,6-dimethyl-phenoxy}-propyl)-acetamide;
2-hydroxy-N—((R)-2-hydroxy-3-{4-[5-(5-{[(2-hydroxy-ethyl)-methyl-amino]-methyl-4-methyl-thiophen-2-yl)-[1,2,4]oxadiazol-3-yl]-2,6-dimethyl-phenoxy}-propyl)-acetamide;
N—((S)-3-{4-[5-(5-{[ethyl-(2-hydroxy-ethyl)-amino]-methyl}-4-methyl-thiophen-2-yl)-[1,2,4]oxadiazol-3-yl]-2,6-dimethyl-phenoxy}-2-hydroxy-propyl)-2-hydroxy-acetamide;
N—((R)-3-{4-[5-(5-{[ethyl-(2-hydroxy-ethyl)-amino]-methyl}-4-methyl-thiophen-2-yl)-[1,2,4]oxadiazol-3-yl]-2,6-dimethyl-phenoxy}-2-hydroxy-propyl)-2-hydroxy-acetamide;
N—((S)-3-{2,6-dimethyl-4-[5-(4-methyl-5-pyrrolidin-1-ylmethyl-thiophen-2-yl)-[1,2,4]oxadiazol-3-yl]-phenoxy}-2-hydroxy-propyl)-2-hydroxy-acetamide;
N—((R)-3-{2,6-dimethyl-4-[5-(4-methyl-5-pyrrolidin-1-ylmethyl-thiophen-2-yl)-[1,2,4]oxadiazol-3-yl]-phenoxy}-2-hydroxy-propyl)-2-hydroxy-acetamide;
N—((S)-3-{2,6-dimethyl-4-[5-(4-methyl-5-piperidin-1-ylmethyl-thiophen-2-yl)-[1,2,4]oxadiazol-3-yl]-phenoxy}-2-hydroxy-propyl)-2-hydroxy-acetamide;
N—((R)-3-{2,6-dimethyl-4-[5-(4-methyl-5-piperidin-1-ylmethyl-thiophen-2-yl)-[1,2,4]oxadiazol-3-yl]-phenoxy}-2-hydroxy-propyl)-2-hydroxy-acetamide;
3-{4-[5-(5-diethylaminomethyl-4-methyl-thiophen-2-yl)-[1,2,4]oxadiazol-3-yl]-2,6-dimethyl-phenyl}-propionic acid;
N—((S)-3-{4-[5-(5-dimethylaminomethyl-4-methyl-thiophen-2-yl)-[1,2,4]oxadiazol-3-yl]-2-ethyl-6-methyl-phenoxy}-2-hydroxy-propyl)-2-hydroxy-acetamide;
N—{(S)-3-[2-ethyl-4-(5-{5-[(ethyl-methyl-amino)-methyl]-4-methyl-thiophen-2-yl}-[1,2,4]oxadiazol-3-yl)-6-methyl-phenoxy]-2-hydroxy-propyl}-2-hydroxy-acetamide;
N—{(S)-3-[2-ethyl-6-methyl-4-(5-{4-methyl-5-[(methyl-propyl-amino)-methyl]-thiophen-2-yl}-[1,2,4]oxadiazol-3-yl)-phenoxy]-2-hydroxy-propyl}-2-hydroxy-acetamide;
N—{(S)-3-[4-(5-{5-[(butyl-methyl-amino)-methyl]-4-methyl-thiophen-2-yl}-[1,2,4]oxadiazol-3-yl)-2-ethyl-6-methyl-phenoxy]-2-hydroxy-propyl}-2-hydroxy-acetamide;
N—{(S)-3-[2-ethyl-4-(5-{5-[(isobutyl-methyl-amino)-methyl]-4-methyl-thiophen-2-yl}-[1,2,4]oxadiazol-3-yl)-6-methyl-phenoxy]-2-hydroxy-propyl}-2-hydroxy-acetamide;
N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-2-hydroxy-acetamide;
N—{(S)-3-[2-ethyl-4-(5-{5-[(ethyl-propyl-amino)-methyl]-4-methyl-thiophen-2-yl}-[1,2,4]oxadiazol-3-yl)-6-methyl-phenoxy]-2-hydroxy-propyl}-2-hydroxy-acetamide;
N—{(S)-3-[2-ethyl-4-(5-{5-[(ethyl-isopropyl-amino)-methyl]-4-methyl-thiophen-2-yl}-[1,2,4]oxadiazol-3-yl)-6-methyl-phenoxy]-2-hydroxy-propyl}-2-hydroxy-acetamide;
N—{(S)-3-[4-(5-{5-[(butyl-ethyl-amino)-methyl]-4-methyl-thiophen-2-yl}-[1,2,4]oxadiazol-3-yl)-2-ethyl-6-methyl-phenoxy]-2-hydroxy-propyl}-2-hydroxy-acetamide;
3-[4-(5-{5-[(butyl-methyl-amino)-methyl]-4-methyl-thiophen-2-yl}-[1,2,4]oxadiazol-3-yl)-2-ethyl-6-methyl-phenyl]-propionic acid; and
3-{4-[5-(5-diethylaminomethyl-4-methyl-thiophen-2-yl)-[1,2,4]oxadiazol-3-yl]-2-ethyl-6-methyl-phenyl}-propionic acid.

Examples of preferred compounds are further selected from the group consisting of:
(R)-3-{4-[5-(5-dimethylaminomethyl-4-ethyl-thiophen-2-yl)-[1,2,4]oxadiazol-3-yl]-2-ethyl-6-methyl-phenoxyl-propane-1,2-diol;
(R)-3-[2-ethyl-4-(5-{4-ethyl-5-[(methyl-propyl-amino)-methyl]-thiophen-2-yl}-[1,2,4]oxadiazol-3-yl)-6-methyl-phenoxy]-propane-1,2-diol;
N—((S)-3-{4-[5-(5-dimethylaminomethyl-4-ethyl-thiophen-2-yl)-[1,2,4]oxadiazol-3-yl]-2-ethyl-6-methyl-phenoxy}-2-hydroxy-propyl)-2-hydroxy-acetamide;
N—{(S)-3-[2-ethyl-4-(5-{4-ethyl-5-[(methyl-propyl-amino)-methyl]-thiophen-2-yl}-[1,2,4]oxadiazol-3-yl)-6-methyl-phenoxy]-2-hydroxy-propyl}-2-hydroxy-acetamide;
3-{4-[5-(5-dimethylaminomethyl-4-ethyl-thiophen-2-yl)-[1,2,4]oxadiazol-3-yl]-2-ethyl-6-methyl-phenyl}-propionic acid;
3-[2-ethyl-4-(5-{4-ethyl-5-[(methyl-propyl-amino)-methyl]-thiophen-2-yl}-[1,2,4]oxadiazol-3-yl)-6-methyl-phenyl]-propionic acid;
N—((S)-3-{4-[5-(5-dimethylaminomethyl-4-methyl-thiophen-2-yl)-[1,2,4]oxadiazol-3-yl]-2,6-dimethyl-phenoxy}-2-hydroxy-propyl)-2-hydroxy-acetamide;
N—((S)-3-[4-(5-{5-[(butyl-methyl-amino)-methyl]-4-methyl-thiophen-2-yl}-[1,2,4]oxadiazol-3-yl)-2,6-dimethyl-phenoxy]-2-hydroxy-propyl}-2-hydroxy-acetamide;
2-hydroxy-N—{(S)-2-hydroxy-3-[4-(5-{5-[(isobutyl-methyl-amino)-methyl]-4-methyl-thiophen-2-yl}-[1,2,4]oxadiazol-3-yl)-2,6-dimethyl-phenoxy]-propyl}-acetamide;
N—{(S)-3-[4-(5-{5-[(ethyl-propyl-amino)-methyl]-4-methyl-thiophen-2-yl}-[1,2,4]oxadiazol-3-yl)-2,6-dimethyl-phenoxy]-2-hydroxy-propyl}-2-hydroxy-acetamide;
N—{(S)-3-[4-(5-{5-[(ethyl-isopropyl-amino)-methyl]-4-methyl-thiophen-2-yl}-[1,2,4]oxadiazol-3-yl)-2,6-dimethyl-phenoxy]-2-hydroxy-propyl}-2-hydroxy-acetamide;
N—{(S)-3-[2-ethyl-4-(5-{5-[(ethyl-isobutyl-amino)-methyl]-4-methyl-thiophen-2-yl}-[1,2,4]oxadiazol-3-yl)-6-methyl-phenoxy]-2-hydroxy-propyl}-2-hydroxy-acetamide;
(3-{4-[5-(5-diethylaminomethyl-4-methyl-thiophen-2-yl)-[1,2,4]oxadiazol-3-yl]-2-ethyl-6-methyl-phenyl}-propionylamino)-acetic acid;
{3-[2-ethyl-4-(5-{5-[(ethyl-propyl-amino)-methyl]-4-methyl-thiophen-2-yl}-[1,2,4]oxadiazol-3-yl)-6-methyl-phenyl]-propionylamino}-acetic acid;

3-{3-[2-ethyl-6-methyl-4-(5-{4-methyl-5-[(methyl-propyl-amino)-methyl]-thiophen-2-yl}-[1,2,4]oxadiazol-3-yl)-phenyl]-propionylamino}-propionic acid;

3-(3-{4-[5-(5-diethylaminomethyl-4-methyl-thiophen-2-yl)-[1,2,4]oxadiazol-3-yl]-2-ethyl-6-methyl-phenyl}-propionylamino)-propionic acid;

3-{3-[2-ethyl-4-(5-{5-[(ethyl-propyl-amino)-methyl]-4-methyl-thiophen-2-yl}-[1,2,4]oxadiazol-3-yl)-6-methyl-phenyl]-propionylamino}-propionic acid;

N—((S)-3-{4-[3-(5-dimethylaminomethyl-4-methyl-thiophen-2-yl)-[1,2,4]oxadiazol-5-yl]-2-ethyl-6-methyl-phenoxy}-2-hydroxy-propyl)-2-hydroxy-acetamide;

N—((S)-3-{4-[3-(5-diethylaminomethyl-4-methyl-thiophen-2-yl)-[1,2,4]oxadiazol-5-yl]-2-ethyl-6-methyl-phenoxy}-2-hydroxy-propyl)-2-hydroxy-acetamide;

N—((S)-3-{4-[5-(5-dimethylaminomethyl-4-methyl-thiophen-2-yl)-[1,3,4]oxadiazol-2-yl]-2-ethyl-6-methyl-phenoxy}-2-hydroxy-propyl)-2-hydroxy-acetamide;

N—((S)-3-{4-[5-(5-diethylaminomethyl-4-methyl-thiophen-2-yl)-[1,2,4]oxadiazol-3-yl]-2-methoxy-6-methyl-phenoxy}-2-hydroxy-propyl)-2-hydroxy-acetamide;

N—((S)-3-{2-chloro-4-[5-(5-diethylaminomethyl-4-methyl-thiophen-2-yl)-[1,2,4]oxadiazol-3-yl]-6-methyl-phenoxy}-2-hydroxy-propyl)-2-hydroxy-acetamide;

N—((S)-3-{4-[5-(5-diethylaminomethyl-4-methyl-thiophen-2-yl)-[1,2,4]oxadiazol-3-yl]-3-methyl-phenoxy}-2-hydroxy-propyl)-2-hydroxy-acetamide;

(S)-3-{2-chloro-4-[5-(5-diethylaminomethyl-4-methyl-thiophen-2-yl)-[1,2,4]oxadiazol-3-yl]-6-methyl-phenoxyl-propane-1,2-diol;

(S)-1-{4-[5-(5-diethylaminomethyl-4-methyl-thiophen-2-yl)-[1,2,4]oxadiazol-3-yl]-2-ethyl-6-methyl-phenoxy}-3-(2-hydroxy-ethylamino)-propan-2-ol;

3-((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propylamino)-propan-1-ol;

3-((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propylamino)-propane-1,2-diol;

2-((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propylamino)-propane-1,3-diol;

(S)-1-{4-[5-(5-diethylaminomethyl-4-methyl-thiophen-2-yl)-[1,2,4]oxadiazol-3-yl]-2-ethyl-6-methyl-phenoxyl-3-(2-methoxy-ethylamino)-propan-2-ol;

(S)-1-(2-amino-ethylamino)-3-{4-[5-(5-diethylaminomethyl-4-methyl-thiophen-2-yl)-[1,2,4]oxadiazol-3-yl]-2-ethyl-6-methyl-phenoxyl-propan-2-ol;

((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propylamino)-acetic acid;

[((S)-3-{4-[5-(5-diethylaminomethyl-4-methyl-thiophen-2-yl)-[1,2,4]oxadiazol-3-yl]-2-ethyl-6-methyl-phenoxyl-2-hydroxy-propyl)-methyl-amino]-acetic acid;

3-((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propylamino)-propionic acid;

N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-3-hydroxy-propionamide;

2-amino-N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-acetamide;

N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-2-methylamino-acetamide;

3-amino-N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-propionamide; and N—((S)-3-{4-[5-(5-diethylaminomethyl-4-methyl-thiophen-2-yl)-[1,2,4]oxadiazol-3-yl]-2-ethyl-6-methyl-phenoxyl-2-hydroxy-propyl)-3-methylamino-propionamide.

The compounds of Formula (I) and their pharmaceutically acceptable salts, can be used as a medicament, e.g. in the form of pharmaceutical compositions for enteral or parenteral administration, and are suitable for decreasing the number of circulating lymphocytes and for the prevention and/or treatment of diseases or disorders associated with an activated immune system.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

Such diseases or disorders associated with an activated immune system and to be prevented/treated with the compounds of Formula (I) are for example selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis;

multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveoretinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with the compounds of Formula (I) are selected from multiple sclerosis and psoriasis The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

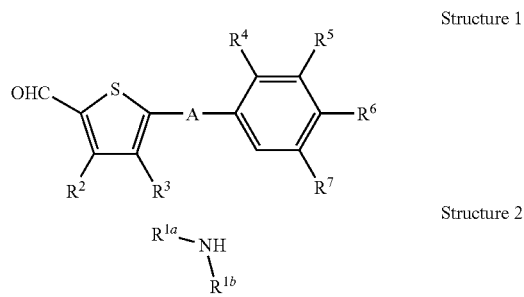

Structure 1

Structure 2

Compounds of the Formula (I) may be prepared by reacting a compound of Structure 1 with a compound of Structure 2 in the presence of a reducing agent such as $NaBH_4$, $NaCNBH_3$, $NaBH(CH_3COO)_3$, $LiBH_4$, etc. in a solvent such as methanol, acetonitrile, 1,2-dichloroethane, dichloromethan, NMP, THF, etc., or mixtures thereof, at temperatures between room temperature and the boiling point of the corresponding solvent (Lit.: e.g. D. H. Boschelli et al., *J. Med. Chem.* 48 (2005) 3891-3902; Abdel-Magid, A. F., *J. Org. Chem.* 61 (1996), 3849-3862). Alternatively, the above mentioned reductive amination step may also be performed using a compound of Structure 1 and a primary amine $R^{1a}$—$NH_2$ or $R^{1b}$—$NH_2$; The second substitutent $R^{1b}$ or $R^{1a}$ may then be introduced by a subsequent alkylation reaction using a compound $R^{1b}$—X and $R^{1a}$—X, respectively, wherein X represents a reactive group such as a halogen atom e.g. chlorine, bromine or iodine. Such an alkylation reaction may be carried out in a solvent such as THF, dioxane, DMF or mixtures thereof, in the presence of a base such as NaH, LiH, LiHMDS, etc. The nature of the substituent $R^6$ influences the choice between the one-step reductive amination or the two step reductive amination-alkylation procedure.

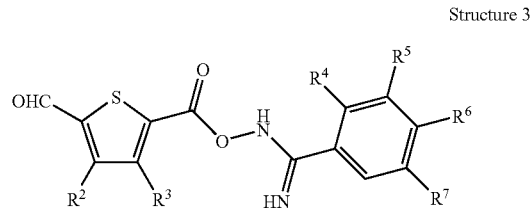

Structure 3

Compounds of Structure 1 which represent a 5-thiophen-2-yl-[1,2,4]oxadiazole derivative, are prepared by reacting a compound of Structure 3 in a solvent such as xylene, toluene, benzene, pyridine, DMF, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, triethylamine, etc.), tetraalkylammonium salts, or water removing agents (e.g. oxalyl chloride, a carboxylic acid anhydride, $POCl_3$, $PCl_5$, $P_4O_{10}$, molecular sieves, etc.) (Lit.: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

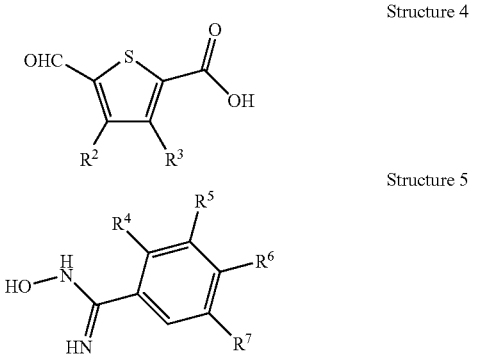

Structure 4

Structure 5

Compounds of Structure 3 may be prepared by reacting a compound of Structure 4 with a compound of Structure 5 in a solvent such as DMF, THF, etc. in the presence of one or more coupling agents such as TBTU, DCC, EDC, HBTU, HOBt, CU, etc. and in the presence or absence of a base such as triethylamine, Hünig's base, NaH, $K_2CO_3$, etc. (Lit.: e.g. A. Hamze, J.-F. Hernandez, P. Fulcrand, J. Martinez, *J. Org. Chem.* 68 (2003) 7316-7321; and the literature cited above).

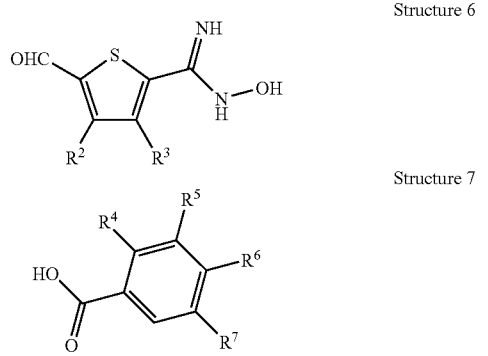

Structure 6

Structure 7

Compounds of Structure 1 which represent a 3-thiophen-2-yl-[1,2,4]oxadiazole derivative are prepared in an analogous fashion (Lit.: e.g. C. T. Brain, J. M. Paul, Y. Loong, P. J. Oakley, *Tetrahedron Lett.* 40 (1999) 3275-3278). Hence, compounds of Structure 1 which represent a 3-thiophen-2-yl-[1,2,4]oxadiazole derivative are prepared by reacting a compound of Structure 6 with a compound of Structure 7.

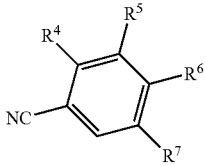

Structure 8

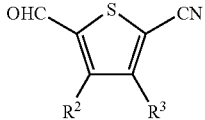

Structure 9

Compounds of Structure 5 and 6 may be prepared by reacting a compound of Structure 8 and 9, respectively, with hydroxylamine or one of its salts in a solvent such as methanol, ethanol, pyridine, etc. in the presence or absence of a base such as $Na_2CO_3$, $K_2CO_3$, triethylamine, etc. (Lit.: e.g. T. Suzuki, K. Iwaoka, N. Imanishi, Y. Nagakura, K. Miyta, H. Nakahara, M. Ohta, T. Mase, *Chem. Pharm. Bull.* 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* 11 (2003), 3379-3392; R. Miller, F. Lang, Z. J. Song, D. Zewge, WO 2004/035538 (Merck & Co., Inc., USA); B. Kaboudin, K. Navaee, *Heterocycles* 60 (2003), 2287-2292). For this step, the aldehyde functionality present in Structure 6 may require temporary protection.

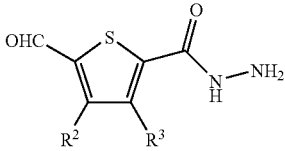

Structure 10

Compounds of Structure 1 which represent a 2-thiophen-2-yl-[1,3,4]oxadiazole or a 2-thiophen-2-yl-[1,3,4]thiadiazole derivative are prepared similarly by reacting a compound of Structure 4 with hydrazine (by using a coupling reagent such as TBTU, DCC, EDC, HBTU, PyBOP, HOBt, CU, etc.) to form a compound of Structure 10 which is then coupled with a compound of Structure 7 to give a compound of Structure 11. The aldehyde functionality present in Structure 4 may require temporary protection during these manipulations. A compound of Structure 11 can also be prepared by following the reverse reaction order, i.e. by first coupling a compound of Structure 7 with hydrazine followed by reacting the corresponding hydrazide intermediate with a compound of Structure 4. Dehydration of a compound of Structure 11 to form the desired 2-thiophen-2-yl-[1,3,4]oxadiazole derivative is affected by treating a compound of Structure 11 with a reagent such as $POCl_3$, $CCl_4$ or $CBr_4$ in combination with triphenylphosphine, $P_2O_5$, Burgess reagent, etc. in a solvent such as toluene, acetonitrile, dioxane, THF, $CHCl_3$, etc. at temperatures between 20 and 120° C. in the presence or absence of microwave irradiation. (Lit.: e.g. M. A. Garcia, S. Martin-Santamaria, M. Cacho, F. Moreno de la Llave, M. Julian, A. Martinez, B. De Pascual-Teresa, A. Ramos, *J. Med. Chem.* 48 (2005) 4068-4075; C. T. Brain, J. M. Paul, Y.

Loong, P. J. Oakley, *Tetrahedron Lett.* 40 (1999) 3275-3278). Likewise, 2-thiophen-2-yl-[1,3,4]thiadiazole derivatives are obtained by cyclising a compound of Structure 11 with Lawesson's reagent, optionally in combination with $P_2S_5$, in the presence or absence of a solvent such as pyridine, toluene, THF, acetonitrile, etc. at elevated temperatures with or without microwave irradiation (Lit.: e.g. A. A. Kiryanov, P. Sampson, A. J. Seed, *J. Org. Chem.* 66 (2001) 7925-7929).

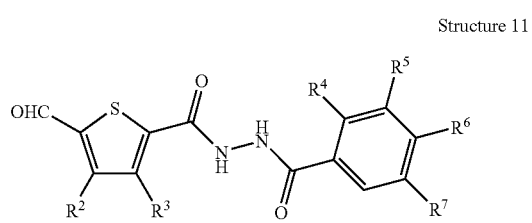

Structure 11

Depending on the nature of the functionalities present in the residues $R^4$ to $R^7$, in particular $R^6$, in Structures 1, 3, 5, 7, 8, and 11, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994). Alternatively, the desired residues $R^4$ to $R^7$, in particular $R^6$, may also be introduced in later steps that follow e.g. the reaction of a compound of Structure 4 or 6 with a suitable precursor of a compound of Structure 5 and 7, respectively. In addition, the desired functionalities in $R^4$ to $R^7$, in particular $R^6$, may also be established after the introduction of the $R^{1a}R^{1b}N$-moiety to the (thienyl)-(phenyl)-oxadiazole or (thienyl)-(phenyl)-thiadiazole scaffolds. The compounds of Structure 5 and 7, or their precursors are either commercially available or are prepared according to procedures known to a person skilled in the art. Procedures that effect the transformation of a carboxylic acid of Structure 4 and 7 into a nitrile of Structure 9 and 8, respectively, are known to a person skilled in the art. Protection of the aldehyde functionality present in Structure 4 may precede the transformation of the acid into the nitrile. The protecting group may be cleaved directly after the transformation or at a later stage as convenient.

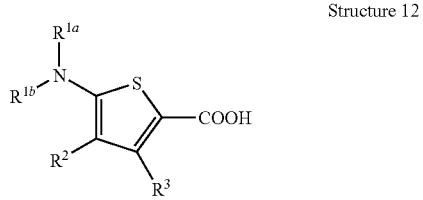

Structure 12

Alternatively, the $R^{1a}R^{1b}N$-moiety may also be introduced to a compound of Structure 4 already to give a compound of Structure 12, which is then used in the following coupling and cyclisation steps to establish the central oxadiazole or thiadiazole ring.

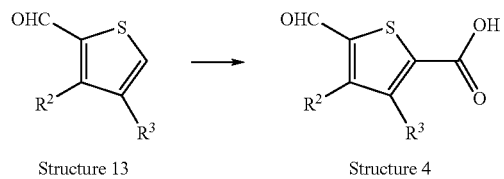

Structure 13      Structure 4

The compounds of Structure 4 can be obtained by reacting a compound of Structure 13 with N,N'-dimethyl-ethylenediamine followed by butyl-lithium and carbon dioxide as described in the literature (e.g. G. Constantino et al., *Il Farmaco* 59 (2004), 93-99; A. J. Carpenter et al., *Tetrahedron* 41 (1985) 3803-3812). The compounds of Structure 13 are either commercially available or can be prepared according to literature procedures (e.g. M. R. Detty et al., *Heterocycles* 40 (1995) 925-937).

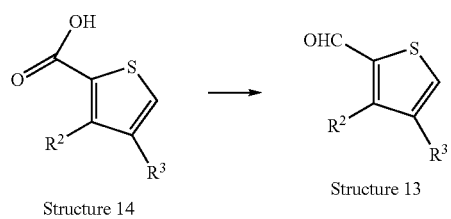

Structure 14      Structure 13

The compounds of Structure 13 may also be obtained from a compound of Structure 14 by transforming the carboxylic acid either directly or via the corresponding alcohol to the aldehyde by methods known to a person skilled in the art. The compounds of Structure 14 are either commercially available or can be prepared in analogy to literature procedures (e.g. T. E. Smith et al., *Heterocycles* 57 (2002) 1211-1217; N. P. Gould, *J. Org. Chem.* 45 (1980) 4528-4530; H. Fiesselmann, German patent application DE 1092929 (1960), Farbwerke Hoechst AG).

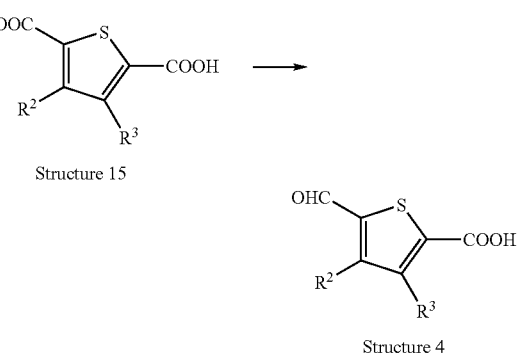

Structure 15

Structure 4

The compounds of Structure 4 may also be prepared by transforming the carboxylic acid ester function of a compound of Structure 15 either directly or via the corresponding alcohol to the aldehyde by methods known to a person skilled in the art. The compounds of Structure 15 can be prepared following procedures described in the literature (e.g. H. Wynberg et al., *J. Org. Chem.* 29 (1964) 1919-1921).

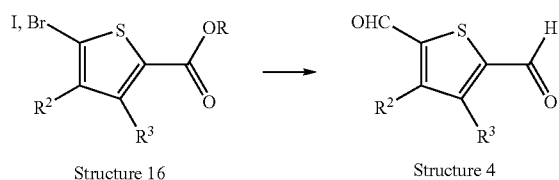

Structure 16 → Structure 4

The compounds of Structure 4 may also be obtained from a compound of Structure 16, wherein R represents a $C_{1-4}$alkyl group such as methyl, ethyl, tert.-butyl, as described in the literature (e.g. I. C. Choong et al., *J. Med. Chem.* 45 (2002) 5005-5022). The compounds of Structure 16 may be prepared in analogy to literature procedures (e.g. Y. Zhang et al., *J. Org. Chem.* 71 (2006) 9475-9483; M. Shilai et al., *J. Chem. Soc. Perkin Trans.* 1, 2001, 442-444).

For the synthesis of a compound of Structure 4 according to the above mentioned procedures, the following starting materials are commercially available: 3-methyl-2-thiophenecarboxaldehyde, 4-methyl-2-thiophenecarboxaldehyde, 3,4-dimethyl-2-thiophenecarboxaldehyde, 3-ethyl-thiophene, methyl 5-bromo-4-methyl-2-thiophene carboxylate, 3-methyl-2-thiophene carboxylic acid methyl ester, 4-methyl-2-thiophene carboxylic acid methyl ester, and 3-ethyl-2-thiophene carboxylic acid.

EXAMPLES

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% acetonitrile in water, 1 min, with 0.04% trifluoroacetic acid, flow: 4.5 mL/min), $t_R$ is given in min; retention times or LC-MS marked with * refer to LC run under basic conditions, i.e. eluting with a gradient of MeCN in water containing 13 mM of ammonium hydroxide, otherwise identical conditions; retention times or LC-MS marked with ** refer to LC run under the following conditions: column: Ascentis express C18, 4.6×30 mm, gradient: 5-95% acetonitrile in water, 1 min, with 0.04% trifluoroacetic acid, flow: 4.5 mL/min; by TLC (TLC-plates from Merck, Silica gel 60 $F_{254}$); or by melting point. Compounds are purified by preparative HPLC (column: X-terra RP18, 50×19 mm, 5 μm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

| Abbreviations (as used herein): | |
|---|---|
| aq. | aqueous |
| atm | atmosphere |
| Boc | tert-butoxycarbonyl |
| BSA | bovine serum albumin |
| CC | column chromatography |
| CDI | carbonyl diimidazole |
| DCC | dicyclohexyl carbodiimide |
| DCM | dichloromethane |
| DEAD | diethyl azodicarboxylate |
| DIPEA | diisopropyl-ethylamine, Hünig's base, ethyl-diisopropylamine |
| DMF | dimethylformamide |
| DMSO | dimethylsulfoxide |
| DPPP | 1,3-bis-(diphenylphosphino)-propane |
| EA | ethyl acetate |
| EDC | N-(3-dimethylaminopropyl)-N'-ethyl-carbodiimide |
| eq. | equivalent(s) |
| Et | ethyl |
| h | hour(s) |
| HBTU | O-(benzotriazol-1-yl)-N,N,N',N'-tetramethyluronium hexafluorophosphate |
| HOBt | 1-hydroxybenzotriazole |
| HPLC | high performance liquid chromatography |
| LC-MS | liquid chromatography-mass spectrometry |
| LiHMDS | lithium 1,1,1,3,3,3-hexamethyl-disilazane |
| Lit. | literature |
| Me | methyl |
| min | minute(s) |
| MPLC | medium pressure liquid chromatography |
| NaOAc | sodium acetate |
| NMP | N-methyl-pyrrolidone |
| OAc | acetate |
| Ph | phenyl |
| prep. | preparative |
| PyBOP | benzotriazol-1-yl-oxy-tris-pyrrolidino-phosphonium-hexafluoro-phosphate |
| rt | room temperature |
| sat. | saturated |
| S1P | sphingosine 1-phosphate |
| TBME | tert. butyl methyl ether |
| TBTU | 2-(1H-benzotriazole-1-yl)-1,2,3,3-tetramethyluronium tetrafluoroborate |
| TFA | trifluoroacetic acid |
| THF | tetrahydrofuran |
| TLC | thin layer chromatography |
| $t_R$ | retention time given in minutes |

5-Formyl-thiophene-2-carboxylic acid

The title compound is commercially available.

5-Formyl-4-methyl-thiophene-2-carboxylic acid

The title compound is prepared according to the procedures described in the literature (G. Constantino et al., *II Farmaco* 59 (2004), 93-99; A. J. Carpenter et al., *Tetrahedron* 41 (1985) 3803-3812); LC-MS: $t_R$=0.70 min, [M+H]$^+$=not detectable, $^1$H NMR (D$_6$-DMSO): δ 2.57 (s, 3H), 7.67 (s, 1H), 10.09 (s, 1H), 13.67 (s br, 1H).

5-Formyl-3,4-dimethyl-thiophene-2-carboxylic acid a) 3,4-Dimethyl-thiophene-2,5-dicarboxylic acid monoethyl ester is prepared according to a literature procedure (H. Wynberg et al., *J. Org. Chem.* 29 (1964) 1919-1921); LC-MS: $t_R$=0.70 min, [M+H]$^+$=not detectable; $^1$H NMR (D$_6$-DMSO): δ 1.26-1.33 (m, 3H), 2.42 (s, 6H), 4.22-4.33 (m, 2H), 12.91 (s br, 1H).

b) To a solution of 3,4-dimethyl-thiophene-2,5-dicarboxylic acid monoethyl ester (6.70 g, 29.4 mmol) in THF (70 mL), a solution of diisobutylaluminium hydride (DIBAL, 90 mL, 1 M in THF) is added at −78° C. The mixture is stirred at −78° C. for 30 min, then at −10° C. for 1 h before another portion of DIBAL (30 mL) is added. Stirring is continued at −10° C. for 30 min. Four more portions of DIBAL (30 mL) are added each time after stirring of the mixture for 30 min at −10° C. The reaction mixture is carefully quenched with water, diluted with 2 N aq. NaOH solution and extracted with DCM.

The organic extracts are disgarded. The aq. phase is acidified by adding 25% aq. HCl and then extracted twice with EA. The organic extracts are washed with brine, dried over MgSO$_4$, filtered, concentrated and dried under high vacuum to give crude 5-hydroxymethyl-3,4-dimethyl-thiophene-2-carboxylic acid (3.00 g) as a brownish solid; LC-MS: $t_R$=0.66 min, [M+H]$^+$=not detectable.

c) A mixture of 5-hydroxymethyl-3,4-dimethyl-thiophene-2-carboxylic acid (3.00 g, 8.06 mmol) and MnO$_2$ (2.55 g, 29.3 mmol) in acetic acid (60 mL) is stirred at 80° C. for 3 h, then at 70° C. for 16 h. The mixture is filtered over Hyflo and the filtrate is concentrated. The crude product is purified by CC on silica gel eluting with DCM containing 10% of methanol. The obtained brownish solid is further purified by suspending the material in acetonitrile and methanol. The solid material is removed by filtration and the filtrate is further purified by prep. HPLC (XBridge Prep C18, 30×75 mm, 5 µm, acetonitrile/water (0.5% HCOOH), 10% to 95% acetonitrile) to give the title compound (435 mg) as a yellow solid; $^1$H NMR (D$_6$-DMSO): δ 2.43 (s br, 6H), 10.16 (s, 1H), 12.35 (s br, 1H).

4-Ethyl-5-formyl-thiophene-2-carboxylic acid a) A solution of 3-ethyl-thiophene (12.14 g, 54.4 mmol) in acetonitrile (60 mL) is cooled to 10° C. before a solution of N-bromo-succinimide (9.31 g, 52.3 mmol) in acetonitrile (90 mL) is added dropwise. The reaction is slightly exothermic. The mixture is stirred and warmed to rt. Another portion of N-bromo-succinimide (2.0 g, 11.2 mmol) dissolved in acetonitrile (40 mL) is added dropwise. Stirring is continued for 2 h before a third portion of N-bromo-succinimide (0.5 g, 2.81 mmol) dissolved in acetonitrile (10 mL) is added. After additional 1 and 2 h, a further portion of N-bromo-succinimide (0.75 g, 4.21 mmol, and 500 mg, 2.81 mmol, respectively) is added. Stirring is continued for another hour before the solvent is evaporated. The residue is dissolved in DCM, washed twice with 2 M aq. NaOH followed by brine, dried over MgSO$_4$, filtered and concentrated. The crude product is purified by distillation at 180° C./50 mbar to give 2-bromo-3-ethyl-thiophene (11.0 g) as a colourless liquid; LC-MS*: $t_R$=0.92 min. $^1$H NMR (CDCl$_3$): δ 1.22 (t, J=7.5 Hz, 3H), 2.62 (q, J=7.8 Hz, 2H), 6.85 (d, J=5.5 Hz, 1H), 7.22 (d, J=5.8 Hz, 1H)

b) A solution of 2-bromo-3-ethyl-thiophene (1.00 g, 5.23 mmol) in THF (25 mL) is cooled to −75° C. before n-butyl lithium (3.6 mL of a 1.6 M solution in THF) is added. The mixture is stirred at −75° C. for 1 h. DMF (765 mg, 10.5 mmol) is added and stirring is continued at −75° C. for 2 h. The mixture is warmed to 10° C., treated with 1 N aq. HCl (5 mL), diluted with water and extracted with EA (3×50 mL). The organic extracts are washed with water (30 mL) followed by brine (30 mL), combined, dried over MgSO$_4$, filtered and concentrated to give crude 3-ethyl-thiophene-2-carbaldehyde (650 mg) as a yellow oil; LC-MS*: $t_R$=0.78 min, $^1$H NMR (CDCl$_3$): δ 1.34 (t, J=7.5 Hz, 3H), 3.03 (q, J=7.5 Hz, 2H), 7.06 (d, J=5.0 Hz, 1H), 7.67 (d, J=5.0 Hz, 1H), 10.08 (s, 1H).

c) The title compound is prepared in analogy to the procedures described in the literature (G. Constantino et al., *Il Farmaco* 59 (2004), 93-99; A. J. Carpenter et al., *Tetrahedron* 41 (1985) 3803-3812) starting from the above 3-ethyl-thiophene-2-carbaldehyde; LC-MS*: $t_R$=0.15 min, [M−1]$^-$=183.16; $^1$H NMR (D$_6$-DMSO): δ1.24 (t, J=7.5 Hz, 3H), 3.00 (q, J=7.5 Hz, 2H), 7.72 (s, 1H), 10.11 (s, 1H).

5-Formyl-N-hydroxy-4-methyl-thiophene-2-carboxamidine a) To a solution of 4-methyl-thiophene-2-carbonitrile (2.70 g, 21.9 mmol) in acetic acid (20 mL), bromine (5.25 g, 32.9 mmol) is added slowly. The mixture is stirred at rt for 1 h then at 40° C. for 3 h and again at rt for 16 h. The mixture is separated by prep. HPLC. The product containing fractions are carefully concentrated at 45° C. and 120 mbar before they are combined, and extracted with EA. The organic extract is dried over Na$_2$SO$_4$, filtered and carefully concentrated and dried to give 5-bromo-4-methyl-thiophene-2-carbonitrile (2.1 g) as a colourless liquid; $^1$H NMR (D$_6$-DMSO): δ2.19 (s, 3H), 7.82 (s, 1H).

b) A solution of 5-bromo-4-methyl-thiophene-2-carbonitrile (1.88 g, 9.30 mmol) in THF (75 mL) is cooled to −75° C. before n-butyl lithium (6.4 mL of a 1.6 m solution in THF, 10.2 mmol) is added. DMF (1.36 g, 18.6 mmol) is added and the mixture is stirred at −78° C. for 30 min and is then warmed to rt. Stirring is continued for 1 h at rt. The reaction is quenched by adding 2 N aq. HCl (10 mL). The solvent is evaporated and the residue is dissolved in EA (500 mL) and washed with sat. aq. NaHCO$_3$ solution followed by water. The washings are extracted back with EA. The organic extracts are combined, dried over Na$_2$SO$_4$, filtered and concentrated. The crude product is purified by prep. HPLC. As above, the product containing fractions are carefully concentrated at 45° C. and 120 mbar before they are combined, and extracted with EA. The organic extract is dried over Na$_2$SO$_4$, filtered and carefully concentrated and dried to give 5-formyl-4-methyl-thiophene-2-carbonitrile (720 mg) as an almost colourless liquid; $^1$H NMR (D$_6$-DMSO): δ 2.58 (s, 3H), 7.96 (s, 1H), 10.11 (s, 1H); $^{13}$C NMR (D$_6$-DMSO): δ 14.10, 114.20, 114.53, 143.04, 143.10, 147.29, 184.82.

c) A solution of 5-formyl-4-methyl-thiophene-2-carbonitrile (720 mg, 4.76 mmol), ethylene glycol (887 mg, 14.3 mmol) and p-toluene sulfonic acid monohydrate (16 mg, 0.095 mmol) in toluene (40 mL) is refluxed in a Dean-Stark apparatus for 2 h. The mixture is cooled to rt, diluted with EA and washed with water. The organic extract is dried over Na$_2$SO$_4$, filtered and concentrated to give 5-[1,3]dioxolan-2-yl-4-methyl-thiophene-2-carbonitrile (990 mg) as an almost colourless oil; $^1$H NMR (D$_6$-DMSO): δ2.25 (s, 3H), 3.95-4.08 (m, 4H), 6.16 (s, 1H), 7.76 (s, 1H).

d) To a solution of 5-[1,3]dioxolan-2-yl-4-methyl-thiophene-2-carbonitrile (990 mg, 5.07 mmol) in ethanol (50 mL), triethylamine (2.05 g, 20.3 mmol) followed by hydroxylamine hydrochloride (705 mg, 10.14 mmol) is added. The mixture is stirred at rt for 16 h. The solvent is evaporated, the residue is dissolved in water and is then separated by prep. HPLC (XBridge 50×50 +50×100 mm, eluting with a gradient of acetonitrile in water containing 0.5% of ammonia) to give N-[amino-(5-[1,3]dioxolan-2-yl-4-methyl-thiophen-2-yl)-methyl]-hydroxylamine (510 mg) as an off-white solid; LC-MS*: $t_R$=0.60 min, [M+1]$^+$=229.11.

e) To a suspension of N-[amino-(5-[1,3]dioxolan-2-yl-4-methyl-thiophen-2-yl)-methyl]-hydroxylamine (510 mg, 2.23 mmol) in water (10 mL) and acetonitrile (10 mL), 1 N aq. HCl (1 mL) is added. The now clear solution is stirred at rt for 10 min before another portion of 1 N aq HCl (1 mL) is added. Stirring is continued for 10 min. The reaction mixture is basified by adding 25% aq. ammonia solution and is then separated by prep. HPLC (XBridge 50×50 +50×100 mm, eluting with a gradient of acetonitrile in water containing 0.5% of ammonia) to give the title compound (407 mg) as a yellow solid; LC-MS*: $t_R$=0.55 min, [M+1]$^+$=185.16; $^1$H NMR (D$_6$-DMSO): δ2.53 (s, 3H), 6.06 (s br, 2H), 7.44 (s, 1H), 10.00 (s, 1H), 10.06 (s, 1H).

5-[1,3]Dioxolan-2-yl-4-methyl-thiophene-2-carboxylic acid hydrazide a) A suspension of 5-formyl-4-methyl-thiophene-2-carboxylic acid (3.00 g, 17.6 mmol), ethylene glycol (3.28 g, 52.9 mmol) and p-toluene sulfonic acid hydrate (61 mg, 0.353 mmol) in toluene (80 mL) is refluxed for 3 h in a Dean-Stark apparatus. The clear solution is diluted with EA and washed twice with water. The washings are extracted back with EA. The combined organic extracts are dried over $Na_2SO_4$, filtered, concentrated and dried to give 5-[1,3]dioxolan-2-yl-4-methyl-thiophene-2-carboxylic acid (3.69 g) as a pale yellow resin, LC-MS: $t_R$=0.46 min, $[M+1]^+$=215.15.

b) To a mixture of 5-[1,3]dioxolan-2-yl-4-methyl-thiophene-2-carboxylic acid (3.00 g, 14.0 mmol), HOBt (2.52 g, 16.8 mmol) and EDC (2.95 g, 15.4 mmol) in isopropanol (240 mL), hydrazine hydrate (1.50 g, 29.4 mmol) is added at 0° C. The suspension is stirred at 0° C., diluted with DMF and warmed to rt. Stirring is continued at rt for 2 h before the solvent is evaporated. The residue is dissolved in acetonitrile and separated by prep. HPLC (XBridge C18, 50×50 +100×50 mm, 10 μm, gradient of acetonitrile in water containing 0.5% of aq. ammonia) to give the title compound (2.43 g) as a colourless solid; LC-MS: $t_R$=0.57 min, $[M+1]^+$=228.96; $^1$H NMR ($D_6$-DMSO): δ2.20 (s, 3H), 3.90-3.99 (m, 2H), 3.99-4.08 (m, 2H), 4.43 (s, 2H), 6.06 (s, 1H), 7.43 (s, 1H), 9.69 (s, 1H).

5-Diethylaminomethyl-4-methyl-thiophene-2-carboxylic acid

To a solution of 5-formyl-4-methyl-thiophene-2-carboxylic acid (6.90 g, 40.5 mmol) in THF (150 mL), diethylamine (5.93 g, 81.1 mmol) and acetic acid (10 mL) followed by sodium triacetoxyborohydride (14.32 g, 60.8 mmol) is added. The mixture becomes slightly warm. The reaction mixture is stirred at rt for 16 h before it is concentrated and separated by CC on silica gel eluting with EA containing 0-50% of methanol to give the title compound (4.95 g) containing large amount of diethylammonium salts. The material (4.94 g, 21.8 mmol) is therefore dissolved in methanol (70 mL) and treated with chloro trimethylsilane (23.7 g, 218 mmol). The mixture is stirred at 50° C. for 18 h before it is concentrated, dissolved in EA and washed with sat. aq. $NaHCO_3$ solution. The organic extract is dried over $Na_2SO_4$, filtered, concentrated and dried to give 5-diethylaminomethyl-4-methyl-thiophene-2-carboxylic acid methyl ester (4.05 g) as a yellow oil; $^1$H NMR ($CDCl_3$): δ 1.08 (t, J=7.0 Hz, 6H), 2.19 (s, 3H), 2.59 (q, J=7.0 Hz, 4H), 3.67 (s, 2H), 3.87 (s, 3H), 7.28 (s, 1H), 7.52 (s, 1H). This material is dissolved in 1 N aq. HCl (80 mL) and stirred at 65° C. for 214 h. The solvent is evaporated and the residue is dried under high vacuum to give the title compound (3.56 g) as a pale beige solid; LC-MS: $t_R$=0.26 min; $[M+1]^+$=228.20; $^1$H NMR ($D_6$-DMSO): δ 1.28 (t, J=7.3 Hz, 6H), 2.31 (s, 3H), 3.12 (q, J=6.8 Hz, 4H), 4.48 (s, 2H), 7.59 (s, 1H).

3-Ethyl-4-hydroxy-5-methyl-benzonitrile

The title compound is prepared from 3-ethyl-4-hydroxy-5-methyl-benzaldehyde following literature procedures (A. K. Chakraborti, G. Kaur, *Tetrahedron* 55 (1999) 13265-13268); LC-MS: $t_R$=0.90 min; $^1$H NMR ($CDCl_3$): δ 1.24 (t, J=7.6 Hz, 3H), 2.26 (s, 3H), 2.63 (q, J=7.6 Hz, 2H), 5.19 (s, 1H), 7.30 (s, 2H).

3-Chloro-4-hydroxy-5-methyl-benzonitrile

The title compound is prepared from commercially available 2-chloro-6-methyl-phenol in analogy to literature procedures (see 3-ethyl-4-hydroxy-5-methyl-benzonitrile); LC-MS: $t_R$=0.85 min. $^1$H NMR ($CDCl_3$): δ 2.33 (s, 3H), 6.10 (s, 1H), 7.38 (s, 1H), 7.53 (d, J=1.8 Hz, 1H).

4-Hydroxy-3-methoxy-5-methyl-benzonitrile

The title compound is prepared from commercially available 2-hydroxy-3-methoxy-toluene in analogy to literature procedures (see 3-ethyl-4-hydroxy-5-methyl-benzonitrile); LC-MS: $t_R$=0.84 min. $^1$H NMR ($CDCl_3$): δ 2.27 (s, 3H), 3.93 (s, 3H), 6.24 (s, 1H), 6.97 (d, J=1.3 Hz, 1H), 7.12 (s, 1H).

4-Hydroxy-2-methoxy-benzonitrile

The title compound is prepared from commercially available 4-hydroxy-2-methoxy-benzaldehyde in analogy to literature procedures (see 3-ethyl-4-hydroxy-5-methyl-benzonitrile); LC-MS: $t_R$=0.74 min. $^1$H NMR ($D_6$-DMSO): δ 3.84 (s, 3H), 6.47 (d, J=8.5 Hz, 1H), 6.54 (s, 1H), 7.49 (d, J=8.5 Hz, 1H), 10.6 (s, 1H).

4-Hydroxy-2-methyl-benzonitrile

A solution of 4-methoxy-2-methylbenzonitrile (5.0 g, 33.97 mmol) in DCM (150 mL) is cooled down to 0° C. before adding dropwise a 1M $BBr_3$ in DCM solution (136 mL, 136 mmol). The reaction mixture is allowed to reach rt and stirring is then continued at 45° C. for 5 days. Ice water (500 mL) is then added and the reaction mixture is stirred for 1 h before sat. aq. $NaHCO_3$ (250 mL) is added. The mixture is extracted with DCM (200 mL then 4×100 mL) and the combined organic extracts are dried over $MgSO_4$, filtered and evaporated to give the title compound as a brown solid (4.7 g); LC-MS: $t_R$=0.76 min. $^1$H NMR ($D_6$-DMSO): δ 2.38 (s, 3H), 6.73 (dd, J=8.5, 2.0 Hz, 1H), 6.79 (d, J=2.0 Hz, 1H), 7.55 (d, J=8.5 Hz, 1H), 10.49 (s, 1H).

4,N-Dihydroxy-3,5-dimethyl-benzamidine

The title compound is prepared from commercially available 4-hydroxy-3,5-dimethyl-benzonitrile according to literature procedures (e.g. E. Meyer, A. C. Joussef, H. Gallardo, *Synthesis* 2003, 899-905); $^1$H NMR ($CD_3OD$): δ 7.20 (s, 2H), 2.20 (s, 6H).

3-Ethyl-4,N-dihydroxy-5-methyl-benzamidine

The title compound is prepared from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); LC-MS: $t_R$=0.55 min; $^1$H NMR ($D_6$-DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

4,N-Dihydroxy-3-methyl-5-propyl-benzamidine

The title compound is prepared from commercially available 2-methyl-6-propyl-phenol in analogy to literature procedures (e.g B. Roth et al. *J. Med. Chem.* 31 (1988) 122-129; and literature cited for 3-ethyl-4,N-dihydroxy-5-methyl-benzamidine); LC-MS: $t_R$=0.54 min; $[M+1]^+$=209.43; $^1$H NMR ($D_6$-DMSO): δ0.90 (t, J=7.3 Hz, 3H), 1.48-1.59 (m, 3H), 2.19 (s, 3H), 2.56 (t, J=7.3 Hz, 2H), 7.37 (s, 1H), 7.40 (s, 1H), 9.34 (s, 1H).

3-Chloro-4,N-dihydroxy-5-methyl-benzamidine

The title compound is prepared from commercially available 2-chloro-6-methyl-phenol in analogy to literature procedures (e.g B. Roth et al. *J. Med. Chem.* 31 (1988) 122-129; and literature cited for 3-ethyl-4,N-dihydroxy-5-methyl-benzamidine); 3-chloro-4-hydroxy-5-methyl-benzaldehyde: LC-MS: $t_R$=0.49 min; [M+1]$^+$=201.00; $^1$H NMR δ2.24 (s, 2H), 2.35 (s, 4H), 5.98 (s br, 1H), 7.59 (d, J=1.8 Hz, 1H), 7.73 (d, J=1.8 Hz, 1H), 9.80 (s, 1H); 3-chloro-4,N-dihydroxy-5-methyl-benzamidine: $^1$H NMR (D$_6$-DMSO): δ2.21 (s, 3H), 5.72 (s br, 2H), 7.40 (s, 1H), 7.48 (s, 1H), 9.29 (s br, 1H), 9.48 (s br, 1H).

4,N-Dihydroxy-3-methoxy-5-methyl-benzamidine

The title compound is prepared from commercially available 2-methoxy-6-methyl-phenol in analogy to literature procedures (e.g B. Roth et al. *J. Med. Chem.* 31 (1988) 122-129; and literature cited for 3-ethyl-4,N-dihydroxy-5-methyl-benzamidine); LC-MS: $t_R$=0.50 min; [M+1]$^+$=197.23.

4,N-Dihydroxy-2-methoxy-benzamidine

The title compound is prepared from commercially available 4-hydroxy-2-methoxybenzaldehyde in analogy to literature procedures (see 3-ethyl-4,N-dihydroxy-5-methyl-benzamidine); LC-MS: $t_R$=0.41 min; [M+1]$^+$=183.06; $^1$H NMR (D$_6$-DMSO): δ3.74 (s, 3H), 5.47 (s, 2H), 6.35 (dd, J=8.3, 1.5 Hz, 1H), 6.45 (s, 1H), 7.21 (d, J=8.5 Hz, 1H), 9.42 (s, 2H).

3-[4-(N-Hydroxycarbamimidoyl)-2,6-dimethyl-phenyl]-propionic acid

The title compound is prepared in analogy to 3-[2-ethyl-4-(N-hydroxycarbamimidoyl)-6-methyl-phenyl]-propionic acid starting from 3,5-dimethyl-4-hydroxybenzaldehyde; LC-MS: $t_R$=0.57 min, [M+1]$^+$=237.02; $^1$H NMR (D$_6$-DMSO): δ2.29 (s, 6H), 2.30-2.36 (m, 2H), 2.80-2.87 (m, 2H), 5.66 (s, 2H), 7.30 (s, 2H), 9.46 (s, 1H).

3-[2-Ethyl-4-(N-hydroxycarbamimidoyl)-6-methyl-phenyl]-propionic acid a) To an ice-cooled solution of 5-ethyl-4-hydroxy-3-methyl-benzaldehyde (10.0 g, 60.9 mmol) in DCM (50 mL) and pyridine (15 mL), trifluoromethanesulfonic acid anhydride (18.9 g, 67 mmol) is added over a period of 20 min. Upon complete addition, the ice bath is removed and the reaction is stirred for further 2 h at rt. The mixture is diluted with DCM (150 mL), washed three times with water, dried over MgSO$_4$, filtered and evaporated. The residue is purified by flash chromatography on silica gel eluting with heptane:EA 9:1 to give trifluoro-methanesulfonic acid 2-ethyl-4-formyl-6-methyl-phenyl ester (10.75 g) as a pale yellow oil; LC-MS: $t_R$=1.07 min; $^1$H NMR (CDCl$_3$): δ 9.98 (s, 1H), 7.70 (s, 1H), 7.66 (s, 1H), 2.85 (q, J=10.1 Hz, 2H), 2.48 (s, 3H), 1.30 (t, J=10.2 Hz, 3H).
b) To a stirred solution of the above triflate (10.7 g, 36.1 mmol) in dry DMF (75 mL) is sequentially added triethylamine (7.3 g, 72.2 mmol), methyl acrylate (31.1 g, 361 mmol), DPPP (819 mg, 1.99 mmol) and Pd(OAc)$_2$ (405 mg, 1.81 mmol) under nitrogen. The mixture is stirred at 115° C. for 5 h, cooled to rt, diluted with diethyl ether (350 mL) and washed twice with 1 N aq. HCl and once with sat. aq. NaHCO$_3$ solution. The organic extract is dried over MgSO$_4$, filtered and evaporated. The residue is purified by flash chromatography on silica gel eluting with heptane:EA 19:1 to give 3-(2-ethyl-4-formyl-6-methyl-phenyl)-acrylic acid methyl ester (5.93 g) as a colourless liquid; LC-MS: $t_R$=0.99 min.
c) A suspension of 3-(2-ethyl-4-formyl-6-methyl-phenyl)-acrylic acid methyl ester (5.93 g, 25.53 mmol) in methanol (140 mL) and 2 N aq. NaOH (45 mL) is stirred at rt for 1 h. The methanol is evaporated and the aq. solution is extracted twice with DCM. The aq. layer is acidified with 37% aq. HCl. The precipitate that forms is collected, washed with water and dried. The product is further purified by recrystallisation from EA (100 mL) to give 3-(2-ethyl-4-formyl-6-methyl-phenyl)-acrylic acid (4.2 g) as yellow crystals; LC-MS: $t_R$=0.87 min.
d) To a solution of 3-(2-ethyl-4-formyl-6-methyl-phenyl)-acrylic acid (2.75 g, 12.6 mmol) and DIPEA (1.8 g, 13.8 mmol) in ethanol (80 mL), Pd/C (275 mg, 10% Pd, moistened with 50% water) is added. The mixture is stirred for 16 h at rt under 1 atm of H$_2$. The catalyst is filtered off and the filtrate is concentrated. The residue is dissolved in EA, washed with 2 N aq. HCl, followed by 1 N aq. HCl and brine. The organic extract is dried over Na$_2$SO$_4$, filtered and evaporated to give 3-(2-ethyl-4-hydroxymethyl-6-methyl-phenyl)-propionic acid (2.8 g) as a white solid; LC-MS: $t_R$=0.76 min.
e) A solution of 3-(2-ethyl-4-hydroxymethyl-6-methyl-phenyl)-propionic acid (2.8 g, 12.6 mmol) in acetic acid (50 mL) is treated with MnO$_2$ (3.9 g, 45.4 mmol) and the resulting mixture is stirred at 80° C. for 4 h. The mixture is filtered and the filtrate is concentrated. The crude product is purified by CC on silica gel eluting with DCM to give 3-(2-ethyl-4-formyl-6-methyl-phenyl)-propionic acid (1.76 g) as a beige solid; LC-MS: $t_R$=0.86 min.
f) A solution of 3-(2-ethyl-4-formyl-6-methyl-phenyl)-propionic acid (1.67 g, 7.58 mmol) and hydroxylamine hydrochloride (780 mg, 11.36 mmol) in 1-methyl-2-pyrrolidone is heated to 80° C. for 30 min in the microwave (300 W, active cooling during irradiation). The reaction mixture is diluted with diethyl ether and washed with water and brine. The organic extract is dried over Na$_2$SO$_4$, filtered and evaporated to give 3-(4-cyano-2-ethyl-6-methyl-phenyl)-propionic acid (1.55 g) as a beige solid; LC-MS: $t_R$=0.89 min, $^1$H NMR (D$_6$-DMSO): δ 12.25 (s, 1H), 7.45 (s, 2H), 2.91-2.84 (m, 2H), 2.67-2.59 (m, 2H), 2.35-2.30 (m, 5H), 1.14 (t, J=7.6 Hz, 3H).
g) Potassium tert. butoxide (2.71 g, 24.1 mmol) is carefully dissolved in methanol (25 mL). To this solution hydroxylamine hydrochloride (1.44 g, 20.7 mmol) followed by 3-(4-cyano-2-ethyl-6-methyl-phenyl)-propionic acid (1.50 g, 6.90 mmol) dissolved in methanol (7.5 mL) is added. The mixture is refluxed for 8 h and the solvent is evaporated. The residue is dissolved in 2 N aq. HCl and extracted with EA. The pH of the aq. phase is adjusted to pH 5 by adding sat. aq. NaHCO$_3$ and the mixture is extracted three times with EA. The combined organic extracts are dried over Na$_2$SO$_4$, filtered, evaporated and dried to give 3-[2-ethyl-4-(N-hydroxycarbamimidoyl)-6-methyl-phenyl]-propionic acid (1.4 g) as a white solid; LC-MS: $t_R$=0.60 min, [M+1]$^+$=251.17.

4-Bromo-2-ethyl-6-methyl-aniline

The title compound is prepared from commercially available 2-ethyl-6-methyl-aniline following literature procedures (R. A. Benkeser, R. A. Hickner, D. I. Hoke, O. H. Thomas *J. Am. Chem. Soc.* 80 (1958) 5289-5293); $^1$H NMR (CDCl$_3$): δ 1.27 (t, J=7.3 Hz, 3H), 2.18 (s, 3H), 2.51 (q, J 7.3 Hz, 2H), 3.61 (s br, 2H), 7.09 (s, 2H).

4-Amino-3-ethyl-5-methyl-benzonitrile

The title compound is prepared from 4-bromo-2-ethyl-6-methyl-aniline following literature procedures (J. Zanon, A.

Klapars, S. Buchwald *J. Am. Chem. Soc.* 125 (2003) 2890-2891); $^1$H NMR (CDCl$_3$): δ 1.29 (t, J 7.5 Hz, 3H), 2.19 (s, 3H), 2.52 (q, J 7.5 Hz, 2H), 4.10 (s br, 2H), 7.25 (s br, 2H).

4-Bromo-3-ethyl-5-methyl-benzonitrile

The title compound is prepared from 4-amino-3-ethyl-5-methyl-benzonitrile and copper(II) bromide following literature procedures (M. P. Doyle, B. Siegfried, J. F. Dellaria Jr., *J. Org. Chem.* 42 (1977) 2426-2429); $^1$H NMR (CDCl$_3$): δ 1.26 (t, J 7.5 Hz, 3H), 2.47 (s, 3H), 2.83 (q, J 7.5 Hz, 2H), 7.36 (s, 1H), 7.37 (s, 1H).

3-(4-Cyano-2-ethyl-6-methyl-phenyl)-propionic acid ethyl ester

The title compound is prepared from 4-bromo-3-ethyl-5-methyl-benzonitrile and commercially available acrolein diethyl acetal following literature procedures (G. Battistuzzi, S. Cacchi, G. Fabrizi, R. Bernini, *Synlett* 8 (2003) 1133-1136); LC-MS: $t_R$=0.91 min; $^1$H NMR (CDCl$_3$): δ 1.2 (m, 6H), 2.38 (s, 3H), 2.44 (m, 2H), 2.70 (q, J 7.5 Hz, 2H), 3.03 (m, 2H), 4.18 (q, J 7.3 Hz, 2H), 7.30 (s, 1H), 7.34 (s, 1H).

3-[2-Ethyl-4-(N-hydroxycarbamimidoyl)-6-methyl-phenyl]-propionic acid ethyl ester 3-(4-Cyano-2-ethyl-6-methyl-phenyl)-propionic acid ethyl ester is transformed to the corresponding hydroxyamidine according to literature procedures using triethylamine as base (e.g. E. Meyer, A. C. Joussef, H. Gallardo, *Synthesis* 2003, 899-905); LC-MS: $t_R$=0.77 min; [M+1]$^+$=279.52; $^1$H NMR (D$_6$-DMSO): δ 1.19 (m, 6H), 2.29 (s, 3H), 2.41 (m, 2H), 2.62 (q, J 7.5 Hz, 2H), 2.88 (m, 2H), 4.09 (q, J 7.0 Hz, 2H), 5.68 (s br, 2H), 7.31 (s, 1H), 7.33 (s, 1H), 9.47 (s, 1H).

4-(N-Hydroxycarbamimidoyl)-benzoic acid ethyl ester

The title compound is prepared in analogy to 4,N-dihydroxy-3,5-dimethyl-benzamidine starting from ethyl 4-cyanobenzoate; LC-MS: $t_R$=0.55 min, [M+1]$^+$=209.05; $^1$H NMR (D$_6$-DMSO): δ 1.33 (t, J=7.0 Hz, 3H), 4.32 (q, J=7.0 Hz, 2H), 5.94 (s, 2H), 7.83 (d, J=8.0 Hz, 2H), 7.95 (d, J=7.8 Hz, 2H), 9.91 (s, 1H).

rac-4-(2,2-Dimethyl-[1,3]dioxolan-4-ylmethoxy)-N-hydroxy-3,5-dimethyl-benzamidine a) To a solution of 3,5-dimethyl-4-hydroxy-benzonitrile (5.0 g, 34.0 mmol) in THF (40 mL), rac-(2,2-dimethyl-[1,3]dioxolan-4-yl)-methanol (4.49 g, 34.0 mmol) followed by triphenylphosphine (13.4 g, 50.9 mmol) is added. The mixture is cooled with an ice-bath before DEAD (8.87 g, 50.9 mmol, 23.4 mL of a 40% solution in toluene) is added dropwise. The mixture is stirred at rt for 1 h, the solvent is removed in vacuo and the residue is purified by CC on silica gel eluting with heptane:EA 99:1 to 92:8 to give rac-4-(2,2-dimethyl-[1,3]dioxolan-4-ylmethoxy)-3,5-dimethyl-benzonitrile (7.20 g) as a pale yellow oil; LC-MS: $t_R$=0.99 min, [M+1]$^+$=not detected.
b) To a solution of potassium tert.-butylate (6.18 g, 55.1 mmol) in methanol (125 mL), hydroxylamine hydrochloride (5.74 g, 82.7 mmol) is added. To this solution, a solution of rac-4-(2,2-dimethyl-[1,3]dioxolan-4-ylmethoxy)-3,5-dimethyl-benzonitrile (7.20 g, 27.6 mmol) in methanol (40 mL) is added. The mixture is refluxed for 72 h before the solvent is removed in vacuo. The residue is purified by prep. HPLC (XBridge Prep C18, 30×75 mm, 5 μm, 2-95% acetonitrile in water containing 0.5% sat. aq. NH$_3$) to give the title compound (4.85 g) as a pale yellow solid; LC-MS: $t_R$=0.67 min, [M+1]$^+$=295.06; $^1$H NMR (CDCl$_3$): δ1.43 (s, 3H), 1.48 (s, 3H), 2.29 (s, 6H), 3.76-3.81 (m, 1H), 3.83-3.88 (m, 1H), 3.93-3.99 (m, 1H), 4.17-4.23 (m, 1H), 4.47-4.54 (m, 1H), 5.02 (s br, 1H), 7.28 (s, 2H).

(S)-4-(2,2-Dimethyl-[1,3]dioxolan-4-ylmethoxy)-3-ethyl-N-hydroxy-5-methyl-benzamidine The title compound is prepared in analogy to rac-4-(2,2-dimethyl-[1,3]dioxolan-4-yl methoxy)-N-hydroxy-3,5-dimethyl-benzamidine from 3-ethyl-4-hydroxy-5-methyl-benzonitrile and (S)-(2,2-dimethyl-[1,3]dioxolan-4-yl)methanol; LC-MS*: $t_R$=0.97 min.

(R)-3-Chloro-4-(2,2-dimethyl-[1,3]dioxolan-4-ylmethoxy)-N-hydroxy-5-methyl-benzamidine The title compound is obtained as a colorless oil (1.39 g) in analogy to rac-4-(2,2-dimethyl-[1,3]dioxolan-4-ylmethoxy)-N-hydroxy-3,5-dimethyl-benzamidine starting from 3-chloro-4-hydroxy-5-methyl-benzonitrile and L-alpha-beta-isopropyliden glycerol; LC-MS: $t_R$=0.66 min, [M+H]$^+$=314.96.

(R)-4-(2,2-Dimethyl-[1,3]dioxolan-4-ylmethoxy)-N-hydroxy-3-methoxy-5-methyl-benzamidine The title compound is obtained as a beige oil (1.16 g) in analogy to rac-4-(2,2-dimethyl-[1,3]dioxolan-4-ylmethoxy)-N-hydroxy-3,5-dimethyl-benzamidine starting from 4-hydroxy-3-methoxy-5-methyl-benzonitrile and L-alpha-beta-isopropyliden glycerol; LC-MS: $t_R$=0.65 min, [M+H]$^+$=311.0.

(R)-4-(2,2-Dimethyl-[1,3]dioxolan-4-ylmethoxy)-N-hydroxy-2-methoxy-benzamidine

The title compound is obtained as a beige oil (2.46 g) in analogy to rac-4-(2,2-dimethyl-[1,3]dioxolan-4-ylmethoxy)-N-hydroxy-3,5-dimethyl-benzamidine starting from 4-hydroxy-2-methoxy-benzonitrile and L-alpha-beta-isopropyliden glycerol; LC-MS: $t_R$=0.62 min, [M+H]$^+$=296.97.

rac-2-Hydroxy-N-{2-hydroxy-3-[4-(N-hydroxycarbamimidoyl)-2,6-dimethyl-phenoxy]-propyl}-acetamide The title compound is prepared in analogy to N—((S)-3-[2-ethyl-4-(N-hydroxycarbamimidoyl)-6-methyl-phenoxy]-2-hydroxy-propyl)-2-hydroxy-acetamide; LC-MS: $t_R$=0.48 min, [M+1]$^+$=312.05; $^1$H NMR (D$_6$-DMSO): δ2.21 (s, 6H), 3.14-3.25 (m, 1H), 3.35-3.46 (m, 1H), 3.60-3.69 (m, 2H), 3.80 (s, 2H), 3.85-3.94 (m, 1H), 5.69 (s br, 2H), 7.30 (s, 2H), 7.63 (t, J=5.6 Hz, 1H), 8.11 (s, 1H).

(S)-2-Hydroxy-N-{2-hydroxy-3-[4-(N-hydroxycarbamimidoyl)-2,6-dimethyl-phenoxy]-propyl}-acetamide The title compound is prepared in analogy to N—((S)-3-[2-ethyl-4-(N-hydroxycarbamimidoyl)-6-methyl-phenoxy]-2-hydroxy-propyl)-2-hydroxy-acetamide; LC-MS: $t_R$=0.23 min, [M+1]$^+$=312.25.

(S)—N-(3-[2-Chloro-4-(N-hydroxycarbamimidoyl)-6-methyl-phenoxy]-2-hydroxy-propyl)-2-hydroxy-acetamide The title compound is obtained as a beige wax (1.1 g) in analogy to N—((S)-3-[2-ethyl-4-(N-hydroxycarbamimidoyl)-6-methyl-phenoxy]-2-hydroxy-propyl)-2-hydroxy-acetamide starting from 3-chloro-4-hydroxy-5-methyl-benzonitrile; LC-MS: $t_R$=0.48 min, $[M+H]^+$=331.94.

(S)-2-Hydroxy-N-(2-hydroxy-3-[4-(N-hydroxycarbamimidoyl)-3-methyl-phenoxy]-propyl)-acetamide The title compound is obtained as a beige oil (1.0 g) in analogy to N—((S)-3-[2-ethyl-4-(N-hydroxycarbamimidoyl)-6-methyl-phenoxy]-2-hydroxy-propyl)-2-hydroxy-acetamide starting from 4-hydroxy-2-methyl-benzonitrile; LC-MS: $t_R$=0.35 min, $[M+H]^+$=297.99.

(S)-2-Hydroxy-N-(2-hydroxy-3-[4-(N-hydroxycarbamimidoyl)-2-methoxy-6-methyl-phenoxy]-propyl)-acetamide The title compound is obtained as a reddish oil (1.3 g) in analogy to N—((S)-3-[2-ethyl-4-(N-hydroxycarbamimidoyl)-6-methyl-phenoxy]-2-hydroxy-propyl)-2-hydroxy-acetamide starting from 4-hydroxy-3-methoxy-5-methyl-benzonitrile; LC-MS: $t_R$=0.49 min, $[M+H]^+$=327.98.

(S)-4-(3-Amino-2-hydroxypropoxy)-3-ethyl-5-methylbenzonitrile a) To a solution of 3-ethyl-4-hydroxy-5-methyl-benzonitrile (5.06 g, 31.4 mmol) in THF (80 mL), $PPh_3$ (9.06 g, 34.5 mmol) and (R)-glycidol (2.29 mL, 34.5 mmol) are added. The mixture is cooled to 0° C. before DEAD in toluene (15.8 mL, 34.5 mmol) is added. The mixture is stirred for 18 h while warming up to rt. The solvent is evaporated and the crude product is purified by CC on silica gel eluting with heptane:EA 7:3 to give 3-ethyl-5-methyl-4-oxiranylmethoxy-benzonitrile (5.85 g) as a yellow oil; LC-MS: $t_R$=0.96 min; $[M+42]^+$=259.08.
b) The above epoxide is dissolved in 7 N $NH_3$ in methanol (250 mL) and the solution is stirred at 65° C. for 18 h. The solvent is evaporated to give crude (S)-4-(3-amino-2-hydroxypropoxy)-3-ethyl-5-methylbenzonitrile (6.23 g) as a yellow oil; LC-MS: $t_R$=0.66 min; $[M+1]^+$=235.11.

N—((S)-3-[2-Ethyl-4-(N-hydroxycarbamimidoyl)-6-methyl-phenoxy]-2-hydroxy-propyl)-2-hydroxy-acetamide a) To a solution of (S)-4-(3-amino-2-hydroxypropoxy)-3-ethyl-5-methylbenzonitrile (6.23 g, 26.59 mmol), glycolic acid (2.43 g, 31.9 mmol), HOBt (4.31 g, 31.9 mmol), and EDC hydrochloride (6.12 g, 31.9 mmol) are added. The mixture is stirred at rt for 18 h before it is diluted with sat. aq. $NaHCO_3$ and extracted twice with EA. The combined organic extracts are dried over $MgSO_4$, filtered and concentrated. The crude product is purified by CC with DCM containing 8% of methanol to give (S)—N-[3-(4-cyano-2-ethyl-6-methyl-phenoxy)-2-hydroxy-propyl]-2-hydroxy-acetamide (7.03 g) as a yellow oil; LC-MS: $t_R$=0.74 min; $[M+1]^+$=293.10; $^1$H NMR ($CDCl_3$): δ 1.25 (t, J=7.5 Hz, 3H), 2.32 (s, 3H), 2.69 (q, J=7.5 Hz, 2H), 3.48-3.56 (m, 3H), 3.70-3.90 (m, 3H), 4.19 (s, br, 3H), 7.06 (m, 1H), 7.36 (s, 1H), 7.38 (s, 1H).

b) The above nitrile is converted to the N-hydroxy-benzamidine according to literature procedures (e.g. E. Meyer, A. C. Joussef, H. Gallardo, *Synthesis* 2003, 899-905); LC-MS: $t_R$=0.51 min; $[M+1]^+$=326.13; $^1$H NMR ($D_6$-DMSO): δ 1.17 (t, J 7.4 Hz, 3H), 2.24 (s, 3H), 2.62 (q, J 7.4 Hz, 2H), 3.23 (m, 1H), 3.43 (m, 1H), 3.67 (m, 2H), 3.83 (s, 2H), 3.93 (m, 1H), 5.27 (s br, 1H), 5.58 (s br, 1H), 5.70 (s, 2H), 7.34 (s, 1H), 7.36 (s, 1H), 7.67 (m, 1H), 9.46 (s br, 1H).

N-Hydroxy-4-hydroxymethyl-benzamidine

The title compound is prepared in analogy to rac-4-(2,2-dimethyl-[1,3]dioxolan-4-ylmethoxy)-N-hydroxy-3,5-dimethyl-benzamidine (step b) starting from 4-hydroxymethyl-benzonitrile and using triethylamine as base; LC-MS: $t_R$=0.21 min, $[M+1]^+$=167.04.

N-Hydroxy-4-(2-hydroxy-ethylsulfamoyl)-benzamidine a) To a solution of 4-cyano-benzenesulfonyl chloride (1.00 g, 4.96 mmol) in THF, ethanolamine (454 mg, 7.44 mmol) is added. The mixture becomes slightly warm (30° C.) and turbid. The mixture is stirred at rt for 3 h before it is diluted with EA, washed with sat. aq. $NH_4Cl$ solution and water, dried over $MgSO_4$, filtered and concentrated to give crude 4-cyano-N-(2-hydroxy-ethyl)-benzenesulfonamide (1.26 g) as a white solid; LC-MS: $t_R$=0.34 min, $[M+1+CH_3CN]^+$=268.13.
b) A mixture of 4-cyano-N-(2-hydroxy-ethyl)-benzenesulfonamide (1.25 g, 5.56 mmol), hydroxylamine hydrochloride (773 mg, 11.1 mmol) and $NaHCO_3$ (934 mg, 11.1 mmol) in methanol is stirred at 60° C. for 7 h. The mixture is filtered and the filtrate is concentrated. The residue is dissolved in EA (250 mL) and washed with water (5 mL). The organic extract is dried over $MgSO_4$, filtered, concentrated and dried to give the title compound (720 mg) as a white solid; LC-MS: $t_R$=0.23 min.

[4-(N-Hydroxycarbamimidoyl)-benzenesulfonylamino]-acetic acid ethyl ester

The title compound is prepared in analogy to N-hydroxy-4-(2-hydroxy-ethylsulfamoyl)-benzamidine starting from 4-cyano-benzenesulfonyl chloride and glycine ethyl ester hydrochloride; LC-MS: $t_R$=0.27 min; $[M+1]^+$=302.03;

{2-[4-(N-Hydroxycarbamimidoyl)-benzenesulfonylamino]-ethyl}-carbamic acid tert-butyl ester The title compound is prepared in analogy to N-hydroxy-4-(2-hydroxy-ethylsulfamoyl)-benzamidine starting from 4-cyano-benzenesulfonyl chloride and (2-amino-ethyl)-carbamic acid tert-butyl ester; LC-MS: $t_R$=0.40 min; $[M+1]^+$=359.09; $^1$H NMR ($D_6$-DMSO): δ1.35 (s, 9H), 2.73-2.81 (m, 2H), 2.92-3.00 (m, 2H), 5.96 (s, 2H), 6.78 (t br, J=5.5 Hz, 1H), 7.69 (t br, J=6.0 Hz, 1H), 7.75-7.79 (m, 2H), 7.86-7.90 (m, 2H), 9.92 (s, 1H).

N-Hydroxy-4-(2-hydroxy-ethyl)-benzamidine

The title compound (2.36 g) is obtained as a white solid in analogy to N-hydroxy-4-(2-hydroxy-ethylsulfamoyl)-benzamidine (step b) starting from 4-(2-hydroxy-ethyl)-benzonitrile (2.00 g, 13.2 mmol) and hydroxylamine hydrochloride (2.75 g, 39.5 mmol); LC-MS: $t_R$=0.34 min; $[M+1]^+$=181.00; $^1$H NMR ($D_6$-DMSO): δ 2.74 (t, J=6.8 Hz, 2H), 3.58-3.66 (m, 2H), 4.64 (t, J=5.0 Hz, 1H), 5.74 (s, 2H), 7.22 (d, J=7.8 Hz, 2H), 7.58 (d, J=7.8 Hz, 2H), 9.53 (s, 1H).

4-Allyl-N-hydroxy-benzamidine

The title compound is obtained in analogy to rac-4-(2,2-dimethyl-[1,3]dioxolan-4-ylmethoxy)-N-hydroxy-3,5-dimethyl-benzamidine (step b) starting from 3-(4-cyanophenyl)-1-propene; LC-MS: $t_R$=0.59 min, [M+H]$^+$=177.03.

4-Amino-3-chloro-N-hydroxy-5-methyl-benzamidine

The title compound is prepared from commercially available 4-amino-3-chloro-5-methylbenzonitrile in analogy to 4,N-dihydroxy-3,5-dimethyl-benzamidine; LC-MS: $t_R$=0.50 min; [M+1]$^+$=200.01; $^1$H NMR (D$_6$-DMSO): δ 2.15 (s, 3H), 5.20 (s, 2H), 5.61 (s, 2H), 7.28 (s, 1H), 7.40 (s, 1H), 9.33 (s, 1H).

4-Benzyloxy-3-ethyl-5-methyl-benzoic acid a) To an ice-cold solution of H$_2$SO$_4$ (150 mL) in water (250 mL), 2-ethyl-6-methylaniline (15.0 g, 111 mmol) is added. The solution is treated with ice (150 g) before a solution of NaNO$_2$ (10.7 g, 155 mmol) in water (150 mL) and ice (50 g) is added dropwise. The mixture is stirred at 0° C. for 1 h. 50% aq. H$_2$SO$_4$ (200 mL) is added and stirring is continued at rt for 18 h. The mixture is extracted with DCM and the organic extracts are dried over MgSO$_4$ and evaporated. The crude product is purified by CC on silica gel eluting with heptane: EA 9:1 to give 2-ethyl-6-methyl-phenol (8.6 g) as a crimson oil; LC-MS: $t_R$=0.89 min; $^1$H NMR (CDCl$_3$): δ 7.03-6.95 (m, 2H), 6.80 (t, J=7.6 Hz, 1H), 4.60 (s, 1H), 2.64 (q, J=7.6 Hz, 2H), 2.25 (s, 3H), 1.24 (t, J=7.6 Hz, 3H).
b) A solution of 2-ethyl-6-methyl-phenol (8.40 g, 61.7 mmol) and hexamethylene tetraamine (12.97 g, 92.5 mmol) in acetic acid (60 mL) and water (14 mL) is heated to 115° C. The water is distilled off at 117° C. and collected with a Dean-Stark apparatus. Then the water separator is replaced by a reflux condensor and the mixture is refluxed for 3 h. The mixture is cooled to rt, diluted with water (100 mL) and extracted with EA. The organic extract is washed with sat. aq. NaHCO$_3$, dried over MgSO$_4$ and evaporated. The remaining solid is dissolved in EA and treated with heptane to initialize crystallisation. The solid material is collected and dried to give 3-ethyl-4-hydroxy-5-methyl-benzaldehyde (3.13 g) as a colourless crystalline powder, $^1$H NMR (CDCl$_3$): δ 9.83 (s, 1H), 7.58-7.53 (m, 2H), 5.30 (s br, 1H), 2.69 (q, J=7.6 Hz, 2H), 2.32 (s, 3H), 1.28 (t, J=7.6 Hz, 3H).
c) To a solution of 3-ethyl-4-hydroxy-5-methyl-benzaldehyde (34.9 g, 0.213 mol) in MeCN (350 mL), K$_2$CO$_3$ (58.7 g, 0.425 mol) and benzylbromide (36.4 g, 0.213 mol) is added. The mixture is stirred at 60° C. for 2 h before it is cooled to rt, diluted with water and extracted twice with EA. The organic extracts are washed with water and concentrated to give crude 4-benzyloxy-3-ethyl-5-methyl-benzaldehyde (45 g) as an orange oil. $^1$H NMR (CDCl$_3$): δ 1.29 (t, J=7.5 Hz, 3H), 2.40 (s, 3H), 2.77 (q, J=7.8 Hz, 2H), 4.90 (s, 2H), 7.31-7.52 (m, 5H), 7.62 (d, J=1.5 Hz, 1H), 7.66 (d, J=1.8 Hz, 1H), 9.94 (s, 1H).
d) To a mixture of 4-benzyloxy-3-ethyl-5-methyl-benzaldehyde (132 g, 0.519 mol) and 2-methyl-2-butene (364 g, 5.19 mol) in tert.-butanol (1500 mL), a solution of NaH$_2$PO$_4$ dihydrate (249 g, 2.08 mol) in water (1500 mL) is added. To this mixture, NaClO$_2$ (187.8 g, 2.08 mol) is added in portions. The temperature of the reaction mixture is kept below 30° C., and evolution of gas is observed. Upon completion of the addition, the orange bi-phasic mixture is stirred well for 3 h before it is diluted with TBME (1500 mL). The organic layer is separated and washed with 20% aq. NaHS solution (1500 mL) and water (500 mL). The organic phase is then extracted three times with 0.5 N aq. NaOH (1000 mL) and the aq. phase is acidified with 25% aq. HCl (500 mL) and extracted twice with TBME (1000 mL). These organic extracts are combined and evaporated to dryness to give 4-benzyloxy-3-ethyl-5-methyl-benzoic acid; $^1$H NMR (D$_6$-DMSO): δ 1.17 (t, J=7.5 Hz, 3H), 2.31 (s, 3H), 2.67 (q, J=7.5 Hz, 2H), 4.86 (s, 2H), 7.34-7.53 (m, 5H), 7.68 (s, 2H), 12.70 (s, 1H).

4-Benzyloxy-3-ethyl-5-methyl-benzoic acid hydrazide

To a solution of 4-benzyloxy-3-ethyl-3-methyl-benzoic acid (8.3 g, 30.7 mmol) in DCM (300 mL) is added DIPEA (10.7 mL) and the mixture is cooled to 0° C. before PyBOP (14.5 g, 33.8 mmol) is added. After 10 min, a solution of 1M hydrazine in THF (100 mL) is added dropwise and the mixture is slowly warmed to rt during 2 h. The reaction mixture is then washed with sat. aq. NaHCO$_3$ followed by brine. The organic phase is collected, dried over MgSO$_4$, filtered and evaporated to give the title compound (24 g, 40% purity) as a yellow wax; LC-MS: $t_R$=0.82 min; [M+H]$^+$=285.10.

(S)-3-Ethyl-4-[2-hydroxy-3-(2-hydroxy-acetylamino)-propoxy]-5-methyl-benzoic acid a) To a suspension of 4-benzyloxy-3-ethyl-5-methyl-benzoic acid (10.0 g, 37.0 mmol) in toluene, N,N-dimethylformamide-di-tert. butyl acetal (22.6 g, 111 mmol) is added. The mixture is refluxed for 24 h before another portion of N,N-dimethylformamide-di-tert. butyl acetal (22.6 g, 111 mmol) is added. Refluxing is continued for 3 days and a third portion of N,N-dimethylformamide-di-tert. butyl acetal (22.6 g, 111 mmol) is added. After refluxing for additional 4 days, the mixture is diluted with EA (250 mL), washed with aq. sat. Na$_2$CO$_3$ solution, dried over MgSO$_4$, filtered and concentrated. The crude product is purified by CC on silica gel eluting with heptane:EA 9:1 to give 4-benzyloxy-3-ethyl-5-methyl-benzoic acid tert-butyl ester (9.02 g) as a pale yellow oil, $^1$H NMR (D$_6$-DMSO): δ 1.16 (t, J=7.5 Hz, 3H), 1.54 (s, 9H), 2.30 (s, 3H), 2.65 (q, J=7.5 Hz, 2H), 4.85 (s, 2H), 7.35-7.40 (m, 1H), 7.43 (t, J=6.8 Hz, 2H), 7.47-7.52 (m, 2H), 7.63 (s, 2H).
b) To a solution of 4-benzyloxy-3-ethyl-5-methyl-benzoic acid tert-butyl ester (9.02 g, 27.6 mmol) in THF (50 mL) and ethanol (50 mL), Pd/C (400 mg, 10% Pd) is added. The mixture is stirred at rt under 1 atm of H$_2$. The catalyst is removed by filtration and the filtrate is concentrated. The residue is again dissolved in THF (50 mL) and ethanol (50 m) and treated with Pd/C (400 mg, 10% Pd). The mixture is stirred at rt under 1 atm of H$_2$ for 24 h before the catalyst is again removed by filtration. The filtrate is concentrated and dried to give 3-ethyl-4-hydroxy-5-methyl-benzoic acid tert-butyl ester (7.13 g) as a pale yellow oil; $^1$H NMR (CDCl$_3$): δ 1.28 (t, J=7.8 Hz, 3H), 1.61 (s, 9H), 2.30 (s, 3H), 2.67 (q, J=7.5 Hz, 2H), 5.13 (s br, 1H), 7.67 (s, 1H), 7.69 (s, 1H).
c) 3-Ethyl-4-hydroxy-5-methyl-benzoic acid tert-butyl ester is converted to 3-ethyl-4-[2-hydroxy-3-(2-hydroxy-acetylamino)-propoxy]-5-methyl-benzoic acid tert. butyl ester following the procedures given for (S)-4-(3-amino-2-hydroxypropoxy)-3-ethyl-5-methylbenzonitrile and N—((S)-3-[2-ethyl-4-(N-hydroxycarbamimidoyl)-6-methyl-phenoxy]-2-hydroxy-propyl)-2-hydroxy-acetamide (step a) only); LC-MS: $t_R$=0.87 min; [M+1]$^+$=368.11; $^1$H NMR (D$_6$-

DMSO): δ 1.17 (t, J=7.5 Hz, 3H), 1.53 (s, 9H), 2.28 (s, 3H), 2.66 (q, J=7.5 Hz, 2H), 3.17-3.26 (m, 1H), 3.38-3.46 (m, 1H), 3.64-3.75 (m, 2H), 3.83 (d, J=5.5 Hz, 2H), 3.91-3.97 (m, 1H), 5.28 (d, J=5.3 Hz, 1H), 5.54 (t, J=5.5 Hz, 1H), 7.59 (s, 1H), 7.60 (s, 1H), 7.68 (t br, J=5.5 Hz, 1H).

d) To a cold (0° C.) solution of 3-ethyl-4-[2-hydroxy-3-(2-hydroxy-acetylamino)-propoxy]-5-methyl-benzoic acid tert. butyl ester (5.94 g, 16.2 mmol) in DCM (100 mL), TFA (5 mL) is added and the mixture is stirred at rt for 2 h. The solvent is removed in vacuo and the residue is dissolved in acetonitrile and separated by prep. HPLC to give the title compound (2.20 g) as a white powder; LC-MS: $t_R$=0.41 min; $[M+1]^+$=312.18.

5-[3-(4-Hydroxy-3,5-dimethyl-phenyl)-[1,2,4]oxadiazol-5-yl]-thiophene-2-carbaldehyde The title compound (140 mg) is prepared from 5-formyl-2-thiophene carboxylic acid (468 mg, 3.0 mmol) and 4,N-dihydroxy-3,5-dimethyl-benzamidine (540 mg, 3.0 mmol) according to Method A; LC-MS: $t_R$=1.01 min; $[M+1]^+$=301.04; $^1$H NMR (D$_6$-DMSO): δ2.24 (s, 6H), 7.64 (s, 2H), 8.17 (s, 2H), 8.99 (s, 1H), 10.06 (s, 1H).

rac-N-(3-{4-[5-(5-Formyl-thiophen-2-yl)-[1,2,4]oxadiazol-3-yl]-2,6-dimethyl-phenoxy}-2-hydroxy-propyl)-2-hydroxy-acetamide (Method A)

To a solution of 5-formyl-2-thiophene carboxylic acid (100 mg, 0.64 mmol) in DMF (4 mL), TBTU (226 mg, 0.704 mmol) and DIPEA (414 mg, 3.20 mmol) are added. The mixture is stirred at rt for 10 min before rac-2-hydroxy-N-{2-hydroxy-3-[4-(N-hydroxycarbamimidoyl)-2,6-dimethyl-phenoxy]-propyl}-acetamide (217 mg, 0.608 mmol) is added. Stirring is continued for 100 min before the mixture is separated without any work-up by prep. HPLC (GROM-SIL ODS-4HE, 30×75 mm, 10 μm, 90% to 5% water (containing 0.5% HCOOH) in acetonitrile) to give the hydroxy-amidine ester intermediate (70 mg) as a pale yellow solid; LC-MS: $t_R$=0.75 min; $[M+1]^+$=450.14. This material is dissolved in dioxane (40 mL) and the resulting solution is heated to 110° C. for 16 h. The solvent is removed in vacuo and the residue is dried to give the title compound (60 mg) as a pale yellow solid; LC-MS: $t_R$=0.87 min; $[M+1]^+$=432.07; $^1$H NMR (D$_6$-DMSO): δ 2.34 (s, 6H), 3.21-3.28 (m, 1H), 3.40-3.47 (m, 1H), 3.70-3.81 (m, 2H), 3.83 (d, J=5.5 Hz, 2H), 3.92-3.98 (m, 1H), 5.28 (d, J=5.0 Hz, 1H), 5.54 (t, J=5.8 Hz, 1H), 7.69 (t br, J=5.8 Hz, 1H), 7.76 (s, 2H), 8.20 (d, J=4 Hz, 1H), 8.22 (d, J=4 Hz, 1H), 10.10 (s, 1H).

rac-5-{3-[4-(2,2-Dimethyl-[1,3]dioxolan-4-yl-methoxy)-3,5-dimethyl-phenyl]-[1,2,4]oxadiazol-5-yl}-3-methyl-thiophene-2-carbaldehyde The title compound is prepared according to Method A starting from 5-formyl-4-methyl-thiophene-2-carboxylic acid and rac-4-(2,2-dimethyl-[1,3]dioxolan-4-ylmethoxy)-N-hydroxy-3,5-dimethyl-benzamidine; LC-MS: $t_R$=1.16 min; $[M+1]^+$=429.16; $^1$H NMR (D$_6$-DMSO): δ1.34 (s, 3H), 1.38 (s, 3H), 2.34 (s, 6H), 2.65 (s, 3H), 3.79-3.93 (m, 3H), 4.10-4.15 (m, 1H), 4.42-4.49 (m, 1H), 7.75 (s, 2H), 8.07 (s, 1H), 10.17 (s, 1H).

rac-N-(3-{4-[5-(5-Formyl-4-methyl-thiophen-2-yl)-[1,2,4]oxadiazol-3-yl]-2,6-dimethyl-phenoxy}-2-hydroxy-propyl)-2-hydroxy-acetamide The title compound is prepared according to Method A starting from 5-formyl-4-methyl-thiophene-2-carboxylic acid and rac-2-hydroxy-N-{2-hydroxy-3-[4-(N-hydroxycarbamimidoyl)-2,6-dimethyl-phenoxy]-propyl}-acetamide; LC-MS: $t_R$=0.90 min; $[M+1]^+$=446.15; $^1$H NMR (D$_6$-DMSO): δ 2.34 (s, 6H), 2.65 (s, 3H), 3.19-3.28 (m, 1H), 3.39-3.48 (m, 1H), 3.70-3.81 (m, 2H), 3.83 (d, J=5.8 Hz, 2H), 3.92-3.99 (m, 1H), 5.29 (d, J=5.5 Hz, 1H), 5.55 (t, J=6.0 Hz, 1H), 7.69 (m, 1H), 7.75 (s, 2H), 8.07 (s, 1H), 10.17 (s, 1H).

(2S)—N-(3-{4-[5-(5-Formyl-4-methyl-thiophen-2-yl)-[1,2,4]oxadiazol-3-yl]-2,6-dimethyl-phenoxy}-2-hydroxy-propyl)-2-hydroxy-acetamide The title compound is prepared according to Method A starting from 5-formyl-4-methyl-thiophene-2-carboxylic acid and (S)-2-hydroxy-N-{2-hydroxy-3-[4-(N-hydroxycarbamimidoyl)-2,6-dimethyl-phenoxy]-propyl}-acetamide; LC-MS*: $t_R$=0.77 min; $[M+1]^+$=445.92.

3-{4-[5-(5-Formyl-4-methyl-thiophen-2-yl)-[1,2,4]oxadiazol-3-yl]-2,6-dimethyl-phenyl}-propionic acid The title compound is prepared according to Method A starting from 5-formyl-4-methyl-thiophene-2-carboxylic acid and 3-[4-(N-hydroxycarbamimidoyl)-2,6-dimethyl-phenyl]-propionic acid; LC-MS: $t_R$=1.03 min; $[M+1]^+$=371.04; $^1$H NMR (D$_6$-DMSO): δ 2.36-2.42 (m, 8H), 2.65 (s, 3H), 2.89-2.95 (m, 2H), 7.70 (s, 2H), 8.06 (s, 1H), 10.16 (s, 1H), 12.26 (m, 1H).

N—((S)-3-{2-Ethyl-4-[5-(5-formyl-4-methyl-thiophen-2-yl)-[1,2,4]oxadiazol-3-yl]-6-methyl-phenoxy}-2-hydroxy-propyl)-2-hydroxy-acetamide The title compound is prepared according to Method A starting from 5-formyl-4-methyl-thiophene-2-carboxylic acid and N—((S)-3-[2-ethyl-4-(N-hydroxycarbamimidoyl)-6-methyl-phenoxy]-2-hydroxy-propyl)-2-hydroxy-acetamide; LC-MS: $t_R$=0.92 min; $[M+1]^+$=460.17; $^1$H NMR δ 1.22 (t, J=7.5 Hz, 3H), 2.35 (s, 3H), 2.65 (s, 3H), 2.73 (q, J=7.5 Hz, 2H), 3.20-3.28 (m, 1H), 3.39-3.47 (m, 1H), 3.70-3.80 (m, 2H), 3.84 (d, J=5.5 Hz, 2H), 3.92-4.00 (m, 1H), 5.30 (d, J=5.3 Hz, 1H), 5.54 (t, J=5.8 Hz, 1H), 7.69 (t, J=5.5 Hz, 1H), 7.76 (s, 2H), 8.07 (s, 1H), 10.17 (s, 1H).

3-{2-Ethyl-4-[5-(5-formyl-4-methyl-thiophen-2-yl)-[1,2,4]oxadiazol-3-yl]-6-methyl-phenyl}-propionic acid ethyl ester The title compound is prepared according to Method A starting from 5-formyl-4-methyl-thiophene-2-carboxylic acid and 3-[2-ethyl-4-(N-hydroxycarbamimidoyl)-6-methyl-phenyl]-propionic acid ethyl ester; LC-MS: $t_R$=1.19 min; $[M+1]^+$=413.15; $^1$H NMR (D$_6$-DMSO) δ 1.20 (t, J=7.5 Hz, 3H), 1.22 (t, J=7.5 Hz, 3H), 2.40 (s, 3H), 2.44-2.50 (m, 2H), 2.65 (s, 3H), 2.73 (q, J=7.5 Hz, 2H), 2.93-3.00 (m, 2H), 4.11 (q, J=7.0 Hz, 2H), 7.71 (s, 1H), 7.72 (s, 1H), 8.07 (s, 1H), 10.17 (s, 1H).

N—((S)-3-{2-Ethyl-4-[5-(5-formyl-3,4-dimethyl-thiophen-2-yl)-[1,2,4]oxadiazol-3-yl]-6-methyl-phenoxy}-2-hydroxy-propyl)-2-hydroxy-acetamide The title compound is prepared according to Method A starting from 5-formyl-3,4-dimethyl-thiophene-2-carboxylic acid and N—((S)-3-[2-ethyl-4-(N-hydroxycarbamimidoyl)-6-methyl-phenoxy]-2-hydroxy-propyl)-2-hydroxy-acetamide; LC-MS: $t_R$=0.95 min; $[M+H]^+$=474.07; $^1$H NMR (D$_6$-

DMSO): δ 1.22 (t, J=7.5 Hz, 3H), 2.35 (s, 3H), 2.57 (s, 3H), 2.63 (s, 3H), 2.73 (q, J=7.8 Hz, 2H), 3.20-3.28 (m, 1H), 3.39-3.48 (m, 1H), 3.70-3.81 (m, 2H), 3.84 (d, J=5.5 Hz, 2H), 3.92-4.01 (m, 1H), 5.31 (d, J=4.8 Hz, 1H), 5.55 (t, J=5.5 Hz, 1H), 7.70 (t, J=5.3 Hz, 1H), 7.77 (s, 2H), 10.22 (s, 1H).

3-(2-Ethyl-4-[5-(5-formyl-3,4-dimethyl-thiophen-2-yl)-[1,2,4]oxadiazol-3-yl]-6-methyl-phenyl}-propionic acid The title compound is prepared according to Method A starting from 5-formyl-3,4-dimethyl-thiophene-2-carboxylic acid and 3-[2-ethyl-4-(N-hydroxycarbamimidoyl)-6-methyl-phenyl]-propionic acid; LC-MS: $t_R$=1.08 min; $[M+1]^+$=399.05.

Reductive Amination (Method B)

To a solution of the 5-formyl-thiophen-2-yl-oxadiazol derivative (1 eq., usual scale 0.02-0.25 mmol) and the appropriate amine (2-40 eq.) in methanol (24 mL/mmol), a solution of NaBH$_4$ (20 eq.) in methanol is added. The mixture is stirred overnight at rt before it is diluted with water (4 mL/mmol) and acidified with formic acid (4 mL/mmol). The mixture is separated by prep. HPLC (XBridge Prep C18, 19×50 mm, 5 µm, 10% to 95% acetonitrile in water containing 0.5% formic acid) to give the desired 5-aminomethyl-thiophen-2-yl-oxadiazol derivative as a colourless to pale yellow resin.

Reductive Amination (Method C)

To a solution of the 5-formyl-thiophen-2-yl-oxadiazol derivative (1 eq., usual scale 0.02-0.25 mmol) and the appropriate amine (2-40 eq.) in DCM (24 mL/mmol) and NMP (6 mL/mmol), sodium triacetoxy borohydride (NaBH(OAc)$_3$) (3 eq.) is added. The mixture is stirred for 2 h before another portion of NaBH(OAc)$_3$ (3 eq.) is added. Stirring of the suspension is continued for another 2 h and a third portion of NaBH(OAc)$_3$ (3 eq.) is added. The mixture is stirred for 16 h before the DCM is evaporated. The remaining residue is diluted with water (4 mL/mmol) and formic acid (4 mL/mmol) and the resulting solution is separated by prep. HPLC (XBridge Prep C18, 19×50 mm, 5 µm, 10% to 95% acetonitrile in water containing 0.5% formic acid) to give the desired 5-aminomethyl-thiophen-2-yl-oxadiazol derivative as a colourless to pale yellow resin.

Reductive Amination (Method D)

To a solution of the 5-formyl-thiophen-2-yl-oxadiazol derivative (1 eq., usual scale 0.02-0.25 mmol) and the appropriate amine (2-40 eq.) in methanol (24 mL/mmol), sodium triacetoxy borohydride (NaBH(OAc)$_3$) (10 eq.) is added. The mixture is stirred for 2 h before NaBH$_3$CN (10 eq.) is added. Stirring of the suspension is continued for 16 h before NaBH$_4$ (20 eq.) is added and stirring is continued for another 16 h at rt. The reaction mixture is diluted with water (4 mL/mmol) and formic acid (4 mL/mmol) and the resulting solution is separated by prep. HPLC (Waters Symmetry C18 19×50 mm, 5 µm, 10 to 95% acetonitrile in water containing 0.5% HCOOH) to give the desired 5-aminomethyl-thiophen-2-yl-oxadiazol derivative as a colourless to pale yellow resin.

(S)-5-(3-[4-(2,2-Dimethyl-[1,3]dioxolan-4-yl-methoxy)-3-ethyl-5-methyl-phenyl]-[1,2,4]oxadiazol-5-yl}-3-ethyl-thiophene-2-carbaldehyde (Method E)

A solution of 4-ethyl-5-formyl-thiophene-2-carboxylic acid (20 mg, 0.109 mmol), HOBt (18 mg, 0.131 mmol), and EDC HCl (23 mg, 0.120 mmol) in DMF (0.75 mL) is stirred at rt for 5 min before (S)-4-(2,2-dimethyl-[1,3]dioxolan-4-ylmethoxy)-3-ethyl-N-hydroxy-5-methyl-benzamidine (34 mg, 0.109 mmol) is added. The mixture is stirred at rt for 1 h, then at 85° C. for 2 days. The title compound is isolated as a colourless oil (28 mg) by separating the reaction mixture by prep. HPLC (column: Atlantis T3, 30×75 mm, 10 µm, eluting with a gradient of acetonitrile in water containing 0.5% of formic acid); LC-MS: $t_R$=1.06 min; $[M+1]^+$=457.19.

N—((S)-3-(2-Ethyl-4-[5-(4-ethyl-5-formyl-thiophen-2-yl)-[1,2,4]oxadiazol-3-yl]-6-methyl-phenoxy}-2-hydroxy-propyl)-2-hydroxy-acetamide The title compound is prepared according to Method E starting from 4-ethyl-5-formyl-thiophene-2-carboxylic acid and N—((S)-3-{2-ethyl-4-[5-(5-formyl-3,4-dimethyl-thiophen-2-yl)-[1,2,4]oxadiazol-3-yl]-6-methyl-phenoxy}-2-hydroxy-propyl)-2-hydroxy-acetamide; LC-MS: $t_R$=0.73 min; $[M+1]^+$=474.20.

3-(2-Ethyl-4-[5-(4-ethyl-5-formyl-thiophen-2-yl)-[1,2,4]oxadiazol-3-yl]-6-methyl-phenyl}-propionic acid The title compound is prepared according to Method E followed by treating the corresponding propionic ester derivative for 1 h at rt with 1 N aq. NaOH in methanol starting from 4-ethyl-5-formyl-thiophene-2-carboxylic acid and 3-[2-ethyl-4-(N-hydroxycarbamimidoyl)-6-methyl-phenyl]-propionic acid ethyl ester; LC-MS: $t_R$=0.87 min; $[M+1]^+$=399.20.

N-((2S)-3-{2-Ethyl-4-[3-(5-formyl-4-methyl-thiophen-2-yl)-[1,2,4]oxadiazol-5-yl]-6-methyl-phenoxy}-2-hydroxy-propyl)-2-hydroxy-acetamide The title compound (153 mg) is obtained starting from (S)-3-ethyl-4-[2-hydroxy-3-(2-hydroxy-acetylamino)-propoxy]-5-methyl-benzoic acid (300 mg, 0.964 mmol) and 5-formyl-N-hydroxy-4-methyl-thiophene-2-carboxamidine (287 mg, 1.50 mmol) following Method E; LC-MS: $t_R$=0.80 min; $[M+1]^+$=459.96; $^1$H NMR (D$_6$.DMSO): δ 1.23 (t, J=7.5 Hz, 3H), 2.37 (s, 3H), 2.65 (s, 3H), 2.75 (q, J=7.3 Hz, 2H), 3.21-3.30 (m, 1H), 3.39-3.46 (m, 1H), 3.73-3.82 (m, 2H), 3.84 (d, J=5.8 Hz, 2H), 3.93-3.99 (m, 1H), 5.32 (d, J=5.3 Hz, 1H), 5.55 (t, J=5.8 Hz, 1H), 7.71 (t, J=5.8 Hz), 7.87-7.90 (m, 3H), 10.14 (s, 1H).

N-((2S)-3-{2-Ethyl-4-[5-(5-formyl-4-methyl-thiophen-2-yl)-[1,3,4]oxadiazol-2-yl]-6-methyl-phenoxy}-2-hydroxy-propyl)-2-hydroxy-acetamide A solution of (S)-3-ethyl-4-[2-hydroxy-3-(2-hydroxy-acetylamino)-propoxy]-5-methyl-benzoic acid (200 mg, 0.642 mmol), 5-[1,3]dioxolan-2-yl-4-methyl-thiophene-2-carboxylic acid hydrazide (147 mg, 0.642 mmol) and DIPEA (266 mg, 2.06 mmol) in DCM (20 mL) and DMF (4 mL) is cooled to 0° C. before PyBOP (501 mg, 0.964 mmol) is added. The mixture is stirred at 0° C. for 30 min, is then warmed to reflux for 3 h. The solvent is evaporated and the residue is dissolved in EA and washed twice with sat. aq. NaHCO$_3$ solution. The washings are extracted back with EA. The organic extracts are dried over Na$_2$SO$_4$, filtered and concentrated to give crude 5-[1,3]dioxolan-2-yl-4-methyl-thiophene-2-carboxylic acid N'-(4-benzyloxy-3-ethyl-5-methyl-benzoyl)-hydrazide (201 mg); LC-MS*: $t_R$=0.51 min; $[M+1]^+$=521.67. A portion of this material (80 mg, 153 µmol)

is dissolved in DCM (2 mL) and DMF 80.5 mL). Triethylamine (37 mg, 368 μmol) is added followed by 2-chloro-1,3-dimethylimidazolinium chloride (31 mg, 184 μmol). The mixture is stirred at rt for 16 h before another portion of 2-chloro-1,3-dimethylimidazolinium chloride (16 mg, 92 μmol) and triethylamine (19 mg, 184 μmol) is added. Stirring is continued at 60° C. for 2 h whereby the DCM is evaporated. The mixture is acidified by adding 1 N aq. HCl (200 μL) and stirring is continued at rt for 10 min. The reaction mixture is separated by prep. HPLC to give the title compound (12 mg) as a colourless resin; LC-MS: $t_R$=0.63 min; [M+H]$^+$=460.11.

5-[5-(3-Ethyl-4-hydroxy-5-methyl-phenyl)-[1,3,4]thiadiazol-2-yl]-3-methyl-thiophene-2-carbaldehyde PyBOP (4.10 g, 7.88 mmol) and DIPEA (2.17 g, 16.8 mmol) is added to a cooled solution (0° C.) of 5-[1,3]dioxolan-2-yl-4-methyl-thiophene-2-carboxylic acid (1.42 g, 5.26 mmol) in DMF (20 mL). 4-Benzyloxy-3-ethyl-5-methyl-benzoic acid hydrazide (1.20 g, 5.26 mmol) is then added and the mixture is stirred at 0° C. for 30 min, then at rt for 1 h. The mixture is concentrated in vacuo, diluted with EA and washed with aq. sat. NaHCO$_3$ followed by water. The organic extract is dried over Na$_2$SO$_4$, filtered and concentrated. The crude product is purified by prep. HPLC (XBridge Rp C18, 50×50 +50×100 mm, eluting with a gradient of acetonitrile in water containing 0.5% of formic acid) and the product containing fractions are neutralised by adding aq. Na$_2$CO$_3$ solution. The organic solvent is evaporated and the remaining aq. solution is extracted twice with EA. The organic extracts are concentrated. The product is further purified by prep. HPLC (XBridge Rp C18 50×50 +50×100 mm, eluting with a gradient of acetonitrile in water containing 0.5% of aq. ammonia) to give 5-[1,3]dioxolan-2-yl-4-methyl-thiophene-2-carboxylic acid N'-(4-benzyloxy-3-ethyl-5-methyl-benzoyl)-hydrazide (1.26 g) as a beige solid; LC-MS*: $t_R$=0.77 min; [M+1]$^+$=481.05. To a solution of this material (1.14 g, 2.37 mmol) in THF (40 mL), Lawesson's reagent (1.92 g, 4.74 mmol) is added. The resulting suspension is heated to 70° C. with microwave irradiation (200 W, with concomitant cooling). The clear solution is concentrated, dissolved in DMF and separated by prep. HPLC (XBridge, RP C18, 30×75 mm, eluting with a gradient of acetonitrile in water containing 0.5% of formic acid) to give 5-[5-(4-benzyloxy-3-ethyl-5-methyl-phenyl)-[1,3,4]thiadiazol-2-yl]-3-methyl-thiophene-2-carbaldehyde (294 mg) as a beige resin, LC-MS: $t_R$=0.95 min; [M+1]$^+$=435.07; $^1$H NMR (D$_6$-DMSO): δ 1.22 (t, J=7.5 Hz, 3H), 2.38 (s, 3H), 2.63 (s, 3H), 2.73 (q, J=7.5 Hz, 2H), 4.91 (s, 2H), 7.37-7.48 (m, 3H), 7.50-7.54 (m, 2H), 7.75-7.78 (m, 2H), 7.82 (s, 1H), 10.13 (s, 1H). The above benzyl ether (284 mg, 0.654 mmol) is dissolved in acetic acid (10 mL) and 33% HBr in acetic acid (11 mL). The mixture is stirred at rt for 10 min before the solvent is removed in vacuo. The residue is dissolved in DMF and separated by prep. HPLC (XBridge, RP C18, 30×75 mm, eluting with a gradient of acetonitrile in water containing 0.5% of formic acid) to give the title compound (74 mg) as a pale yellow powder; LC-MS: $t_R$=0.77 min; [M+1]$^+$=345.07; $^1$H NMR (D$_6$-DMSO): δ 1.19 (t, J=7.5 Hz, 3H), 2.27 (s, 3H), 2.62 (s, 3H), 2.68 (q, J=7.3 Hz, 2H), 7.60-7.64 (m, 2H), 7.77 (s, 1H), 9.12 (s, 1H), 10.12 (s, 1H).

Examples 1 to 6

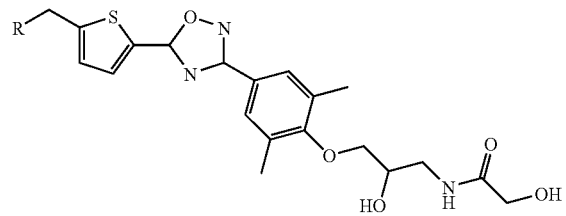

The following examples are prepared starting from rac-N-(3-{4-[5-(5-formyl-thiophen-2-yl)-[1,2,4]oxadiazol-3-yl]-2,6-dimethyl-phenoxy}-2-hydroxy-propyl)-2-hydroxy-acetamide and the appropriate amines according to Method C.

| | | LC-MS | |
|---|---|---|---|
| Example | R | $t_R$ [min] | [M + H]$^+$ |
| 1 | HN— | 0.67 | 447.12 |
| 2 | HN—\ | 0.68 | 461.23 |
| 3 | HN—⟨ | 0.70 | 475.24 |
| 4 | N— | 0.67 | 461.17 |
| 5 | N—\ | 0.69 | 475.27 |
| 6 | N(pyrrolidine) | 0.70 | 487.2 |

Example 4

$^1$H NMR (D$_6$-DMSO): δ2.25 (s, 6H), 2.33 (s, 6H), 3.20-3.28 (m, 1H), 3.40-3.48 (m, 1H), 3.73 (s, 2H), 3.75-3.79 (m, 2H), 3.83 (d, J=5.5 Hz, 2H), 3.91-3.99 (m, 1H), 5.29 (d, J=5.0 Hz, 1H), 5.54 (t, J=5.8 Hz, 1H), 7.20 (d, J=3.8 Hz, 1H), 7.69 (t, J=5.8 Hz, 1H), 7.73 (s, 2H), 7.93 (d, J=3.8 Hz, 1H).

Example 7

4-[5-(5-Dimethylaminomethyl-thiophen-2-yl)-[1,2,4]oxadiazol-3-yl]-2,6-dimethyl-phenol The title compound is prepared from 5-[3-(4-hydroxy-3,5-dimethyl-phenyl)-[1,2,4]oxadiazol-5-yl]-thiophene-2-carbaldehyde and dimethylamine according to Method B; LC-MS: $t_R$=0.75 min; [M+1]$^+$=330.05.

Examples 8 to 20

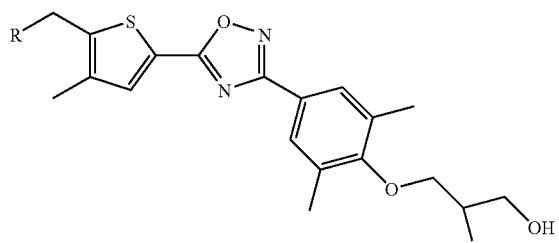

a) rac-5-{3-[4-(2,2-Dimethyl-[1,3]dioxolan-4-ylmethoxy)-3,5-dimethyl-phenyl]-[1,2,4]oxadiazol-5-yl}-3-methyl-thiophene-2-carbaldehyde is reacted with the appropriate amine according to Method D to give the corresponding C-(5-{3-[4-(2,2-dimethyl-[1,3]dioxolan-4-ylmethoxy)-3,5-dimethyl-phenyl]-[1,2,4]oxadiazol-5-yl}-3-methyl-thiophen-2-yl)-methylamine derivatives.

b) The above methylamine derivatives (10-20 μmol) are dissolved in acetonitrile (1 mL), treated with 5 N HCl in isopropanol (100 μL), diluted with methanol (100-250 μL), and stirred at rt for 1 h. The reaction mixture is neutralised by adding triethylamine (100 μL), diluted with water and separated by prep. HPLC (XBridge Prep C18, 19×50 mm, 5 μm, 10-95% acetonitrile in water containing 0.5% of sat. aq. NH$_3$) to give the desired rac-3-{4-[5-(5-aminomethyl-4-methyl-thiophen-2-yl)-[1,2,4]oxadiazol-3-yl]-2,6-dimethyl-phenoxy}-propane-1,2-diol derivatives as colourless to pale yellow resins.

| Example | R | LC-MS $t_R$ [min] | [M + H]$^+$ |
|---|---|---|---|
| 8 | HN–CH$_3$ | 0.79* | 404.07 |
| 9 | HN–Et | 0.84* | 418.08 |
| 10 | HN–nPr | 0.90* | 432.09 |
| 11 | HN–iPr | 0.90* | 432.09 |
| 12 | HN–nBu | 0.96* | 446.10 |
| 13 | HN–iBu | 0.98* | 446.10 |
| 14 | N(Me)–propyl | 1.05* | 446.09 |
| 15 | N(Me)–CH$_2$CH$_2$OH | 0.77* | 448.10 |
| 16 | N(Et)–CH$_2$CH$_2$OH | 0.83* | 462.08 |
| 17 | azetidine | 0.88* | 430.09 |
| 18 | pyrrolidine | 0.98* | 444.11 |
| 19 | piperidine | 1.08* | 457.82 |
| 20 | morpholine | 0.86* | 460.02 |

*basic conditions

Example 17

$^1$H NMR (D$_6$-DMSO): δ2.00-2.09 (m, 2H), 2.21 (s, 3H), 2.34 (s, 6H), 3.20-3.30 (m, 4H), 3.45-3.54 (m, 2H), 3.72-3.88 (m, 3H), 4.64 (t, J=4.8 Hz, 1H), 4.96 (d, J=4.3 Hz, 1H), 7.72 (s, 2H), 7.80 (s, 1H).

Examples 21 to 33

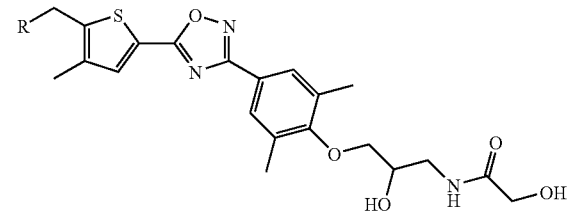

The following examples are prepared starting from rac-N-(3-{4-[5-(5-formyl-4-methyl-thiophen-2-yl)-[1,2,4]oxadiazol-3-yl]-2,6-dimethyl-phenoxy}-2-hydroxy-propyl)-2-hydroxy-acetamide and the appropriate amines.

| Example | R | according to Method | LC-MS $t_R$ [min] | [M + H]$^+$ |
|---|---|---|---|---|
| 21 | HN–CH$_3$ | D | 0.69 | 461.23 |
| 22 | HN–Et | D | 0.71 | 475.19 |
| 23 | HN–nPr | D | 0.73 | 489.28 |

-continued

| Example | R | according to Method | LC-MS $t_R$ [min] | $[M + H]^+$ |
|---|---|---|---|---|
| 24 | HN–iPr | D | 0.72 | 489.28 |
| 25 | HN–nBu | D | 0.76 | 503.29 |
| 26 | HN–iBu | D | 0.75 | 503.29 |
| 27 | N(Me)Me | C | 0.82 | 475.39 |
| 28 | N(Me)Et | C | 0.73 | 503.18 |
| 29 | N(Me)iPr | D | 0.73 | 503.21 |
| 30 | N(Me)CH2CH2OH | D | 0.69 | 505.25 |
| 31 | N(Et)CH2CH2OH | D | 0.70 | 519.28 |
| 32 | pyrrolidinyl | D | 0.72 | 501.25 |
| 33 | piperidinyl | D | 0.74 | 515.20 |

Example 27

$^1$H NMR (CDCl$_3$): δ2.27 (s, 3H), 2.36 (s, 12H), 3.48-3.57 (m, 1H), 3.62 (s, 2H), 3.76-3.92 (m, 3H), 4.17-4.24 (m, 3H), 6.95-7.03 (m, 1H), 7.68 (s, 1H), 7.82 (s, 2H).

Example 28

$^1$H NMR (D$_6$-DMSO): δ0.90 (t, J=7.3 Hz, 3H), 1.45-1.56 (m, 2H), 2.23 (s, 3H), 2.25 (s, 3H), 2.33 (s, 6H), 2.40 (t, J=7.0 Hz, 2H), 3.20-3.28 (m, 1H), 3.39-3.48 (m, 1H), 3.68 (s, 2H), 3.69-3.80 (m, 3H), 3.84 (d, J=5.8 Hz, 2H), 3.91-3.99 (m, 1H), 5.28 (d, J=5.3 Hz, 1H), 5.54 (t, J=5.8 Hz, 1H), 7.68 (t, J=5.5 Hz, 1H), 7.72 (s, 2H), 7.81 (s, 1H).

Examples 34 to 49

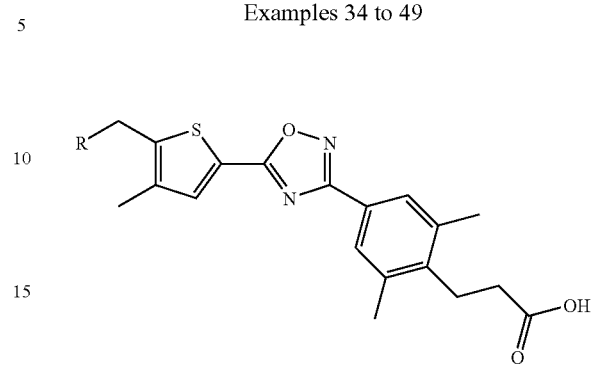

The following examples are prepared according to Method D starting from 3-{4-[5-(5-formyl-4-methyl-thiophen-2-yl)-[1,2,4]oxadiazol-3-yl]-2,6-dimethyl-phenyl}-propionic acid.

| Example | R | LC-MS $t_R$ [min] | $[M + H]^+$ |
|---|---|---|---|
| 34 | HN–Me | 0.78 | 386.05 |
| 35 | HN–Et | 0.80 | 399.93 |
| 36 | HN–nPr | 0.82 | 414.21 |
| 37 | HN–iPr | 0.81 | 414.18 |
| 38 | HN–nBu | 0.85 | 428.22 |
| 39 | HN–iBu | 0.85 | 428.21 |
| 40 | N(Me)Me | 0.79 | 400.05 |
| 41 | N(Me)Et | 0.81 | 414.19 |
| 42 | N(Me)nPr | 0.84 | 428.25 |
| 43 | N(Me)iPr | 0.82 | 428.23 |
| 44 | N(Et)Et | 0.82 | 428.21 |

-continued

| Example | R | LC-MS $t_R$ [min] | $[M + H]^+$ |
|---|---|---|---|
| 45 | N(CH3)CH2CH2OH | 0.78 | 430.20 |
| 46 | N(CH2CH3)CH2CH2OH | 0.79 | 444.25 |
| 47 | azetidinyl | 0.80 | 412.12 |
| 48 | pyrrolidinyl | 0.82 | 426.15 |
| 49 | piperidinyl | 0.83 | 440.22 |

Example 43

¹H NMR (D₆-DMSO): δ1.05 (d, J=6.3 Hz, 6H), 2.22 (s, 6H), 2.35-2.42 (m, 8H), 2.88-2.97 (m, 3H), 3.70 (s, 2H), 7.68 (s, 2H), 7.79 (s, 1H).

Examples 50 to 60

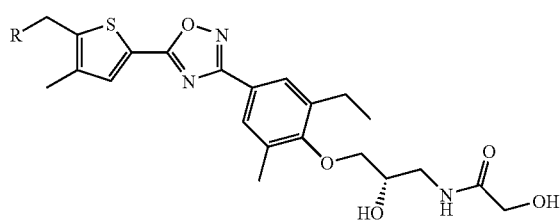

The following examples are prepared according to Method C starting from N—((S)-3-{2-ethyl-4-[5-(5-formyl-4-methyl-thiophen-2-yl)-[1,2,4]oxadiazol-3-yl]-6-methyl-phenoxy}-2-hydroxy-propyl)-2-hydroxy-acetamide and the appropriate amines.

| Example | R | LC-MS $t_R$ [min] | $[M + H]^+$ |
|---|---|---|---|
| 50 | HN-iPr | 0.81 | 517.20 |
| 51 | N(CH3)CH2CH3 | 0.76 | 489.13 |
| 52 | N(CH3)CH2CH3 | 0.77 | 503.11 |
| 53 | N(CH3)CH2CH2CH3 | 0.80 | 517.19 |
| 54 | N(CH3)(CH2)3CH3 | 0.82 | 531.09 |
| 55 | N(CH3)CH2CH(CH3)2 | 0.81 | 531.12 |
| 56 | N(CH2CH3)2 | 0.79 | 517.19 |
| 57 | N(CH2CH3)CH2CH2CH3 | 0.81 | 531.10 |
| 58 | N(iPr)CH2CH3 | 0.80 | 531.06 |
| 59 | N(CH2CH3)(CH2)3CH3 | 0.84 | 545.11 |
| 60 | azetidinyl | 0.77 | 501.12 |

Example 51

¹H NMR (D₆-DMSO): δ1.22 (t, J=7.3 Hz, 3H), 2.23 (s, 3H), 2.27 (s, 6H), 2.34 (s, 3H), 2.72 (q, J=7.3 Hz, 2H), 3.22-3.29 (m, 1H), 3.41-3.48 (m, 1H), 3.63 (s, 2H), 3.69-3.80 (m, 2H), 3.84 (s, 2H), 3.92-4.00 (m, 1H), 5.30 (s br, 1H), 5.56 (s br, 1H), 7.69 (t, J=5.5 Hz, 1H), 7.73 (s, 2H), 7.82 (s, 1H).

Example 53

¹H NMR δ0.90 (t, J=7.0 Hz, 3H), 1.22 (t, J=7.3 Hz, 3H), 1.50 (h, J=7.3 Hz, 2H), 2.23 (s, 3H), 2.25 (s, 3H), 2.34 (s, 3H), 2.40 (t, J=7.3 Hz, 2H), 2.72 (q, J=7.3 Hz, 2H), 3.20-3.29 (m, 1H), 3.39-3.48 (m, 1H), 3.68 (s, 2H), 3.71-3.80 (m, 2H), 3.84 (d, J=5.3 Hz, 2H), 3.92-3.99 (m, 1H), 5.30 (d, J=5.0 Hz, 1H), 5.55 (t, J=5.5 Hz, 1H), 7.69 (t, J=5.3 Hz, 1H), 7.73 (s, 2H), 7.82 (s, 1H).

Example 55

¹H NMR δ0.91 (d, J=6.3 Hz, 6H), 1.22 (t, J=7.5 Hz, 3H), 1.77-1.86 (m, 1H), 2.19-2.25 (m, 8H), 2.34 (s, 3H), 2.72 (q, J=7.0 Hz, 2H), 3.20-3.29 (m, 1H), 3.39-3.48 (m, 1H), 3.67 (s, 2H), 3.69-3.80 (m, 2H), 3.84 (d, J=5.5 Hz, 2H), 3.91-4.00 (m,

1H), 5.30 (d, J=5.0 Hz, 1H), 5.54 (t, J=5.5 Hz, 1H), 7.69 (t, J=5.3 Hz, 1H), 7.73 (s, 2H), 7.82 (s, 1H).

Example 56

$^1$H NMR (D$_6$-DMSO): δ1.04 (t, J=7.0 Hz, 6H), 1.22 (t, J=7.5 Hz, 3H), 2.22 (s, 3H), 2.34 (s, 3H), 2.58 (q, J=7.0 Hz, 4H), 2.72 (q, J=7.3 Hz, 2H), 3.21-3.29 (m, 1H), 3.39-3.47 (m, 1H), 3.69-3.79 (m, 4H), 3.84 (d, J=5.5 Hz, 2H), 3.92-4.00 (m, 1H), 5.30 (d, J=5.3 Hz, 1H), 5.55 (t, J=5.5 Hz, 1H), 7.70 (t, J=5.8 Hz, 1H), 7.74 (s, 2H), 7.81 (s, 1H).

Examples 61 to 71

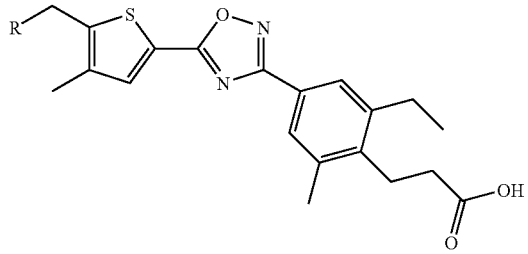

The following examples are prepared according to Method C starting from 3-{2-ethyl-4-[5-(5-formyl-4-methyl-thiophen-2-yl)-[1,2,4]oxadiazol-3-yl]-6-methyl-phenyl}-propionic acid ethyl ester and the appropriate amines to give the ethyl ester of the desired products. The ethyl ester is then cleaved by dissolving the compound in methanol and 1 N aq. NaOH. The mixture is stirred at rt for 16 h before it is acidified with formic acid and separated by prep. HPLC (XBride Prep C18, 30×75 mm, 5 μm, 10% to 95% acetonitrile in water containing 0.5% of formic acid) to give the desired 3-{4-[5-(5-aminomethyl-4-methyl-thiophen-2-yl)-[1,2,4]oxadiazol-3-yl]-2-ethyl-6-methyl-phenyl}-propionic acid derivatives.

| | | LC-MS | |
|---|---|---|---|
| Example | R | t$_R$ [min] | [M + H]$^+$ |
| 61 | HN⟨iPr⟩ | 0.90 | 442.15 |
| 62 | N(Me) | 0.85 | 414.02 |
| 63 | N(Et) | 0.86 | 428.09 |
| 64 | N(nPr) | 0.89 | 442.11 |
| 65 | N(nBu) | 0.92 | 456.18 |
| 66 | N(iPr) | 0.91 | 456.15 |

| | | LC-MS | |
|---|---|---|---|
| Example | R | t$_R$ [min] | [M + H]$^+$ |
| 67 | N(Et)$_2$ | 0.88 | 442.12 |
| 68 | N(Et)(nPr) | 0.90 | 456.11 |
| 69 | N(Et)(iPr) | 0.90 | 456.13 |
| 70 | N(Et)(nBu) | 0.93 | 470.14 |
| 71 | azetidine | 0.86 | 426.05 |

Example 62

$^1$H NMR (D$_6$-DMSO): δ1.22 (t, J=7.3 Hz, 3H), 2.23 (s, 3H), 2.27 (s, 6H), 2.36-2.42 (m, 5H), 2.73 (q, J=7.3 Hz, 2H), 2.90-2.97 (m, 2H), 3.63 (s, 2H), 7.69 (s, 2H), 7.83 (s, 1H).

Example 67

$^1$H NMR (D$_6$-DMSO): δ1.04 (t, J=6.8 Hz, 6H), 1.22 (t, J=7.3 Hz, 3H), 2.22 (s, 3H), 2.35-2.43 (m, 5H), 2.58 (q, J=7.0 Hz, 4H), 2.73 (q, J=7.3 Hz, 2H), 2.90-2.97 (m, 2H), 3.73 (s, 2H), 7.69 (s, 2H), 7.81 (s, 1H).

Example 72

3-(2-Ethyl-4-{5-[5-(isobutylamino-methyl)-4-methyl-thiophen-2-yl]-[1,2,4]oxadiazol-3-yl}-6-methyl-phenyl)-propan-1-ol The title compound is isolated as a by-product from the preparation of Example 61; LC-MS: t$_R$=0.91 min; [M+1]$^+$=428.16; $^1$H NMR (D$_6$-DMSO): δ0.91 (d, J=6.3 Hz, 6H), 1.22 (t, J=7.3 Hz, 3H), 1.55-1.64 (m, 2H), 1.66-1.77 (m, 1H), 2.21 (s, 3H), 2.36-2.44 (m, 5H), 2.66-2.77 (m, 4H), 3.48-3.55 (m, 2H), 3.89 (s, 2H), 4.59 (s br, 1H), 7.68 (s, 1H), 7.69 (s, 1H), 7.81 (s, 1H).

Examples 73 to 76

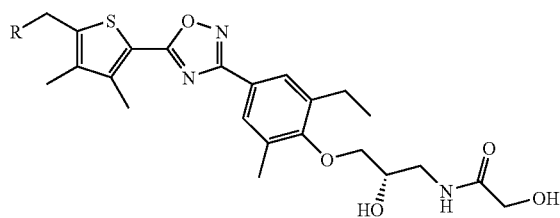

The following examples are prepared according to Method C starting from N—((S)-3-{2-ethyl-4-[5-(5-formyl-3,4-dimethyl-thiophen-2-yl)-[1,2,4]oxadiazol-3-yl]-6-methyl-phenoxy}-2-hydroxy-propyl)-2-hydroxy-acetamide and the appropriate amines.

| Example | R | LC-MS** $t_R$ [min] | $[M + H]^+$ |
|---|---|---|---|
| 73 | N— | 0.50 | 503.15 |
| 74 | N—propyl | 0.54 | 531.16 |
| 75 | N—isobutyl | 0.56 | 545.21 |
| 76 | N—diethyl | 0.53 | 531.22 |

Examples 77 to 80

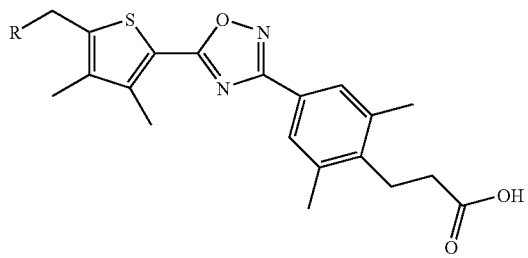

The following examples are prepared according to Method C starting from 3-{4-[5-(5-formyl-3,4-dimethyl-thiophen-2-yl)-[1,2,4]oxadiazol-3-yl]-2,6-dimethyl-phenyl}-propionic acid and the appropriate amines.

| Example | R | LC-MS** $t_R$ [min] | $[M + H]^+$ |
|---|---|---|---|
| 77 | N— | 0.59 | 428.18 |
| 78 | N—propyl | 0.63 | 456.18 |
| 79 | N—isobutyl | 0.66 | 470.16 |
| 80 | N—diethyl | 0.62 | 456.19 |

Examples 81 and 82

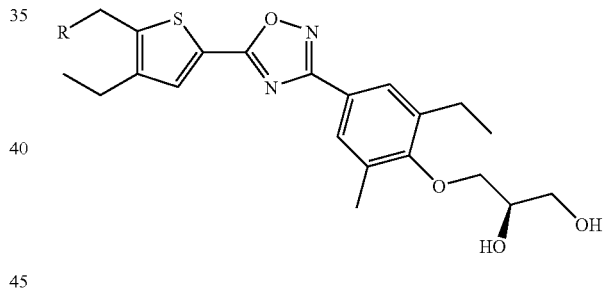

Starting from (S)-5-{3-[4-(2,2-dimethyl-[1,3]dioxolan-4-ylmethoxy)-3-ethyl-5-methyl-phenyl]-[1,2,4]oxadiazol-5-yl}-3-ethyl-thiophene-2-carbaldehyde and the appropriate amines the following Examples are prepared according to Method C:

| Example | R | LC-MS $t_R$ [min] | $[M + H]^+$ |
|---|---|---|---|
| 81 | N— | 0.53 | 446.18 |
| 82 | N—propyl | 0.57 | 474.27 |

Examples 83 and 84

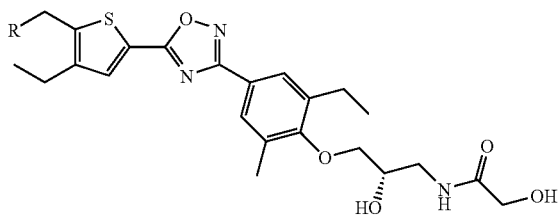

Starting from N—((S)-3-{2-ethyl-4-[5-(4-ethyl-5-formyl-thiophen-2-yl)-[1,2,4]oxadiazol-3-yl]-6-methyl-phenoxy}-2-hydroxy-propyl)-2-hydroxy-acetamide and the appropriate amines the following Examples are prepared according to Method C:

| Example | R | LC-MS $t_R$ [min] | [M + H]$^+$ |
|---------|---|---|---|
| 83 | ⌬N | 0.51 | 503.28 |
| 84 | ⌬N | 0.54 | 531.31 |

Examples 85 and 86

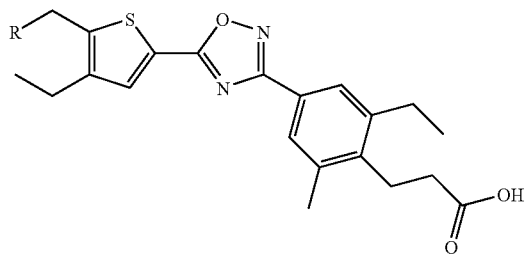

Starting from 3-{2-ethyl-4-[5-(4-ethyl-5-formyl-thiophen-2-yl)-[1,2,4]oxadiazol-3-yl]-6-methyl-phenyl}-propionic acid ethyl ester and the appropriate amines the following Examples are prepared according to Method C:

| Example | R | LC-MS $t_R$ [min] | [M + H]$^+$ |
|---------|---|---|---|
| 85 | ⌬N | 0.59 | 428.23 |
| 86 | ⌬N | 0.63 | 456.28 |

Example 85

$^1$H NMR (D$_6$-DMSO): δ1.19 (t, J=7.5 Hz, 3H), 1.22 (t, J=7.5 Hz, 3H), 2.27 (s, 6H), 2.32-2.38 (m, 2H), 2.40 (s, 3H), 2.63 (q, J=7.3 Hz, 2H), 2.73 (q, J=7.5 Hz, 2H), 2.90-2.96 (m, 2H), 3.65 (s, 2H), 7.70 (s, 2H), 7.88 (s, 1H).

Example 86

$^1$H NMR (D$_6$-DMSO): δ0.90 (t, J=7.5 Hz, 3H), 1.19 (t, J=7.3 Hz, 3H), 1.22 (t, J=7.5 Hz, 3H), 1.47-1.56 (m, 2H), 2.25 (s, 3H), 2.30-2.37 (m, 2H), 2.38-2.44 (m, 5H), 2.62 (q, J=7.3 Hz, 2H), 2.73 (q, J=7.3 Hz, 2H), 2.89-2.96 (m, 2H), 3.70 (s, 2H), 7.69 (s, 2H), 7.87 (s, 1H)

Example 87

N-((2S)-3-{4-[5-(5-Dimethylaminomethyl-4-methyl-thiophen-2-yl)-[1,2,4]oxadiazol-3-yl]-2,6-dimethyl-phenoxy}-2-hydroxy-propyl)-2-hydroxy-acetamide The title compound (165 mg) is obtained as a pale yellow foam following Method C starting from (2S)—N-(3-{4-[5-(5-formyl-4-methyl-thiophen-2-yl)-[1,2,4]oxadiazol-3-yl]-2,6-dimethyl-phenoxy}-2-hydroxy-propyl)-2-hydroxy-acetamide (210 mg, 0.471 mmol) and dimethyl amine (4.78 mL of a 2 M solution in THF); LC-MS: $t_R$=0.45 min; [M+1]$^+$=475.12; $^1$H NMR (D$_6$-DMSO): δ2.23 (s, 3H), 2.27 (s, 6H), 2.33 (s, 6H), 3.20-3.28 (m, 1H), 3.40-3.48 (m, 1H), 3.63 (s, 2H), 3.72 (dd, J=9.5, 6.0 Hz, 1H), 3.78 (dd, J=9.5, 4.5 Hz, 1H), 3.84 (d, J=5.5 Hz, 2H), 3.91-3.99 (m, 1H), 5.29 (d, J=5.3 Hz, 1H), 5.55 (t, J=5.5 Hz, 1H), 7.69 (t br, J=5.8 Hz, 1H), 7.72 (s, 2H), 7.82 (s, 1H).

Examples 88 to 91

The following Examples are prepared in analogy to Example 87:

| Example | R | LC-MS $t_R$ [min] | [M + H]$^+$ |
|---------|---|---|---|
| 88 | ⌬N | 1.05* | 517.11 |
| 89 | ⌬N | 1.08* | 517.10 |
| 90 | ⌬N | 1.07* | 517.12 |

| Example | R | LC-MS $t_R$ [min] | $[M+H]^+$ |
|---|---|---|---|
| 91 | (structure: HN-CH(CH$_3$)-CH$_3$ branched, isopropylamino) | 0.88* | 488.97 |

Example 91

$^1$H NMR (D$_6$-DMSO): δ1.05 (d, J=6.3 Hz, 6H), 2.22 (s, 3H), 2.33 (s, 6H), 2.78-2.84 (m, 1H), 3.20-3.28 (m, 1H), 3.40-3.47 (m, 1H), 3.72 (dd, J=9.8, 6.0 Hz, 1H), 3.78 (dd, J=9.8, 4.5 Hz, 1H), 3.84 (d, J=5.8 Hz, 2H), 3.89 (s, 2H), 3.92-3.98 (m, 1H), 5.29 (d, J=5.3 Hz, 1H), 5.55 (t, J=5.8 Hz, 1H), 7.69 (t, J=6.0 Hz, 1H), 7.72 (s, 2H), 7.79 (s, 1H).

Example 92

N-{(2S)-3-[4-(5-{5-[(Ethyl-isopropyl-amino)-methyl]-4-methyl-thiophen-2-yl}-[1,2,4]oxadiazol-3-yl)-2,6-dimethyl-phenoxy]-2-hydroxy-propyl}-2-hydroxy-acetamide A solution of 2-hydroxy-N-[(2S)-2-hydroxy-3-(4-{5-[5-(isopropylamino-methyl)-4-methyl-thiophen-2-yl]-[1,2,4]oxadiazol-3-yl}-2,6-dimethyl-phenoxy)-propyl]-acetamide (284 mg, 0.448 mmol, Example 91), ethyl iodide (423 mg, 2.69 mmol) and DIPEA (354 mg, 2.69 mmol) in DMF (3 mL) is stirred at rt for 1 h, then at 40° C. for 17 h before another portion of DIPEA (54 mg, 0.421 mmol) and ethyl iodide (304 mg, 1.95 mmol) is added. Stirring is continued at 40° C. for 20 h. The mixture is diluted with aq. sat. NH$_3$ (1 mL) and separated by prep. HPLC (Waters XBridge Prep C18, 75×30 mm ID, 10 μm, gradient of acetonitrile in water containing 0.5% of sat. aq. NH$_3$) to give the title compound (94 mg) as a colourless resin; LC-MS*: $t_R$=1.08 min; $[M+1]^+$=517.32.

Example 93

N-{(2S)-3-[2-Ethyl-4-(5-{5-[(ethyl-isobutyl-amino)-methyl]-4-methyl-thiophen-2-yl}-[1,2,4]oxadiazol-3-yl)-6-methyl-phenoxy]-2-hydroxy-propyl}-2-hydroxy-acetamide The title compound (66 mg) is obtained as a colourless resin in analogy to Example 92 starting from N-{(2S)-3-[2-ethyl-4-(5-{5-[(isobutyl-amino)-methyl]-4-methyl-thiophen-2-yl}-[1,2,4]oxadiazol-3-yl)-6-methyl-phenoxy]-2-hydroxy-propyl}-2-hydroxy-acetamide (212 mg, 0.328 mmol, Example 50); LC-MS*: $t_R$=1.17 min; $[M+1]^+$=545.09; $^1$H NMR (D$_6$-DMSO): δ0.92 (d, J=6.5 Hz, 6H), 1.02 (t, J=7.0 Hz, 3H), 1.22 (t, J=7.5 Hz, 3H), 1.73-1.84 (m, 1H), 2.22 (s, 3H), 2.25 (t, J=7.3 Hz, 2H), 2.34 (s, 3H), 2.50-2.56 (m, 2H), 2.72 (q, J=7.5 Hz, 2H), 3.21-3.29 (m, 1H), 3.39-3.47 (m, 1H), 3.70-3.79 (m, 4H), 3.84 (d, J=5.5 Hz, 2H), 3.92-4.00 (m, 1H), 5.30 (d, J=5.3 Hz, 1H), 5.55 (t, J=5.8 Hz, 1H), 7.70 (t, J=5.8 Hz, 1H), 7.73 (s, 2H), 7.81 (s, 1H).

Example 94

3-[2-Ethyl-4-(5-{5-[(isopropyl-methyl-amino)-methyl]-4-methyl-thiophen-2-yl}-[1,2,4]oxadiazol-3-yl)-6-methyl-phenyl]-propionic acid a) 3-[2-Ethyl-4-(5-{5-[(isopropyl-methyl-amino)-methyl]-4-methyl-thiophen-2-yl}-[1,2,4]oxadiazol-3-yl)-6-methyl-phenyl]-propionic acid ethyl ester formate salt (86 mg) is obtained as a pale yellow oil starting from 3-{2-ethyl-4-[5-(5-formyl-4-methyl-thiophen-2-yl)-[1,2,4]oxadiazol-3-yl]-6-methyl-phenyl}-propionic acid ethyl ester (100 mg, 0.242 mmol) and N-isopropyl-methylamine (709 mg, 9.70 mmol) using two portions of sodium triacetoxyborohydride (171 mg, 0.727 mmol) and following Method C; LC-MS: $t_R$=0.71 min; $[M+1]^+$=470.15; $^1$H NMR (D$_6$-DMSO): δ1.05 (d, J=6.5 Hz, 6H), 1.17-1.26 (m, 6H), 2.23 (s, 6H), 2.39 (s, 3H), 2.44-2.50 (m, 2H), 2.72 (q, J=7.5 Hz, 2H), 2.89-3.01 (m, 3H), 3.70 (s, 2H), 4.10 (q, J=7.0 Hz, 2H), 7.69 (s, 2H), 7.80 (s, 1H), 8.15 (s, 1H).

b) A solution of the above propionic acid ethyl ester (75 mg, 0.145 mmol) in ethanol (1.5 mL) and 2 N aq. NaOH (1.5 mL) is stirred at rt for 6 h. The ethanol is evaporated and the reaction mixture is acidified by adding formic acid before it is separated be prep. HPLC (column: Atlantis T3 C18, 30×75 mm, 10 μm, eluting with a gradient of acetonitrile in water containing 0.5% of formic acid) to give the title compound (62 mg) as its formate salt as a pale yellow solid; LC-MS*: $t_R$=0.66 min; $[M-1]^-$=440.02; $^1$H NMR (D$_6$-DMSO): δ1.05 (d, J=6.5 Hz, 6H), 1.22 (t, J=7.3 Hz, 3H), 2.23 (s, 6H), 2.33-2.42 (m, 5H), 2.73 (q, J=7.5 Hz, 2H), 2.89-2.97 (m, 3H), 3.70 (s, 2H), 7.69 (s, 2H), 7.80 (s, 1H), 8.17 (s, 1H).

Example 95

{3-[2-Ethyl-4-(5-{5-[(isopropyl-methyl-amino)-methyl]-4-methyl-thiophen-2-yl}-[1,2,4]oxadiazol-3-yl)-6-methyl-phenyl]-propionylamino}-acetic acid ethyl ester To a solution of 3-[2-ethyl-4-(5-{5-[(isopropyl-methyl-amino)-methyl]-4-methyl-thiophen-2-yl}-[1,2,4]oxadiazol-3-yl)-6-methyl-phenyl]-propionic acid formate salt (9 mg, 18 μmol) in DMF (1 mL), DIPEA (14.3 mg, 0.111 mmol) and TBTU (7 mg, 20 μmol) is added. The mixture is stirred for 5 min before glycine ethyl ester hydrochloride (3.9 mg, 28 μmol) is added. The mixture is stirred at rt for 1 h before it is separated by prep. HPLC to give the title compound (8 mg) as a pale yellow resin; LC-MS: $t_R$=0.61 min; $[M-1]^-$=527.19.

Example 96

{3-[2-Ethyl-4-(5-{5-[(isopropyl-methyl-amino)-methyl]-4-methyl-thiophen-2-yl}-[1,2,4]oxadiazol-3-yl)-6-methyl-phenyl]-propionylamino}-acetic acid A solution of {3-[2-ethyl-4-(5-{5-[(isopropyl-methyl-amino)-methyl]-4-methyl-thiophen-2-yl}-[1,2,4]oxadiazol-3-yl)-6-methyl-phenyl]-propionylamino}-acetic acid ethyl ester (5 mg, 9 μmol) in ethanol (500 μL) and 1 N aq. NaOH (100 μL) is stirred at rt for 1 h before it is concentrated, diluted with formic acid (1 mL) and separated by prep. HPLC (column: Atlantis T3 C18, 30×75 mm, 10 μm, eluting with a gradient of acetonitrile in water containing 0.5% of formic acid) to give the title compound (4 mg) as a resin; LC-MS*: $t_R$=0.66 min; $[M+1]^+$=498.97, $^1$H NMR (D$_6$-DMSO): δ 1.05 (d, J=6.5 Hz, 6H), 1.23 (t, J=7.3 Hz, 3H), 2.23 (s, 6H), 2.28-2.35 (m, 2H), 2.41 (s, 3H), 2.74 (q, J=7.5 Hz, 2H), 2.87-2.98 (m, 3H), 3.70 (s, 2H), 3.76 (d, J=5.5 Hz, 2H), 7.69 (s, 2H), 7.81 (s, 1H), 8.23 (t br, J=5.5 Hz).

Examples 97 to 102

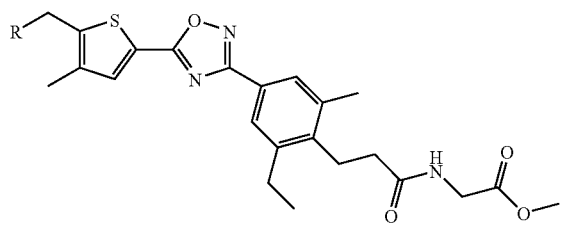

The following Examples are prepared in analogy to Example 95 starting from the appropriate 3-[2-ethyl-4-(5-{5-[(mono or di-alkylamino)-methyl]-4-methyl-thiophen-2-yl}-[1,2,4]oxadiazol-3-yl)-6-methyl-phenyl]-propionic acid and glycine methyl ester hydrochloride.

| | | LC-MS | |
|---|---|---|---|
| Example | R | $t_R$ [min] | $[M + H]^+$ |
| 97 | N— | 0.55 | 485.19 |
| 98 | N— | 0.59 | 513.24 |
| 99 | N— | 0.58 | 513.14 |
| 100 | N— | 0.61 | 527.23 |
| 101 | N | 0.58 | 513.19 |
| 102 | N | 0.60 | 527.18 |

Examples 103 to 107

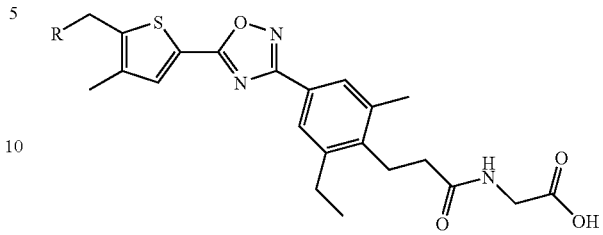

The following Examples are prepared in analogy to Example 96 starting from the appropriate (3-{4-[5-(5-(mono- or di-alkyl-aminomethyl-4-methyl-thiophen-2-yl)-[1,2,4]oxadiazol-3-yl]-2-ethyl-6-methyl-phenyl}-propionylamino)-acetic acid methyl ester.

| | | LC-MS | |
|---|---|---|---|
| Example | R | $t_R$ [min] | $[M + H]^+$ |
| 103 | N— | 0.51 | 471.15 |
| 104 | N— | 0.55 | 499.31 |
| 105 | N— | 0.57 | 513.19 |
| 106 | N | 0.54 | 499.11 |
| 107 | N | 0.56 | 513.21 |

Examples 108 to 113

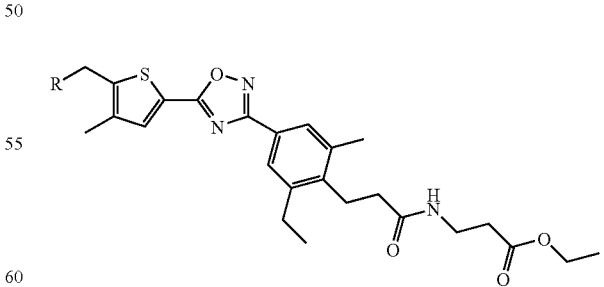

The following Examples are prepared in analogy to Example 95 starting from the appropriate 3-[2-ethyl-4-(5-{5-[(mono- or di-alkylamino)-methyl]-4-methyl-thiophen-2-yl}-[1,2,4]oxadiazol-3-yl)-6-methyl-phenyl]-propionic acid and 3-amino-propionic acid ethyl ester hydrochloride.

| Example | R | LC-MS t_R [min] | [M + H]+ |
|---|---|---|---|
| 108 | N(CH3)(CH3) | 0.59 | 513.22 |
| 109 | N(CH3)CH2CH2CH3 | 0.62 | 541.25 |
| 110 | N(CH3)CH(CH3)2 | 0.61 | 541.30 |
| 111 | N(CH3)CH2CH(CH3)2 | 0.65 | 555.20 |
| 112 | N(CH2CH3)2 | 0.61 | 541.21 |
| 113 | N(CH2CH2CH3)CH3 (piperidine-like) | 0.64 | 555.21 |

Examples 114 to 119

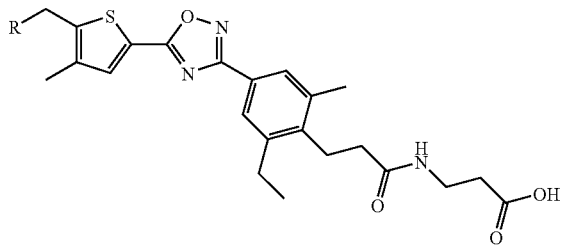

The following Examples are prepared in analogy to Example 96 starting from the appropriate 3-(3-{4-[5-(5-mono- or di-alkyl-aminomethyl-4-methyl-thiophen-2-yl)-[1,2,4]oxadiazol-3-yl]-2-ethyl-6-methyl-phenyl}-propionylamino)-propionic acid ethyl ester.

| Example | R | LC-MS t_R [min] | [M + H]+ |
|---|---|---|---|
| 114 | N(CH3)(CH3) | 0.52 | 485.12 |
| 115 | N(CH3)CH2CH2CH3 | 0.55 | 513.26 |
| 116 | N(CH3)CH(CH3)2 | 0.54 | 513.19 |
| 117 | N(CH3)CH2CH(CH3)2 | 0.57 | 527.27 |
| 118 | N(CH2CH3)2 | 0.54 | 513.23 |
| 119 | N(CH2CH2CH3)CH3 | 0.56 | 527.22 |

Examples 120 to 125

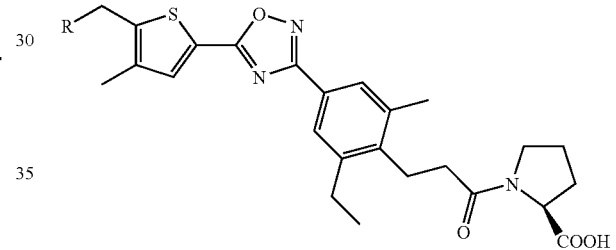

The following Examples are prepared following the procedure given in Example 95 followed by the procedure given in Example 96 starting from the appropriate 3-[2-ethyl-4-(5-{5-[(mono- or di-alkylamino)-methyl]-4-methyl-thiophen-2-yl}-[1,2,4]oxadiazol-3-yl)-6-methyl-phenyl]-propionic acid and (S)-pyrrolidine-2-carboxylic acid methyl ester.

| Example | R | LC-MS t_R [min] | [M + H]+ |
|---|---|---|---|
| 120 | N(CH3)(CH3) | 0.55 | 511.15 |
| 121 | N(CH3)CH2CH2CH3 | 0.59 | 539.10 |
| 122 | N(CH3)CH(CH3)2 | 0.58 | 539.23 |
| 123 | N(CH3)CH2CH(CH3)2 | 0.61 | 553.23 |

| Example | R | LC-MS $t_R$ [min] | [M + H]$^+$ |
|---|---|---|---|
| 124 | | 0.58 | 539.19 |
| 125 | | 0.60 | 553.18 |

Examples 126 to 131

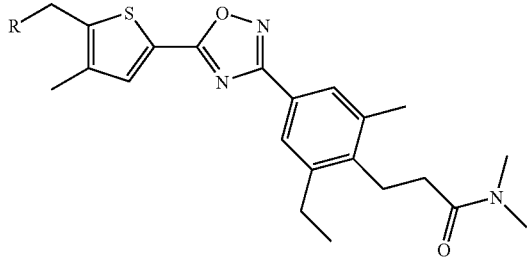

The following Examples are prepared in analogy to Example 95 starting from the appropriate 3-[2-ethyl-4-(5-{5-[(mono- or di-alkylamino)-methyl]-4-methyl-thiophen-2-yl}-[1,2,4]oxadiazol-3-yl)-6-methyl-phenyl]-propionic acid and dimethylamine.

| Example | R | LC-MS $t_R$ [min] | [M + H]$^+$ |
|---|---|---|---|
| 126 | | 0.57 | 441.28 |
| 127 | | 0.61 | 469.14 |
| 128 | | 0.59 | 469.09 |
| 129 | | 0.63 | 483.34 |
| 130 | | 0.60 | 469.13 |

| Example | R | LC-MS $t_R$ [min] | [M + H]$^+$ |
|---|---|---|---|
| 131 | | 0.62 | 483.12 |

Examples 132 to 137

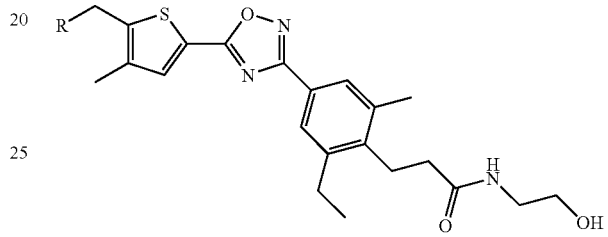

The following Examples are prepared in analogy to Example 95 starting from the appropriate 3-[2-ethyl-4-(5-{5-[(mono- or di-alkylamino)-methyl]-4-methyl-thiophen-2-yl}-[1,2,4]oxadiazol-3-yl)-6-methyl-phenyl]-propionic acid and ethanolamine.

| Example | R | LC-MS $t_R$ [min] | [M + H]$^+$ |
|---|---|---|---|
| 132 | | 0.50 | 457.16 |
| 133 | | 0.53 | 485.13 |
| 134 | | 0.52 | 485.00 |
| 135 | | 0.56 | 499.35 |
| 136 | | 0.52 | 485.19 |
| 137 | | 0.55 | 499.07 |

Examples 138 to 143

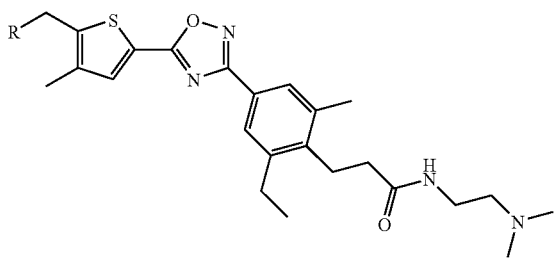

The following Examples are prepared in analogy to Example 95 starting from the appropriate 3-[2-ethyl-4-(5-{5-[(mono- or di-alkylamino)-methyl]-4-methyl-thiophen-2-yl}-[1,2,4]oxadiazol-3-yl)-6-methyl-phenyl]-propionic acid and N,N-dimethyl-ethylene-diamine.

| Example | R | LC-MS $t_R$ [min] | $[M + H]^+$ |
|---|---|---|---|
| 138 | N/ | 0.45 | 483.75 |
| 139 | N/\ | 0.48 | 512.14 |
| 140 | N/(iPr) | 0.47 | 512.24 |
| 141 | N/(iBu) | 0.50 | 526.25 |
| 142 | N(Et)2 | 0.47 | 512.27 |
| 143 | N(Et)(Pr) | 0.49 | 526.21 |

Examples 144 to 147

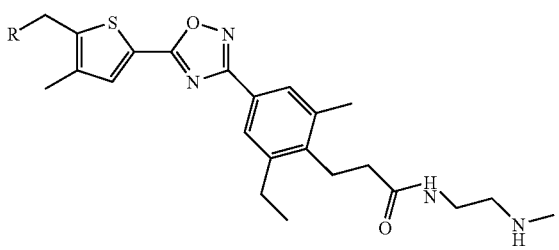

The appropriate 3-[2-ethyl-4-(5-{5-[(mono- or di-alkylamino)-methyl]-4-methyl-thiophen-2-yl}-[1,2,4]oxadiazol-3-yl)-6-methyl-phenyl]-propionic acid (57 µmol) is reacted with N-Boc-N-methyl-ethylene-diamine (15 mg, 86 µmol) in analogy to the procedure given for Example 95. The thus obtained Boc-protected intermediate is then treated with TFA (1.5 mL) in DCM (1.5 mL) at rt for 18 h before it is purified by prep. HPLC (XBridge Prep C18, 30×75 mm, 10 um, eluting with a gradient of acetonitrile in water containing 0.5% of formic acid). The product containing fractions are concentrated, dissolved in methanol and filtered over Amberlyst-A21 (200 mg). The filtrate is evaporated and dried to give the desired compound as a almost colourless resin.

| Example | R | LC-MS $t_R$ [min] | $[M + H]^+$ |
|---|---|---|---|
| 144 | N/ | 0.45 | 470.19 |
| 145 | N/\ | 0.48 | 498.22 |
| 146 | N/(iPr) | 0.47 | 498.24 |
| 147 | N/(iBu) | 0.50 | 512.18 |

Example 146

$^1$H NMR (D$_6$-DMSO): δ1.05 (d, J=6.8 Hz, 6H), 1.23 (t, J=7.3 Hz, 3H), 2.23 (s, 6H), 2.25-2.31 (m, 2H), 2.41 (s, 3H), 2.48 (s, 3H), 2.74 (q, J=7.5 Hz, 2H), 2.81 (t, J=6.3 Hz, 2H), 2.87-2.97 (m, 3H), 3.22-3.31 (m, 2H), 3.70 (s, 2H), 7.69 (s, 2H), 7.80 (s, 1H), 8.05 (t, J=5.5 Hz, 1H).

Examples 148 and 149

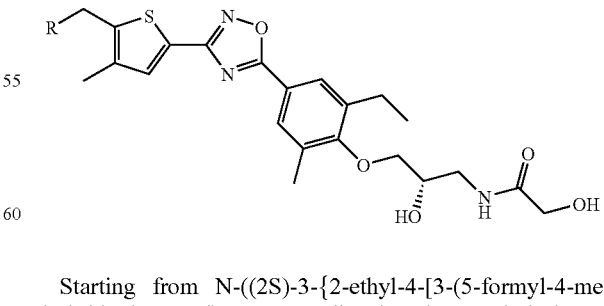

Starting from N-((2S)-3-{2-ethyl-4-[3-(5-formyl-4-methyl-thiophen-2-yl)-[1,2,4]oxadiazol-5-yl]-6-methyl-phenoxy}-2-hydroxy-propyl)-2-hydroxy-acetamide and the appropriate amines, the following Examples are prepared according to Method C:

| Example | R | LC-MS $t_R$ [min] | [M + H]$^+$ |
|---|---|---|---|
| 148 | (structure) | 0.85* | 488.92 |
| 149 | (structure) | 0.99* | 517.08 |

Example 148

$^1$H NMR (D$_6$-DMSO): δ1.23 (t, J=7.3 Hz, 3H), 2.22 (s, 3H), 2.25 (s, 6H), 2.36 (s, 3H), 2.75 (q, J=7.3 Hz, 2H), 3.21-3.30 (m, 1H), 3.43 (m, 1H), 3.58 (s, 2H), 3.72-3.82 (m, 2H), 3.84 (d, J=5.8 Hz, 2H), 3.94-4.00 (m, 1H), 5.32 (d, J=5.3 Hz, 1H), 5.55 (t, J=5.8 Hz, 1H), 7.61 (s, 1H), 7.70 (t, J=5.8 Hz, 1H), 7.85 (s, 1H), 7.86 (s, 1H).

Example 150

N-((2S)-3-{4-[5-(5-Dimethylaminomethyl-4-methyl-thiophen-2-yl)-[1,3,4]oxadiazol-2-yl]-2-ethyl-6-methyl-phenoxy}-2-hydroxy-propyl)-2-hydroxy-acetamide The title compound (4 mg) is prepared starting from N-((2S)-3-{2-ethyl-4-[5-(5-formyl-4-methyl-thiophen-2-yl)-[1,3,4]oxadiazol-2-yl]-6-methyl-phenoxy}-2-hydroxy-propyl)-2-hydroxy-acetamide (12 mg, 26 μmol) and dimethylamine (14 mg, 105 μmol) according to Method C; LC-MS*: $t_R$=0.80 min; [M+1]$^+$=488.95; $^1$H NMR (D$_6$-DMSO): δ1.23 (t, J=7.5 Hz, 3H), 2.23 (s, 3H), 2.26 (s, 6H), 2.35 (s, 3H), 2.73 (q, J=7.5 Hz, 2H), 3.21-3.29 (m, 1H), 3.39-3.47 (m, 1H), 3.61 (s, 2H), 3.71-3.81 (m, 2H), 3.84 (d, J=3.3 Hz, 2H), 3.93-4.00 (m, 1H), 5.31 (d, J=5.3 Hz, 1H), 5.55 (t, J=5.5 Hz, 1H), 7.68-7.72 (m, 2H), 7.77 (s, 2H).

Example 151

4-[5-(5-Diethylaminomethyl-4-methyl-thiophen-2-yl)-[1,2,4]oxadiazol-3-yl]-2-ethyl-6-methyl-phenol The title compound (17 mg) is obtained as orange oil according to Method A starting from 5-diethylaminomethyl-4-methyl-thiophene-2-carboxylic acid (125 mg, 0.552 mmol) and 3-ethyl-4,N-dihydroxy-5-methyl-benzamidine (118 mg, 0.607 mmol); LC-MS: $t_R$=0.61 min; [M+1]$^+$=385.70; $^1$H NMR (CDCl$_3$): δ1.11 (t, J=7.3 Hz, 6H), 1.32 (t, J=7.5 Hz, 3H), 2.25 (s, 3H), 2.34 (s, 3H), 2.63 (q, J=7.0 Hz, 4H), 2.72 (q, J=7.5 Hz, 2H), 3.73 (s, 2H), 7.66 (s, 1H), 7.81 (s, 2H).

Example 152

{4-[5-(5-Diethylaminomethyl-4-methyl-thiophen-2-yl)-[1,2,4]oxadiazol-3-yl]-phenyl}-methanol The title compound (1.12 g) is obtained as a beige powder according to Method A starting from 5-diethylaminomethyl-4-methyl-thiophene-2-carboxylic acid (1.40 g, 6.16 mmol) and N-hydroxy-4-hydroxymethyl-benzamidine (1.13 g, 6.81 mmol); LC-MS: $t_R$=0.49 min; [M+1]$^+$=358.13; $^1$H NMR (CDCl$_3$): δ1.11 (t, J=7.0 Hz, 6H), 2.26 (s, 3H), 2.63 (q, J=7.3 Hz, 4H), 3.73 (s, 2H), 4.80 (s, 2H), 7.51 (d, J=8.0 Hz, 2H), 7.67 (s, 1H), 8.15 (d, J=8.3 Hz, 2H).

Example 153

{5-[3-(4-Aminomethyl-phenyl)-[1,2,4]oxadiazol-5-yl]-3-methyl-thiophen-2-ylmethyl}-diethyl-amine a) To a solution of {4-[5-(5-diethylaminomethyl-4-methyl-thiophen-2-yl)-[1,2,4]oxadiazol-3-yl]-phenyl}-methanol (971 mg, 2.72 mmol) in DCM (40 mL), DIPEA (526 mg, 4.07 mmol) and methanesulfonyl chloride (373 mg, 3.26 mmol) is added. The reaction mixture is stirred at rt for 15 h before it is diluted with DCM and washed with sat. aq. NaHCO$_3$ solution. The washing is extracted back three times with DCM. The combined organic extracts are dried over MgSO$_4$, filtered, concentrated and dried to give crude methanesulfonic acid 4-[5-(5-diethylaminomethyl-4-methyl-thiophen-2-yl)-[1,2,4]oxadiazol-3-yl]-benzyl ester (1.48 g) as an orange solid containing {5-[3-(4-chloromethyl-phenyl)-[1,2,4]oxadiazol-5-yl]-3-methyl-thiophen-2-ylmethyl}-diethyl-amine; LC-MS: $t_R$=0.58 min; [M+1]$^+$=436.11.

b) A solution of the above crude methanesulfonic acid 4-[5-(5-diethylaminomethyl-4-methyl-thiophen-2-yl)-[1,2,4]oxadiazol-3-yl]-benzyl ester (248 mg, 0.569 mmol) in 7 N NH$_3$ in methanol (10 mL) is stirred in a sealed vial at 80° C. for 16 h. The solvent is removed in vacuo and the residue is dissolved in EA and washed with brine and water. The organic extract is dried over MgSO$_4$, filtered and concentrated. The crude product is purified on prep. TLC plates with DCM containing 5% of 7N NH$_3$ in methanol to give the title compound (137 mg) as a pale yellow oil; LC-MS: $t_R$=0.38 min; [M+1]$^+$=357.30; $^1$H NMR (CDCl$_3$): δ 1.11 (t, J=7.0 Hz, 6H), 2.26 (s, 3H), 2.64 (q, J=7.0 Hz, 4H), 3.73 (s, 2H), 3.98 (s, 2H), 7.47 (d, J=7.8 Hz, 2H), 7.67 (s, 1H), 8.13 (d, J=7.5 Hz, 2H).

Example 154

2-{4-[5-(5-Diethylaminomethyl-4-methyl-thiophen-2-yl)-[1,2,4]oxadiazol-3-yl]-benzylamino}-ethanol The title compound (113 mg) is obtained as a yellow oil in analogy to Example 153, step b), starting from methanesulfonic acid 4-[5-(5-diethylaminomethyl-4-methyl-thiophen-2-yl)-[1,2,4]oxadiazol-3-yl]-benzyl ester (260 mg, 0.597 mmol) and ethanolamine (146 mg, 2.39 mmol); LC-MS: $t_R$=0.39 min; [M+1]$^+$=401.25; $^1$H NMR (CDCl$_3$): δ 1.12 (t, J=7.0 Hz, 6H), 2.26 (s, 3H), 2.64 (q, J=7.0 Hz, 4H), 2.87 (t, J=5.3 Hz, 2H), 3.71 (t, J=4.8 Hz, 2H), 3.73 (s, 2H), 3.92 (s, 2H), 7.48 (d, J=7.8 Hz, 2H), 7.68 (s, 1H), 8.13 (d, J=7.8 Hz, 2H).

Example 155

N-{4-[5-(5-Diethylaminomethyl-4-methyl-thiophen-2-yl)-[1,2,4]oxadiazol-3-yl]-benzyl}-methanesulfonamide To a solution of {5-[3-(4-aminomethyl-phenyl)-[1,2,4]oxadiazol-5-yl]-3-methyl-thiophen-2-ylmethyl}-diethyl-amine (60 mg, 168 μmol) and DIPEA (33 mg, 252 μmol) in DCM (10 mL), methanesulfonyl chloride (23 mg, 202 μmol) is added. The mixture is stirred at rt for 15 h before it is diluted with DCM and washed with sat. aq. NaHCO$_3$ solution. The washing is extracted back three times with DCM, the organic extracts are combined, dried over MgSO$_4$, filtered and concentrated. The crude product is purified by prep. HPLC. The product containing fractions are combined and concentrated. The product is dissolved in methanol and filtered over Amberlyst A21. The filtrate is evaporated and dried to give the title compound (10 mg) as a colourless resin; LC-MS: $t_R$=0.52 min; [M+1]$^+$=435.03; $^1$H NMR (CDCl$_3$): δ1.14 (t, J=7.0 Hz, 6H), 2.27 (s, 3H), 2.68 (q, J=6.8 Hz, 4H), 2.93 (s, 3H), 3.79 (s, 2H), 4.42 (d, J=5.8 Hz, 2H), 5.04-5.10 (m, 1H), 7.51 (d, J=8.3 Hz, 2H), 7.68 (s, 1H), 8.15 (d, J=8.3 Hz, 2H).

Example 156

4-[5-(5-Diethylaminomethyl-4-methyl-thiophen-2-yl)-[1,2,4]oxadiazol-3-yl]-N-(2-hydroxy-ethyl)-benzenesulfonamide Starting from N-hydroxy-4-(2-hydroxy-ethylsulfamoyl)-benzamidine (201 mg, 0.774 mmol) and 5-diethylaminomethyl-4-methyl-thiophene-2-carboxylic acid (160 mg, 0.704 mmol), the title compound (29 mg) is obtained as a yellow oil according to Method A; LC-MS: $t_R$=0.49 min; [M+1]$^+$=451.02; $^1$H NMR (CDCl$_3$): δ1.27 (t, J=7.3 Hz, 6H), 2.34 (s, 3H), 2.91 (q, J=7.3 Hz, 4H), 3.17-3.22 (m, 2H), 3.73-3.77 (m, 2H), 4.11 (s, 2H), 7.74 (s, 1H), 8.01-8.04 (m, 2H), 8.24 (s br, 1H), 8.30-8.33 (m, 2H).

Example 157

{4-[5-(5-Diethylaminomethyl-4-methyl-thiophen-2-yl)-[1,2,4]oxadiazol-3-yl]-benzenesulfonylamino}-acetic acid {4-[5-(5-Diethylaminomethyl-4-methyl-thiophen-2-yl)-[1,2,4]oxadiazol-3-yl]-benzenesulfonylamino}-acetic acid ethyl ester (98 mg) is obtained starting from [4-(N-hydroxycarbamimidoyl)-benzenesulfonylamino]-acetic acid ethyl ester (233 mg, 0.774 mmol) and 5-diethylaminomethyl-4-methyl-thiophene-2-carboxylic acid (160 mg, 0.704 mmol) according to Method A; LC-MS: $t_R$=0.57 min; [M+1]$^+$=493.17. This material (98 mg, 199 μmol) is dissolved in 2 N aq. LiOH (25 mL) and methanol (25 mL). The mixture is stirred at rt for 20 h before it is acidified by adding 1 N aq. HCl and extracted twice with EA. The combined organic extracts are dried over MgSO$_4$, filtered and concentrated. The crude product is purified by prep. HPLC to give the title compound (6 mg) as a white solid; LC-MS: $t_R$=0.50 min; [M+1]$^+$=465.02.

Example 158

N-(2-Amino-ethyl)-4-[5-(5-diethylaminomethyl-4-methyl-thiophen-2-yl)-[1,2,4]oxadiazol-3-yl]-benzenesulfonamide Crude (2-{4-[5-(5-diethylaminomethyl-4-methyl-thiophen-2-yl)-[1,2,4]oxadiazol-3-yl]-benzenesulfonylamino}-ethyl)-carbamic acid tert-butyl ester (156 mg) is obtained starting from {2-[4-(N-hydroxycarbamimidoyl)-benzenesulfonylamino]-ethyl}-carbamic acid tert-butyl ester (277 mg, 0.774 mmol) and 5-diethylaminomethyl-4-methyl-thiophene-2-carboxylic acid (160 mg, 0.704 mmol) according to Method A; LC-MS: $t_R$=0.61 min; [M+1]$^+$=550.16. This material (156 mg, 0.284 mmol) is dissolved in 4 M HCl in dioxane (5 mL) and the mixture is stirred at rt for 18 h. The mixture is diluted with water and washed with EA. The organic washing is extracted with water. The combined aq. extracts are neutralised by adding sat. aq. NaHCO$_3$ solution and extracted twice with EA. These organic extracts are combined, dried over MgSO$_4$, filtered and concentrated. The crude product is purified by prep. HPLC (XBridge, eluting with a gradient of acetonitrile in water containing 0.5% of aq. ammonia) to give the title compound (11 mg) as a pale yellow oil; LC-MS: $t_R$=0.42 min; [M+1]$^+$=449.64.

Example 159

2-{4-[5-(5-Diethylaminomethyl-4-methyl-thiophen-2-yl)-[1,2,4]oxadiazol-3-yl]-phenyl}-ethanol The title compound (267 mg) is obtained as a yellow oil following Method A and starting from N-hydroxy-4-(2-hydroxy-ethyl)-benzamidine (1.25 g, 6.93 mmol) and 5-diethylaminomethyl-4-methyl-thiophene-2-carboxylic acid (1.50 g, 6.60 mmol); LC-MS: $t_R$=0.52 min; [M+1]$^+$=372.11; $^1$H NMR (CDCl$_3$): δ1.11 (t, J=7.0 Hz, 6H), 2.25 (s, 3H), 2.56-2.69 (m, 4H), 2.96 (t, J=6.5 Hz, 2H), 3.72 (s, 2H), 3.93 (t, J=6.5 Hz, 2H), 7.37 (d, J=7.8 Hz, 2H), 7.66 (s, 1H), 8.09 (d, J=7.5 Hz, 2H).

Example 160

2-{4-[5-(5-Diethylaminomethyl-4-methyl-thiophen-2-yl)-[1,2,4]oxadiazol-3-yl]-phenyl}-ethylamine a) To a cooled (0° C.) solution of 2-{4-[5-(5-diethylaminomethyl-4-methyl-thiophen-2-yl)-[1,2,4]oxadiazol-3-yl]-phenyl}-ethanol (196 mg, 488 μmol) and DIPEA (84 mg, 732 μmol) in THF (5 mL), methanesulfonyl chloride (126 mg, 976 μmol) is added as a solution in THF (2.5 mL). The reaction mixture is stirred at 0° C. for 1 h, then at rt for 1 h. The mixture is diluted with DCM (100 mL) and washed with brine (3×50 mL). The organic extract is dried over MgSO$_4$, filtered, concentrated and dried to give crude methanesulfonic acid 2-{4-[5-(5-diethylaminomethyl-4-methyl-thiophen-2-yl)-[1,2,4]oxadiazol-3-yl]-phenyl}-ethyl ester (295 mg); LC-MS: $t_R$=0.59 min; [M+1]$^+$=449.71.

b) A solution of methanesulfonic acid 2-{4-[5-(5-diethylaminomethyl-4-methyl-thiophen-2-yl)-[1,2,4]oxadiazol-3-yl]-phenyl}-ethyl ester (295 mg, 658 μmol) in 7 N NH$_3$ in methanol (10 mL) is stirred in a sealed vessel at 80° C. for 16 h. The reaction mixture is concentrated and dried to give the title compound (255 mg) as a pale yellow oil; LC-MS: $t_R$=0.64 min; [M+1]$^+$=370.97.

Example 161

(2-{4-[5-(5-Diethylaminomethyl-4-methyl-thiophen-2-yl)-[1,2,4]oxadiazol-3-yl]-phenyl}-ethyl)-methyl-amine The title compound (3 mg) is obtained as a pale yellow solid in analogy to Example 160 starting from methanesulfonic acid 2-{4-[5-(5-diethylaminomethyl-4-methyl-thiophen-2-yl)-[1,2,4]oxadiazol-3-yl]-phenyl}-ethyl ester (50 mg, 111 μmol) and 2 M methylamine in THF (4 mL); LC-MS: $t_R$=0.63 min; [M+1]$^+$=385.03; $^1$H NMR (CDCl$_3$): δ1.11 (t, J=7.0 Hz, 6H), 2.26 (s, 3H), 2.53 (s, 2H), 2.63 (q, J=7.3 Hz, 4H), 2.89-3.08 (m, 53H), 3.73 (s, 2H), 7.36 (d, J=8.0 Hz, 2H), 7.66 (s, 1H), 8.09 (d, J=8.3 Hz, 2H).

Example 162

2-(2-{4-[5-(5-Diethylaminomethyl-4-methyl-thiophen-2-yl)-[1,2,4]oxadiazol-3-yl]-phenyl}-ethylamino)-ethanol The title compound (6 mg) is prepared in analogy to Example 160 starting from methanesulfonic acid 2-{4-[5-(5-diethylaminomethyl-4-methyl-thiophen-2-yl)-[1,2,4]oxadiazol-3-yl]-phenyl}-ethyl ester (50 mg, 111 µmol) and ethanolamine (34 mg, 556 µmol); LC-MS: $t_R$=0.63 min; $[M+1]^+$=415.07; $^1$H NMR (CDCl$_3$): δ1.11 (t, J=7.0 Hz, 6H), 2.26 (s, 3H), 2.63 (q, J=7.0 Hz, 4H), 2.80-2.86 (m, 2H), 2.87-2.93 (m, 2H), 2.94-3.00 (m, 2H), 3.62-3.67 (m, 2H), 3.73 (s, 2H), 7.35 (d, J=8.0 Hz, 2H), 7.67 (s, 1H), 8.09 (d, J=8.0 Hz, 2H).

Example 163

N-(2-{4-[5-(5-Diethylaminomethyl-4-methyl-thiophen-2-yl)-[1,2,4]oxadiazol-3-yl]-phenyl}-ethyl)-2-hydroxy-acetamide To a solution of glycolic acid (15 mg, 202 µmol) and DIPEA (35 mg, 270 µmol) in DMF (5 mL) is added HOBt (27 mg, 202 µmol) and EDC hydrochloride (39 mg, 202 µmol) at 0° C. The mixture is stirred for 15 min at 0° C. Then 2-{4-[5-(5-diethylaminomethyl-4-methyl-thiophen-2-yl)-[1,2,4]oxadiazol-3-yl]-phenyl}-ethylamine is added and stirring is continued for 1 h at 0° C. The reaction is quenched with water, diluted with sat. aq. NaHCO$_3$ and the mixture is extracted three times with EA. The combined organic extracts are dried over MgSO$_4$, filtered and concentrated. The crude product is purified on prep. TLC plates using DCM containing 10% of 7 N NH$_3$ in methanol to give the title compound (4 mg) as a colourless oil; LC-MS: $t_R$=0.69 min; $[M+1]^+$=429.06.

Example 164

N-(2-{4-[5-(5-Diethylaminomethyl-4-methyl-thiophen-2-yl)-[1,2,4]oxadiazol-3-yl]-phenyl}-ethyl)-3-hydroxy-propionamide The title compound (3 mg) is prepared in analogy to Example 163 by coupling 2-{4-[5-(5-diethylaminomethyl-4-methyl-thiophen-2-yl)-[1,2,4]oxadiazol-3-yl]-phenyl}-ethylamine (50 mg, 135 µmol) with 3-hydroxypropionic acid (18 mg, 202 µmol); LC-MS: $t_R$=0.71 min; $[M+1]^+$=442.76.

Example 165

N-(2-{4-[5-(5-Diethylaminomethyl-4-methyl-thiophen-2-yl)-[1,2,4]oxadiazol-3-yl]-phenyl}-ethyl)-2-methylamino-acetamide

[(2-{4-[5-(5-Diethylaminomethyl-4-methyl-thiophen-2-yl)-[1,2,4]oxadiazol-3-yl]-phenyl}-ethylcarbamoyl)-methyl]-methyl-carbamic acid tert-butyl ester is prepared in analogy to Example 163 by coupling 2-{4-[5-(5-diethylaminomethyl-4-methyl-thiophen-2-yl)-[1,2,4]oxadiazol-3-yl]-phenyl}-ethylamine (20 mg, 54 µmol) with (tert-butoxycarbonyl-methyl-amino)-acetic acid (15 mg, 81 µmol); LC-MS: $t_R$=0.84 min; $[M+1]^+$=542.20; $^1$H NMR (CDCl$_3$): δ1.16 (m, 6H), 1.44 (s, 9H), 2.27 (s, 3H), 2.88 (s, 3H), 2.90-2.99 (m, 2H), 3.61 (q, J=6.5 Hz, 2H), 3.75 (s br, 1H), 3.85 (s, 2H), 7.34 (d, J=8.0 Hz, 2H), 7.67 (s, 1H), 8.10 (d, J=8.0 Hz, 2H). This material (18 mg, 30 µmol) is dissolved in DCM (2 mL) and TFA (50 µL) is added. The mixture is stirred at rt for 18 h before it is diluted with EA and washed with sat. aq. NaHCO$_3$ solution. The organic extract is dried over Na$_2$SO$_4$, filtered and concentrated. The crude product is purified by prep. HPLC and on prep. TLC plates with DCM containing 10% of 7 N NH$_3$ in methanol to give the title compound (12 mg) as a colourless solid; LC-MS: $t_R$=0.64 min; $[M+1]^+$=442.00.

Example 166

N-(2-{4-[5-(5-Diethylaminomethyl-4-methyl-thiophen-2-yl)-[1,2,4]oxadiazol-3-yl]-phenyl}-ethyl)-methanesulfonamide The title compound (3 mg) is prepared in analogy to Example 155 starting from 2-{4-[5-(5-diethylaminomethyl-4-methyl-thiophen-2-yl)-[1,2,4]oxadiazol-3-yl]-phenyl}-ethylamine (10 mg, 27 µmol) and methanesulfonyl chloride (4 mg, 35 µmol); LC-MS: $t_R$=0.78 min; $[M+1]^+$=448.99; $^1$H NMR (CDCl$_3$): δ 1.11 (t, J=7.0 Hz, 6H), 2.26 (s, 3H), 2.64 (q, J=7.3 Hz, 4H), 2.89 (s, 3H), 2.96-3.01 (m, 2H), 3.49 (q, J=6.8 Hz, 2H), 3.73 (s, 2H), 4.23 (t br, J=6.3 Hz, 1H), 7.37 (d, J=8.0 Hz, 2H), 7.67 (s, 1H), 8.13 (d, J=8.3 Hz, 2H).

Example 167 rac-3-{4-[5-(5-Diethylaminomethyl-4-methyl-thiophen-2-yl)-[1,2,4]oxadiazol-3-yl]-phenyl}-propane-1,2-diol a) {5-[3-(4-Allyl-phenyl)-[1,2,4]oxadiazol-5-yl]-3-methyl-thiophen-2-ylmethyl}-diethyl-amine (625 mg) is obtained as a yellow oil starting from 5-diethylaminomethyl-4-methyl-thiophene-2-carboxylic acid (1.50 g, 6.60 mmol) and 4-allyl-N-hydroxy-benzamidine (1.28 g, 7.26 mmol) according to Method A; LC-MS: $t_R$=0.64 min; $[M+1]^+$=368.20.

b) To a solution of {5-[3-(4-allyl-phenyl)-[1,2,4]oxadiazol-5-yl]-3-methyl-thiophen-2-ylmethyl}-diethyl-amine (550 mg, 1.50 mmol) in acetone (7.5 mL) and water (0.5 mL), OsO$_4$ (38 mg, as a 2.5% solution in butanol) followed by N-methyl morpholine-N-oxide (243 mg, 1.80 mmol) is added. The mixture is stirred at rt for 16 h. The clear yellow solution is diluted with DCM, washed with water (3×50 mL), dried over MgSO$_4$, filtered, concentrated and dried to give crude title compound (619 mg) as yellow oil; LC-MS: $t_R$=0.48 min; $[M+1]^+$=401.70; $^1$H NMR (CDCl$_3$): δ1.11 (t, J=7.0 Hz, 6H), 2.25 (s, 3H), 2.63 (q, J=7.3 Hz, 4H), 2.84-2.92 (m, 2H), 3.55 (dd, J=11.0, 7.0 Hz, 1H), 3.69-3.76 (m, 4H), 3.96-4.04 (m, 1H), 7.37 (d, J=7.8 Hz, 2H), 7.66 (s, 1H), 8.08 (d, J=7.8 Hz, 2H).

Example 168 rac-1-Amino-3-{4-[5-(5-diethylaminomethyl-4-methyl-thiophen-2-yl)-[1,2,4]oxadiazol-3-yl]-phenyl}-propan-2-ol a) To a cooled (0° C.) solution of rac-3-{4-[5-(5-diethylaminomethyl-4-methyl-thiophen-2-yl)-[1,2,4]oxadiazol-3-yl]-phenyl}-propane-1,2-diol (619 mg, 1.54 mmol) in THF (15 mL), DIPEA (399 mg, 3.08 mmol) followed by methansulfonyl chloride (247 mg, 2.16 mmol) is added. The mixture is stirred at 0° C. for 1 h, then at rt for 1 h. The mixture is diluted with DCM, washed with brine (3×50 mL), dried over MgSO$_4$, filtered, concentrated and dried to give crude rac-methanesulfonic acid 3-{4-[5-(5-diethylaminomethyl-4-methyl-thiophen-2-yl)-[1,2,4]oxadiazol-3-yl]-phenyl}-2-hydroxy-propyl ester (955 mg) as a light brown oil; LC-MS: $t_R$=0.54 min; [M+1]$^+$=480.10.

b) A solution of the above rac-methanesulfonic acid 3-{4-[5-(5-diethylaminomethyl-4-methyl-thiophen-2-yl)-[1,2,4]oxadiazol-3-yl]-phenyl}-2-hydroxy-propyl ester (600 mg, 1.33 mmol) in 7 M NH$_3$ in methanol (10 mL) is stirred in a sealed vessel at 80° C. for 16 h. The mixture is diluted with EA and washed with water and brine. The organic extract is dried over MgSO$_4$, filtered and concentrated. The crude product is purified on prep. TLC plates using DCM containing 10% of methanol to give the title compound (242 mg) as a pale yellow resin; LC-MS: $t_R$=0.63 min; [M+1]$^+$=400.93.

Example 169 rac-N-(3-{4-[5-(5-Diethylaminomethyl-4-methyl-thiophen-2-yl)-[1,2,4]oxadiazol-3-yl]-phenyl}-2-hydroxy-propyl)-2-hydroxy-acetamide The title compound (31 mg) is prepared in analogy to Example 163 starting from rac-1-amino-3-{4-[5-(5-diethylaminomethyl-4-methyl-thiophen-2-yl)-[1,2,4]oxadiazol-3-yl]-phenyl}-propan-2-ol (50 mg, 125 μmol) and glycolic acid (13 mg, 175 μmol); LC-MS: $t_R$=0.68 min; [M+1]$^+$=458.68. $^1$H NMR (CDCl$_3$): δ1.09 (t, J=7.0 Hz, 6H), 2.23 (s, 3H), 2.62 (q, J=7.0 Hz, 4H), 2.75-2.87 (m, 2H), 3.18-3.28 (m, 1H), 3.50-3.58 (m, 1H), 3.70 (s, 2H), 3.94-4.02 (m, 1H), 4.06 (s, 2H), 7.14 (t, J=5.5 Hz, 1H), 7.33 (d, J=8.3 Hz, 2H), 7.64 (s, 1H), 8.03 (d, J=8.0 Hz, 2H).

Example 170 rac-N-(3-{4-[5-(5-Diethylaminomethyl-4-methyl-thiophen-2-yl)-[1,2,4]oxadiazol-3-yl]-phenyl}-2-hydroxy-propyl)-methanesulfonamide The title compound (12 mg) is obtained as a pale yellow oil in analogy to Example 155 starting from rac-1-amino-3-{4-[5-(5-diethylaminomethyl-4-methyl-thiophen-2-yl)-[1,2,4]oxadiazol-3-yl]-phenyl}-propan-2-ol (25 mg, 62 μmol) and methansulfonyl chloride (9 mg, 75 μmol); LC-MS: $t_R$=0.73 min; [M+1]$^+$=479.07; $^1$H NMR (CDCl$_3$): δ1.11 (t, J=7.0 Hz, 6H), 2.25 (s, 3H), 2.63 (q, J=7.0 Hz, 4H), 2.85 (dd, J=13.6, 8.3 Hz, 1H), 2.93 (dd, J=13.8, 4.8 Hz, 1H), 3.01 (s, 3H), 3.10-3.18 (m, 1H), 3.34-3.41 (m, 1H), 3.72 (s, 2H), 4.05-4.13 (m, 1H), 4.84 (t, J=6.0 Hz, 1H), 7.36 (d, J=8.0 Hz, 2H), 7.67 (s, 1H), 8.11 (d, J=8.3 Hz, 2H).

Example 171 rac-N-(3-{4-[5-(5-Diethylaminomethyl-4-methyl-thiophen-2-yl)-[1,2,4]oxadiazol-3-yl]-phenyl}-2-hydroxy-propyl)-sulfamic acid dimethyl-amide The title compound (21 mg) is prepared in analogy to Example 166 starting from rac-1-amino-3-{4-[5-(5-diethylaminomethyl-4-methyl-thiophen-2-yl)-[1,2,4]oxadiazol-3-yl]-phenyl}-propan-2-ol (50 mg, 125 μmol) and dimethylsulfamoyl chloride (22 mg, 150 μmol); LC-MS: $t_R$=0.76 min; [M+1]$^+$=508.18; $^1$H NMR (CDCl$_3$): δ1.11 (t, J=7.0 Hz, 6H), 2.25 (s, 3H), 2.64 (q, J=7.0 Hz, 4H), 2.83 (s, 6H), 2.85-2.94 (m, 2H), 3.03-3.10 (m, 1H), 3.24-3.30 (m, 1H), 3.73 (s, 2H), 4.04-4.11 (m, 1H), 7.37 (d, J=8.3 Hz, 2H), 7.66 (s, 1H), 8.10 (d, J=8.3 Hz, 2H).

Example 172 rac-1-{4-[5-(5-Diethylaminomethyl-4-methyl-thiophen-2-yl)-[1,2,4]oxadiazol-3-yl]-phenyl}-3-(2-hydroxy-ethylamino)-propan-2-ol The title compound (16 mg) is prepared starting from rac-methanesulfonic acid 3-{4-[5-(5-diethylaminomethyl-4-methyl-thiophen-2-yl)-[1,2,4]oxadiazol-3-yl]-phenyl}-2-hydroxy-propyl ester (100 mg, 208 μmol) and ethanolamine (64 mg, 1.04 mmol) in analogy to Example 168 step b); LC-MS: $t_R$=0.63 min; [M+1]$^+$=445.07; $^1$H NMR (CDCl$_3$): δ1.10 (t, J=7.0 Hz, 6H), 2.25 (s, 3H), 2.53 (s br, 2H), 2.59-2.67 (m, 5H), 2.77-2.90 (m, 5H), 3.69 (t, J=5.0 Hz, 2H), 3.72 (s, 2H), 3.95-4.03 (m, 1H), 7.37 (d, J=8.3 Hz, 2H), 7.66 (s, 1H), 8.08 (d, J=8.0 Hz, 2H).

Example 173

4-[5-(5-Dimethylaminomethyl-4-methyl-thiophen-2-yl)-[1,3,4]thiadiazol-2-yl]-2-ethyl-6-methyl-phenol The title compound (13 mg) is prepared staring from 5-[5-(3-ethyl-4-hydroxy-5-methyl-phenyl)-[1,3,4]thiadiazol-2-yl]-3-methyl-thiophene-2-carbaldehyde (21 mg, 61 μmol) and dimethylamine (33 mg, 244 μmol, as a 33% solution in ethanol) according to Method C; LC-MS: $t_R$=0.56 min; [M+1]$^+$=374.07; $^1$H NMR (D$_6$-DMSO): δ1.18 (t, J=7.3 Hz, 3H), 2.20 (s, 3H), 2.24 (s, 6H), 2.26 (s, 3H), 2.67 (q, J=7.3 Hz, 2H), 3.57 (s, 2H), 7.47 (s, 1H), 7.56 (s, 2H).

Example 174

2-{4-[5-(5-Dimethylaminomethyl-4-methyl-thiophen-2-yl)-[1,3,4]thiadiazol-2-yl]-2-ethyl-6-methyl-phenoxy}-ethanol a) To a suspension of 5-[5-(3-ethyl-4-hydroxy-5-methyl-phenyl)-[1,3,4]thiadiazol-2-yl]-3-methyl-thiophene-2-carbaldehyde (54 mg, 157 μmol) and K$_2$CO$_3$ (65 mg, 470 μmol) in acetonitrile (10 mL), (2-bromoethoxy)-tert.-butyl-dimethyl silane (66 mg, 274 μmol) is added. The mixture is stirred at 70° C. for 2 h before another portion of (2-bromoethoxy)-tert.-butyl-dimethyl silane (66 mg, 274 μmol) is added. Stirring is continued at 60° C. for 16 h. The mixture is cooled to rt, acidified by adding 1 N aq. HCl (2 mL) and stirred at rt for 10 min. The reaction mixture is concentrated to a volume of about 1 mL, is diluted with DMF (1.5 mL) and is then separated by prep. HPLC (XBridge Rp C18, 30×75 mm, eluting with a gradient of acetonitrile in water containing 0.5% of aq. ammonia) to give 5-{5-[3-ethyl-4-(2-hydroxy-ethoxy)-5-methyl-phenyl]-[1,3,4]thiadiazol-2-yl}-3-methyl-thiophene-2-carbaldehyde (33 mg) as a pale yellow resin; LC-MS: $t_R$=0.69 min; [M+1]$^+$=429.06.

b) The title compound (24 mg) is obtained as a colourless resin starting from the above 5-{5-[3-ethyl-4-(2-hydroxy-ethoxy)-5-methyl-phenyl]-[1,3,4]thiadiazol-2-yl}-3-methyl-thiophene-2-carbaldehyde (33 mg, 85 μmol) and dimethylamine (46 mg, 340 μmol); LC-MS*: $t_R$=0.96 min; [M+1]$^+$=418.01; $^1$H NMR (D$_6$-DMSO): δ1.22 (t, J=7.5 Hz, 3H), 2.20 (s, 3H), 2.25 (s, 6H), 2.34 (s, 3H), 2.74 (q, J=7.5 Hz, 2H), 3.58 (s, 2H), 3.72-3.77 (m, 2H), 3.85 (t, J=4.5 Hz, 2H), 4.92 (t, J=5.5 Hz, 1H), 7.52 (s, 1H), 7.67 (s, 2H).

Examples 175 to 180

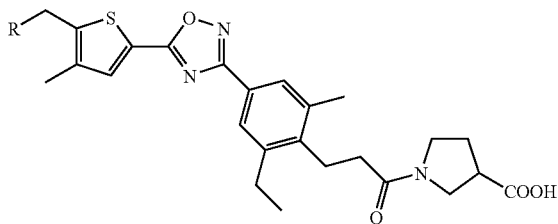

The following Examples are prepared following the procedure given in Example 95 followed by the procedure given in Example 96 starting from the appropriate 3-[2-ethyl-4-(5-{5-[(mono- or di-alkylamino)-methyl]-4-methyl-thiophen-2-yl}-[1,2,4]oxadiazol-3-yl)-6-methyl-phenyl]-propionic acid and pyrrolidine-3-carboxylic acid methyl ester.

| Example | R | LC-MS $t_R$ [min] | $[M + H]^+$ |
|---------|---|-------------------|-------------|
| 175 | N– | 0.53 | 511.14 |
| 176 | N–CH₂CH₃ | 0.57 | 539.23 |
| 177 | N–iPr | 0.56 | 539.20 |
| 178 | N–iBu | 0.59 | 553.12 |
| 179 | N(Et)₂ | 0.56 | 539.28 |
| 180 | N(Et)(Pr) | 0.58 | 553.15 |

Example 177

$^1$H NMR (D$_6$-DMSO): δ1.05 (d, J=6.8 Hz, 6H), 1.22 (t, J=7.5 Hz, 3H), 1.92-2.15 (m, 2H), 2.22 (s, 3H), 2.23 (s, 3H), 2.36-2.44 (m, 5H), 2.67-2.76 (m, 2H), 2.87-3.14 (m, 4H), 3.30-3.66 (m, 6H), 3.71 (s, 2H), 7.69 (s, 2H), 7.81 (s, 1H).

Example 180

$^1$H NMR (D$_6$-DMSO): δ0.89 (t, J=7.3 Hz, 3H), 1.03 (t, J=7.0 Hz, 3H), 1.22 (t, J=7.5 Hz, 3H), 1.48 (h, J=7.5 Hz, 2H), 1.98-2.15 (m, 2H), 2.22 (s, 3H), 2.36-2.42 (m, 5H), 2.43-2.48 (m, 3H), 2.57 (q, J=6.8 Hz, 2H), 2.68-2.76 (m, 2H), 2.88-2.94 (m, 2H), 2.98-3.14 (m, 1H), 3.32-3.66 (m, 5H), 3.74 (s, 2H), 7.69 (s, 2H), 7.81 (s, 1H).

Examples 181 to 186

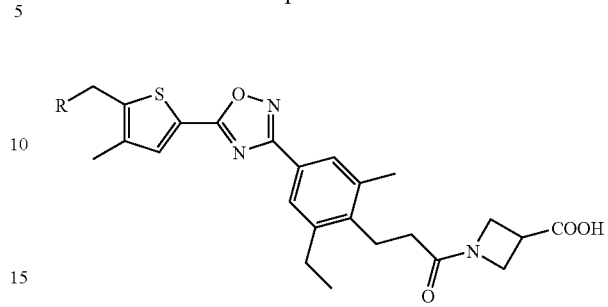

The following Examples are prepared following the procedure given in Example 95 followed by the procedure given in Example 96 starting from the appropriate 3-[2-ethyl-4-(5-{5-[(mono- or di-alkylamino)-methyl]-4-methyl-thiophen-2-yl}-[1,2,4]oxadiazol-3-yl)-6-methyl-phenyl]-propionic acid and azetidine-3-carboxylic acid methyl ester.

| Example | R | LC-MS $t_R$ [min] | $[M + H]^+$ |
|---------|---|-------------------|-------------|
| 181 | N– | 0.52 | 497.25 |
| 182 | N–CH₂CH₃ | 0.55 | 525.27 |
| 183 | N–iPr | 0.54 | 525.28 |
| 184 | N–iBu | 0.57 | 539.30 |
| 185 | N(Et)₂ | 0.54 | 525.14 |
| 186 | N(Et)(Pr) | 0.57 | 539.18 |

Example 182

$^1$H NMR (D$_6$-DMSO): δ0.90 (t, J=7.3 Hz, 3H), 1.22 (t, J=7.5 Hz, 3H), 1.51 (h, J=7.0 Hz, 2H), 2.18-2.22 (m, 2H), 2.23 (s, 3H), 2.25 (s, 3H), 2.39 (s, 3H), 2.40-2.43 (m, 2H), 2.72 (q, J=7.5 Hz, 2H), 2.84-2.90 (m, 2H), 3.35-3.42 (m, 1H), 3.69 (s, 2H), 3.90 (dd, J=9.5, 5.8 Hz, 1H), 4.03 (t, J=9.3 Hz, 1H), 4.12 (dd, J=8.5, 6.0 Hz, 1H), 4.23 (t, J=9.0 Hz, 1H), 7.69 (s, 2H), 7.82 (s, 1H).

Example 185

$^1$H NMR (D$_6$-DMSO): δ1.04 (t, J=7.0 Hz, 6H), 1.22 (t, J=7.3 Hz, 3H), 2.18-2.26 (m, 5H), 2.39 (s, 3H), 2.58 (q, J=7.0

Hz, 4H), 2.72 (q, J=7.8 Hz, 2H), 2.82-2.90 (m, 2H), 3.36-3.43 (m, 1H), 3.74 (s, 2H), 3.90 (dd, J=9.5, 6.0 Hz, 1H), 4.03 (t, J=9.3 Hz, 1H), 4.12 (dd, J=8.0, 6.0 Hz, 1H), 4.24 (t, J=8.8 Hz, 1H), 7.69 (s, 2H), 7.81 (s, 1H).

Example 187

2-Chloro-4-[5-(5-diethylaminomethyl-4-methyl-thiophen-2-yl)-[1,2,4]oxadiazol-3-yl]-6-methyl-phenylamine The title compound (20 mg) is prepared starting from 5-diethylaminomethyl-4-methyl-thiophene-2-carboxylic acid (100 mg, 440 µmol) and 4-amino-3-chloro-N-hydroxy-5-methyl-benzamidine (97 mg, 484 µmol) according to Method A; LC-MS: $t_R$=0.61 min; [M+1]$^+$=391.08; $^1$H NMR (CDCl$_3$): δ1.11 (t, J=7.0 Hz, 6H), 2.25 (s, 3H), 2.29 (s, 3H), 2.57-2.70 (m, 4H), 3.72 (s, 2H), 7.65 (s, 1H), 7.78 (s, 1H), 7.98 (d, J=1.5 Hz, 1H).

Example 188

N-{2-Chloro-4-[5-(5-diethylaminomethyl-4-methyl-thiophen-2-yl)-[1,2,4]oxadiazol-3-yl]-6-methyl-phenyl}-2-hydroxy-acetamide A solution of benzyloxyacetyl chloride (142 mg, 767 µmol) in DCM (2 mL) is added to a solution of 2-chloro-4-[5-(5-diethylaminomethyl-4-methyl-thiophen-2-yl)-[1,2,4]oxadiazol-3-yl]-6-methyl-phenylamine (30 mg, 77 µmol) in DCM (2 mL). The mixture is stirred at rt for 15 h. The mixture is diluted with diethyl ether and washed with 1 N aq. HCl. The organic extract is washed with 33% aq. KOH solution, dried over MgSO$_4$, filtered and concentrated. The crude product is purified by reverse phase MPLC to give 2-benzyloxy-N-{2-chloro-4-[5-(5-diethylaminomethyl-4-methyl-thiophen-2-yl)-[1,2,4]oxadiazol-3-yl]-6-methyl-phenyl}-acetamide (12 mg) as a pale yellow oil; LC-MS: $t_R$=0.68 min; [M+1]$^+$=529.18. The material is dissolved in THF:ethanol 1:1 (5 mL) and Pd/C (10 mg, 10% Pd) is added. The mixture is stirred at rt for 15 h under 5 bar of H$_2$. The catalyst is removed by filtration and the filtrate is concentrated. The crude product is purified on prep. TLC plates with DCM containing 4% of methanol to give the title compound (4 mg) as a white solid; LC-MS: $t_R$=0.50 min; [M+1]$^+$=448.98; $^1$H NMR (CD$_3$OD): δ 1.13 (t, J=7.0 Hz, 6H), 2.29 (s, 3H), 2.39 (s, 3H), 2.66 (q, J=6.8 Hz, 4H), 3.80 (s, 2H), 4.24 (s, 2H), 7.75 (s, 1H), 8.00 (s, 1H), 8.06 (s, 1H).

Example 189

4-[5-(5-Diethylaminomethyl-4-methyl-thiophen-2-yl)-[1,2,4]oxadiazol-3-yl]-N-(2-hydroxy-ethyl)-benzamide a) 4-[5-(5-Diethylaminomethyl-4-methyl-thiophen-2-yl)-[1,2,4]oxadiazol-3-yl]-benzoic acid ethyl ester (1.42 g) is prepared starting from 4-(N-hydroxycarbamimidoyl)-benzoic acid ethyl ester (1.01 g, 4.84 mmol) and 5-diethylaminomethyl-4-methyl-thiophene-2-carboxylic acid (1.00 g, 4.40 mmol) according to Method A; LC-MS: $t_R$=0.63 min; [M+1]$^+$=400.12; $^1$H NMR (CDCl$_3$): δ 1.11 (t, J=7.0 Hz, 6H), 1.45 (t, J=7.0 Hz, 3H), 2.26 (s, 3H), 2.64 (q, J=7.0 Hz, 4H), 3.73 (s, 2H), 4.44 (q, J=7.3 Hz, 2H), 7.69 (s, 1H), 8.16-8.20 (m, 2H), 8.22-8.25 (m, 2H). This material (1.42 g, 3.58 mmol) is dissolved in 2 M LiOH in methanol (50 mL) and the mixture is stirred at rt for 20 h before it is acidified by adding aq. HCl. The mixture is extracted twice with EA. The combined organic extracts are dried over MgSO$_4$, filtered and concentrated. The crude product is purified by prep. HPLC to give 4-[5-(5-diethylaminomethyl-4-methyl-thiophen-2-yl)-[1,2,4]oxadiazol-3-yl]-benzoic acid (710 mg) as a white solid; LC-MS: $t_R$=0.52 min; [M+1]$^+$=372.14.

b) To a solution of 4-[5-(5-diethylaminomethyl-4-methyl-thiophen-2-yl)-[1,2,4]oxadiazol-3-yl]-benzoic acid (400 mg, 1.08 mmol) in DMF (5 mL), HOBt (160 mg, 1.19 mmol) followed by EDC HCl (227 mg, 1.19 mmol) is added. The mixture is stirred at rt for 5 min before ethanolamine (72 mg, 1.19 mmol) is added. The reaction mixture is stirred at rt for 1 h. The mixture is diluted with EA and washed with sat. aq. NaHCO$_3$. The washing is extracted back twice with EA. The combined organic extracts are dried over MgSO$_4$, filtered and concentrated. The crude product is purified by CC on silica gel eluting with DCM containing 4% of methanol to give the title compound (290 mg) as a white solid; LC-MS: $t_R$=0.47 min; [M+1]$^+$=415.14; $^1$H NMR (CDCl$_3$): δ1.11 (t, J=7.0 Hz, 6H), 2.26 (s, 3H), 2.64 (q, J=7.0 Hz, 4H), 3.67-3.72 (m, 2H), 3.73 (s, 2H), 3.90 (t, J=4.8 Hz, 2H), 6.69 (t br, J=5.3 Hz, 1H), 7.68 (s, 1H), 7.91-7.95 (m, 2H), 8.22-8.26 (m, 2H).

Example 190

4-[5-(5-Diethylaminomethyl-4-methyl-thiophen-2-yl)-[1,2,4]oxadiazol-3-yl]-2-methoxy-6-methyl-phenol The title compound (16 mg) is prepared starting from 5-diethylaminomethyl-4-methyl-thiophene-2-carboxylic acid (30 mg, 130 µmol) and 4,N-dihydroxy-3-methoxy-5-methyl-benzamidine (23 mg, 117 µmol) according to Method A; LC-MS: $t_R$=0.57 min; [M+1]$^+$=387.78.

Example 191

4-[5-(5-Diethylaminomethyl-4-methyl-thiophen-2-yl)-[1,2,4]oxadiazol-3-yl]-2-methyl-6-propyl-phenol The title compound (20 mg) is prepared starting from 5-diethylaminomethyl-4-methyl-thiophene-2-carboxylic acid (30 mg, 130 µmol) and 4,N-dihydroxy-3-propyl-5-methyl-benzamidine (24 mg, 117 µmol) according to Method A; LC-MS: $t_R$=0.64 min; [M+1]$^+$=400.22; $^1$H NMR (D$_6$-DMSO): δ0.94 (t, J=7.3 Hz, 3H), 1.03 (t, J=7.0 Hz, 6H), 1.53-1.64 (m, 2H), 2.22 (s, 3H), 2.26 (s, 2H), 2.57 (q, J=7.0 Hz, 4H), 2.61-2.66 (m, 2H), 3.73 (s, 2H), 7.59-7.62 (m, 1H), 7.62-7.65 (m, 1H), 7.78 (s, 1H), 8.88 (s br, 1H).

Example 192

2-Chloro-4-[5-(5-diethylaminomethyl-4-methyl-thiophen-2-yl)-[1,2,4]oxadiazol-3-yl]-6-methyl-phenol The title compound (11 mg) is prepared starting from 5-diethylaminomethyl-4-methyl-thiophene-2-carboxylic acid (30 mg, 130 µmol) and 4,N-dihydroxy-3-chloro-5-methyl-benzamidine (23 mg, 117 µmol) according to Method A; LC-MS: $t_R$=0.60 min; [M+1]$^+$=392.12.

Example 193

4-[5-(5-Diethylaminomethyl-4-methyl-thiophen-2-yl)-[1,2,4]oxadiazol-3-yl]-3-methoxy-phenol The title compound (7 mg) is prepared starting from 5-diethylaminomethyl-4-methyl-thiophene-2-carboxylic acid (30 mg, 130 µmol) and 4,N-dihydroxy-2-methoxy-benzamidine (21 mg, 117 µmol) according to Method A; LC-MS: $t_R$=0.50 min; [M+1]$^+$=374.12.

Example 194

N-((2S)-3-{4-[5-(5-Diethylaminomethyl-4-methyl-thiophen-2-yl)-[1,2,4]oxadiazol-3-yl]-2-methoxy-6-methyl-phenoxy}-2-hydroxy-propyl)-2-hydroxy-acetamide The title compound (6 mg) is prepared starting from 5-diethylaminomethyl-4-methyl-thiophene-2-carboxylic acid (30 mg, 130 µmol) and (S)-2-hydroxy-N-(2-hydroxy-3-[4-(N-hydroxycarbamimidoyl)-2-methoxy-6-methyl-phenoxy]-propyl)-acetamide (38 mg, 117 µmol) according to Method A; LC-MS: $t_R$=0.51 min; [M+1]$^+$=519.17.

Example 195

N-((2S)-3-{4-[5-(5-Diethylaminomethyl-4-methyl-thiophen-2-yl)-[1,2,4]oxadiazol-3-yl]-2-chloro-6-methyl-phenoxy}-2-hydroxy-propyl)-2-hydroxy-acetamide The title compound (31 mg) is prepared starting from 5-diethylaminomethyl-4-methyl-thiophene-2-carboxylic acid (30 mg, 130 µmol) and (S)-2-hydroxy-N-(2-hydroxy-3-[4-(N-hydroxycarbamimidoyl)-2-chloro-6-methyl-phenoxy]-propyl)-acetamide (39 mg, 117 µmol) according to Method A; LC-MS: $t_R$=0.53 min; [M+1]$^+$=523.14; $^1$H NMR (D$_6$-DMSO): δ1.03 (t, J=7.0 Hz, 6H), 2.22 (s, 3H), 2.40 (s, 3H), 2.58 (q, J=7.0 Hz, 4H), 3.20-3.29 (m, 1H), 3.40-3.48 (m, 1H), 3.74 (s, 2H), 3.83 (d, J=5.8 Hz, 2H), 3.86-4.01 (m, 3H), 5.32 (d, J=5.3 Hz, 1H), 5.55 (t, J=6.0 Hz, 1H), 7.70 (t br, J=6.0 Hz, 1H), 7.82 (s, 1H), 7.86-7.89 (m, 1H), 7.89-7.90 (m, 1H).

Example 196

N-(3-{4-[5-(5-Diethylaminomethyl-4-methyl-thiophen-2-yl)-[1,2,4]oxadiazol-3-yl]-3-methyl-phenoxy}-2-hydroxy-propyl)-2-hydroxy-acetamide The title compound (3 mg) is prepared starting from 5-diethylaminomethyl-4-methyl-thiophene-2-carboxylic acid (30 mg, 130 µmol) and (S)-2-hydroxy-N-(2-hydroxy-3-[4-(N-hydroxycarbamimidoyl)-3-methyl-phenoxy]-propyl)-acetamide (35 mg, 117 µmol) according to Method A; LC-MS: $t_R$=0.50 min; [M+1]$^+$=489.23.

Example 197

(2S)-3-{4-[5-(5-Diethylaminomethyl-4-methyl-thiophen-2-yl)-[1,2,4]oxadiazol-3-yl]-2-methoxy-6-methyl-phenoxy}-propane-1,2-diol (R)-(5-{3-[4-(2,2-Dimethyl-[1,3]dioxolan-4-ylmethoxy)-3-methoxy-5-methyl-phenyl]-[1,2,4]oxadiazol-5-yl}-3-methyl-thiophen-2-ylmethyl)-diethyl-amine is prepared starting from 5-diethylaminomethyl-4-methyl-thiophene-2-carboxylic acid (30 mg, 130 µmol) and (R)-4-(2,2-dimethyl-[1,3]dioxolan-4-ylmethoxy)-N-hydroxy-3-methoxy-5-methyl-benzamidine (36 mg, 117 µmol) according to Method A. After the coupling and cyclisation step, the reaction mixture is acidified by adding 35% aq. HCl and the reaction mixture is stirred at rt for 40 min. The mixture is neutralised by adding 25% aq. NH$_3$ solution before it is separated by prep. HPLC to give the title compound (31 mg) as a resin; LC-MS: $t_R$=0.52 min; [M+1]$^+$=462.21; $^1$H NMR (D$_6$-DMSO): δ1.03 (t, J=7.0 Hz, 6H), 2.22 (s, 3H), 2.32 (s, 3H), 2.58 (q, J=7.0 Hz, 4H), 3.41-3.50 (m, 2H), 3.73 (s, 2H), 3.74-3.81 (m, 1H), 3.84-3.89 (m, 1H), 3.89 (s, 3H), 4.03 (dd, J=9.8, 4.3 Hz, 1H), 4.59 (t, J=5.8 Hz, 1H), 4.84 (d, J=5.3 Hz, 1H), 7.44-7.47 (m, 1H), 7.49-7.52 (m, 1H), 7.81 (s, 1H).

Example 198

(2S)-3-{2-Chloro-4-[5-(5-diethylaminomethyl-4-methyl-thiophen-2-yl)-[1,2,4]oxadiazol-3-yl]-6-methyl-phenoxy}-propane-1,2-diol The title compound (22 mg) is prepared starting from 5-diethylaminomethyl-4-methyl-thiophene-2-carboxylic acid (30 mg, 130 µmol) and (R)-4-(2,2-dimethyl-[1,3]dioxolan-4-ylmethoxy)-N-hydroxy-3-chloro-5-methyl-benzamidine (37 mg, 117 µmol) in analogy to Example 197; LC-MS: $t_R$=0.54 min; [M+1]$^+$=466.05.

Example 199

(2S)-3-{4-[5-(5-Diethylaminomethyl-4-methyl-thiophen-2-yl)-[1,2,4]oxadiazol-3-yl]-3-methoxy-phenoxy}-propane-1,2-diol The title compound (13 mg) is prepared starting from 5-diethylaminomethyl-4-methyl-thiophene-2-carboxylic acid (30 mg, 130 µmol) and (R)-4-(2,2-dimethyl-[1,3]dioxolan-4-ylmethoxy)-N-hydroxy-2-methoxy-benzamidine (35 mg, 117 µmol) in analogy to Example 197; LC-MS: $t_R$=0.47 min; [M+1]$^+$=448.09.

Example 200

(2S)-1-Amino-3-{4-[5-(5-diethylaminomethyl-4-methyl-thiophen-2-yl)-[1,2,4]oxadiazol-3-yl]-2-ethyl-6-methyl-phenoxy}-propan-2-ol a) To a solution of 4-[5-(5-diethylaminomethyl-4-methyl-thiophen-2-yl)-[1,2,4]oxadiazol-3-yl]-2-ethyl-6-methyl-phenol (1.49 g, 3.87 mmol) in isopropanol (70 mL) and 3 N aq. NaOH (19 mL), (R)-epichlorohydrine is added. The mixture is stirred at rt for 41 h. The mixture is diluted with EA and washed with 1 M aq. NaOH. The washing is extracted back with EA. The organic extracts are combined, dried over MgSO$_4$, filtered and concentrated. The crude product is purified by prep. HPLC (XBridge C18, 50×50 mm, 10 µm, eluting with a gradient of acetonitrile in water containing 0.5% of concentrated aq. ammonia) to give diethyl-{5-[3-((S)-3-ethyl-5-methyl-4-oxiranylmethoxy-phenyl)-[1,2,4]oxadiazol-5-yl]-3-methyl-thiophen-2-ylmethyl}-amine (990 mg) as a pale yellow resin; LC-MS: $t_R$=0.65 min; [M+1]$^+$=442.09.
b) A solution of diethyl-{5-[3-((S)-3-ethyl-5-methyl-4-oxiranylmethoxy-phenyl)-[1,2,4]oxadiazol-5-yl]-3-methyl-thiophen-2-ylmethyl}-amine (450 mg, 1.02 mmol) in 7 N NH$_3$ in methanol is stirred in a sealed vessel at 65° C. for 16 h. The solvent is evaporated and the crude product is purified by prep. HPLC. The product containing fractions are filtered over Amberlyst A21. The filtrate is concentrated and dried to give the title compound (381 mg) as a yellow resin; LC-MS: $t_R$=0.44 min; [M+1]$^+$=459.10; $^1$H NMR (D$_6$-DMSO): δ1.03 (t, J=7.0 Hz, 6H), 1.23 (t, J=7.5 Hz, 3H), 2.22 (s, 3H), 2.35 (s, 3H), 2.58 (q, J=7.0 Hz, 4H), 2.73 (q, J=7.5 Hz, 2H), 2.88 (dd, J=12.8, 9.0 Hz, 1H), 3.10 (dd, J=12.5, 3.0 Hz, 1H), 3.73 (s, 2H), 3.81 (d, J=5.3 Hz, 2H), 4.04-4.12 (m, 1H), 7.75 (s, 2H), 7.80 (s, 1H).

Example 201

2-{4-[5-(5-Diethylaminomethyl-4-methyl-thiophen-2-yl)-[1,2,4]oxadiazol-3-yl]-2-ethyl-6-methyl-phenoxy}-ethylamine To a mixture of 4-[5-(5-diethylaminomethyl-4-methyl-thiophen-2-yl)-[1,2,4]oxadiazol-3-yl]-2-ethyl-6-methyl-phenol (700 mg, 1.82 mmol) and $K_2CO_3$ (760 mg, 5.45 mmol) in acetonitrile (14 mL), 2-(Boc-amino)-ethylbromide (839 mg, 3.63 mmol) is added. The mixture is stirred at 80° C. for 12 h. The mixture is filtered and the filtrate is concentrated. The residue is dissolved in DCM (10 mL) and treated with TFA (1.4 mL). The mixture is stirred at rt for 19 h before another portion of TFA (0.7 mL) is added. Stirring is continued at rt for another 21 h. The mixture is diluted with DCM and washed with 1 M aq. NaOH. The washing is extracted back with DCM. The combined organic extracts are dried over $MgSO_4$, filtered and concentrated. The crude product is purified by prep. HPLC. The product containing fractions are combined, concentrated, dissolved in methanol:water 9:1 and filtered over Amberlyst A-21. The filtrate is evaporated and dried to give the title compound (513 mg) as a pale yellow resin; LC-MS: $t_R$=0.44 min; $[M+1]^+$=429.20; $^1$H NMR ($D_6$-DMSO): δ1.03 (t, J=7.0 Hz, 6H), 1.23 (t, J=7.5 Hz, 3H), 2.22 (s, 3H), 2.35 (s, 3H), 2.58 (q, J=7.3 Hz, 4H), 2.73 (q, J=7.5 Hz, 2H), 3.05 (t, J=5.5 Hz, 2H), 3.73 (s, 3H), 3.86 (t, J=5.5 Hz, 2H), 7.75 (s, 2H), 7.80 (s, 1H).

Example 202

3-{4-[5-(5-Diethylaminomethyl-4-methyl-thiophen-2-yl)-[1,2,4]oxadiazol-3-yl]-2-ethyl-6-methyl-phenoxy}-propylamine The title compound (309 mg) is prepared in analogy to Example 201 starting from 4-[5-(5-diethylaminomethyl-4-methyl-thiophen-2-yl)-[1,2,4]oxadiazol-3-yl]-2-ethyl-6-methyl-phenol (700 mg, 1.82 mmol) and 3-(Boc-amino)-propylbromide (900 mg, 3.63 mmol); LC-MS: $t_R$=0.46 min; $[M+1]^+$=443.10.

Example 203

1-((2S)-3-{4-[5-(5-Diethylaminomethyl-4-methyl-thiophen-2-yl)-[1,2,4]oxadiazol-3-yl]-2-ethyl-6-methyl-phenoxy}-2-hydroxy-propyl)-azetidine-3-carboxylic acid To a solution of azetidine-2-carboxylic acid methyl ester hydrochloride (51 mg, 340 μmol) in methanol (1 mL), a solution of diethyl-{5-[3-((S)-3-ethyl-5-methyl-4-oxiranylmethoxy-phenyl)-[1,2,4]oxadiazol-5-yl]-3-methyl-thiophen-2-ylmethyl}-amine (30 mg, 68 μmol) in methanol (1 mL) followed by DIPEA (90 mg, 679 μmol) is added. The mixture is stirred at 70° C. for 22 h before it is cooled to rt and 3 M aq. NaOH (0.35 mL) is added. The mixture is stirred at rt for 18 h before it is separated by prep. HPLC (Waters XBridge Prep C18, 75×30 mm ID, 10 μm, eluting with a gradient of acetonitrile in water containing 0.5% of sat. aq. ammonia) to give the title compound (29 mg) as a resin; LC-MS*: $t_R$=0.74 min; $[M+1]^+$=543.09; $^1$H NMR ($D_6$-DMSO): δ1.03 (t, J=7.0 Hz, 6H), 1.21 (t, J=7.5 Hz, 3H), 2.22 (s, 3H), 2.33 (s, 3H), 2.58 (q, J=7.0 Hz, 4H), 2.62-2.69 (m, 1H), 2.73 (q, J=7.3 Hz, 2H), 3.10-3.17 (m, 1H), 3.18-3.22 (m, 1H), 3.22-3.28 (m, 2H), 3.42-3.51 (m, 2H), 3.66-3.72 (m, 1H), 3.73 (s, 2H), 3.74-3.80 (m, 2H), 7.72 (s, 2H), 7.80 (s, 1H).

Example 204

(2S)-1-((2S)-3-{4-[5-(5-Diethylaminomethyl-4-methyl-thiophen-2-yl)-[1,2,4]oxadiazol-3-yl]-2-ethyl-6-methyl-phenoxy}-2-hydroxy-propyl)-pyrrolidine-2-carboxylic acid The title compound (25 mg) is obtained from diethyl-{5-[3-((S)-3-ethyl-5-methyl-4-oxiranylmethoxy-phenyl)-[1,2,4]oxadiazol-5-yl]-3-methyl-thiophen-2-ylmethyl}-amine (30 mg, 68 μmol) and L-proline methyl ester hydrochloride (56 mg, 340 μmol) in analogy to Example 203; LC-MS*: $t_R$=0.82 min; $[M+1]^+$=557.16; $^1$H NMR ($D_6$-DMSO): δ 1.03 (t, J=7.0 Hz, 6H), 1.22 (t, J=7.5 Hz, 3H), 1.66-1.77 (m, 1H), 1.83-2.01 (m, 2H), 2.09-2.17 (m, 1H), 2.22 (s, 3H), 2.35 (s, 3H), 2.58 (q, J=7.0 Hz, 4H), 2.73 (q, J=7.5 Hz, 2H), 2.83-2.91 (m, 1H), 3.04 (dd, J=12.8, 9.3 Hz, 1H), 3.15 (dd, J=12.5, 3.3 Hz, 1H), 3.43-3.50 (m, 1H), 3.55 (dd, J=9.0, 4.3 Hz, 1H), 3.73 (s, 2H), 3.78 (d, J=5.0 Hz, 2H), 4.06-4.13 (m, 1H), 7.74 (s, 2H), 7.80 (s, 1H).

Example 205

1-((2S)-3-{4-[5-(5-Diethylaminomethyl-4-methyl-thiophen-2-yl)-[1,2,4]oxadiazol-3-yl]-2-ethyl-6-methyl-phenoxy}-2-hydroxy-propyl)-pyrrolidine-3-carboxylic acid The title compound is prepared starting from diethyl-{5-[3-((S)-3-ethyl-5-methyl-4-oxiranylmethoxy-phenyl)-[1,2,4]oxadiazol-5-yl]-3-methyl-thiophen-2-ylmethyl}-amine (30 mg, 68 μmol) and rac-pyrrolidine-3-carboxylic acid methyl ester hydrochloride (56 mg, 340 μmol) in analogy to Example 203; LC-MS*: $t_R$=0.76 min; $[M+1]^+$=557.17; $^1$H NMR ($D_6$-DMSO): δ 1.03 (t, J=7.0 Hz, 6H), 1.21 (t, J=7.5 Hz, 3H), 1.90-1.98 (m, 2H), 2.22 (s, 3H), 2.34 (s, 3H), 2.43-2.49 (m, 1H), 2.58 (q, J=7.0 Hz, 4H), 2.67-2.77 (m, 5H), 2.80-2.95 (m, 2H), 3.73 (s, 2H), 3.74-3.77 (m, 1H), 3.78-3.84 (m, 2H), 3.91-3.98 (m, 1H), 7.72 (s, 2H), 7.80 (s, 1H).

Examples 206 to 219

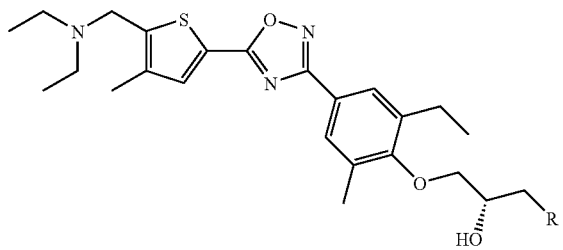

The following Examples (7-18 mg) are prepared in analogy to Example 200 step b) starting from diethyl-{5-[3-((S)-3-ethyl-5-methyl-4-oxiranylmethoxy-phenyl)-[1,2,4]oxadiazol-5-yl]-3-methyl-thiophen-2-ylmethyl}-amine (20 mg, 45 μmol) and the appropriate amine (225 μmol).

| Example | R | LC-MS $t_R$ [min] | [M + H]$^+$ |
|---|---|---|---|
| 206 | HN-CH₃ | 0.50 | 473.20 |
| 207 | HN-Et | 0.51 | 487.33 |
| 208 | N(CH₃)₂ | 0.51 | 487.27 |
| 209 | N(Me)(Et) | 0.52 | 501.10 |
| 210 | HN-CH₂CH₂OH | 0.49 | 503.21 |
| 211 | N(Me)-CH₂CH₂OH | 0.50 | 517.13 |
| 212 | HN-(CH₂)₃-OH | 0.50 | 517.22 |
| 213 | HN-CH(CH₂OH)₂ | 0.49 | 533.30 |
| 214 | HN-CH(CH₂OH)₂ | 0.49 | 533.22 |
| 215 | HN-CH₂CH₂-OCH₃ | 0.52 | 517.20 |
| 216 | HN-CH₂CH₂-NH₂ | 0.45 | 502.41 |
| 217 | HN-CH₂-C(O)OMe | 0.52 | 531.74 |
| 218 | N(Me)-CH₂-C(O)OMe | 0.53 | 545.20 |
| 219 | HN-CH₂CH₂-C(O)OMe | 0.52 | 545.18 |

Example 211

$^1$H NMR (D$_6$-DMSO): δ1.04 (t, J=6.8 Hz, 6H), 1.22 (t, J=7.5 Hz, 3H), 2.22 (s, 3H), 2.27 (s, 3H), 2.35 (s, 3H), 2.41-2.48 (m, 2H), 2.58 (q, J=7.3 Hz, 4H), 2.74 (q, J=7.5 Hz, 2H), 3.48 (q, J=5.5 Hz, 2H), 3.73 (s, 2H), 3.74-3.78 (m, 1H), 3.80-3.85 (m, 1H), 3.91-3.98 (m, 1H), 4.37 (t br, J=4.5 Hz), 4.84 (d br, J=3.3 Hz, 1H), 7.73 (s, 2H), 7.80 (s, 1H).

Example 214

$^1$H NMR (D$_6$-DMSO): δ1.04 (t, J=7.0 Hz, 6H), 1.22 (t, J=7.8 Hz, 3H), 2.22 (s, 3H), 2.35 (s, 3H), 2.58 (q, J=6.8 Hz, 4H), 2.64-2.71 (m, 1H), 2.73 (q, J=7.0 Hz, 2H), 2.79-2.87 (m, 1H), 3.33-3.47 (m, 5H), 3.71-3.77 (m, 3H), 3.78-3.85 (m, 1H), 3.86-3.94 (m, 1H), 4.37-4.45 (m, 2H), 5.02 (d, J=4.8 Hz, 1H), 7.73 (s, 2H), 7.80 (s, 1H).

Examples 220 to 222

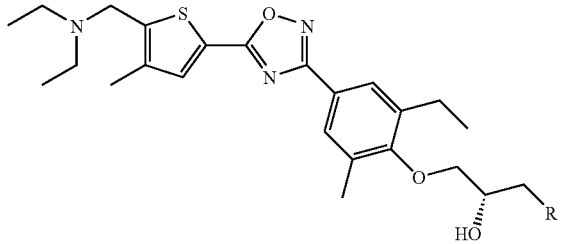

The following Examples are prepared in analogy to Example 96 starting from Example 217, 218, and 219, respectively.

| Example | R | LC-MS $t_R$ [min] | [M + H]$^+$ |
|---|---|---|---|
| 220 | HN-CH₂-C(O)OH | 0.50 | 517.26 |
| 221 | N(Me)-CH₂-C(O)OH | 0.51 | 531.16 |
| 222 | HN-CH₂CH₂-C(O)OH | 0.50 | 531.04 |

Examples 223 and 224

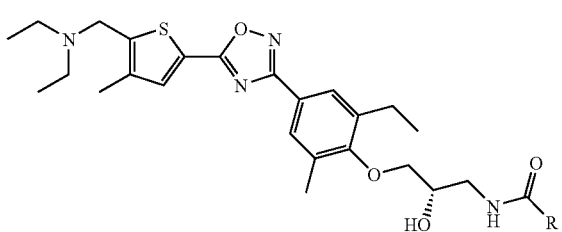

The following Examples (6-13 mg) are prepared in analogy to Example 163 starting from (2S)-1-amino-3-{4-[5-(5-diethylaminomethyl-4-methyl-thiophen-2-yl)-[1,2,4]oxadiazol-3-yl]-2-ethyl-6-methyl-phenoxy}-propan-2-ol (30 mg, 65 µmol) and the appropriate carboxylic acid (72 µmol).

| Example | R | LC-MS* $t_R$ [min] | [M + H]$^+$ |
|---|---|---|---|
| 223 | -CH₂CH₂-OH | 1.03 | 531.17 |
| 224 | -CH₂-N(Me)₂ | 1.13 | 544.18 |

Example 224

$^1$H NMR (D$_6$-DMSO): δ1.04 (t, J=7.0 Hz, 6H), 1.21 (t, J=7.5 Hz, 3H), 2.22 (s, 9H), 2.33 (s, 3H), 2.58 (q, J=7.0 Hz, 4H), 2.72 (q, J=7.8 Hz, 2H), 2.88 (s, 2H), 3.20-3.28 (m, 1H), 3.34-3.44 (m, 1H), 3.68-3.79 (m, 4H), 3.92-3.99 (m, 1H), 5.29 (d, J=5.3 Hz, 1H), 7.73 (s, 2H), 7.77 (t br, J=6.0 Hz, 1H), 7.81 (s, 1H).

Examples 225 to 228

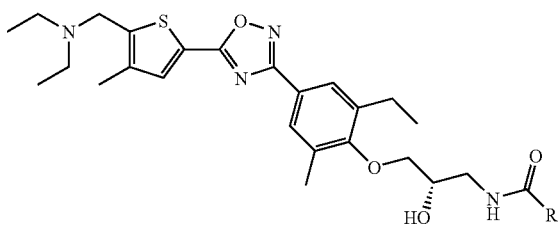

The following Examples (1-2 mg) are prepared in analogy to Example 165 starting from (2S)-1-amino-3-{4-[5-(5-diethylaminomethyl-4-methyl-thiophen-2-yl)-[1,2,4]oxadiazol-3-yl]-2-ethyl-6-methyl-phenoxy}-propan-2-ol (30 mg, 65 μmol) and the appropriate Boc-protected amino acid (72 μmol).

| | | LC-MS | |
|---|---|---|---|
| Example | R | $t_R$ [min] | [M + H]$^+$ |
| 225 | ⤳NH$_2$ | 0.50 | 516.00 |
| 226 | ⤳N(H)- | 0.50 | 530.24 |
| 227 | ⤳NH$_2$ | 0.50 | 530.20 |
| 228 | ⤳N(H)- | 0.50 | 544.34 |

Example 229

4-[5-(5-Diethylaminomethyl-4-methyl-thiophen-2-yl)-[1,2,4]oxadiazol-3-yl]-N-(2-dimethylamino-ethyl)-benzamide The title compound (9 mg) is prepared in analogy to Example 189 step b) starting from 4-[5-(5-diethylaminomethyl-4-methyl-thiophen-2-yl)-[1,2,4]oxadiazol-3-yl]-benzoic acid (37 mg, 100 μmol) and N1,N1-dimethyl-ethane-1,2-diamine (10 mg, 110 μmol); LC-MS: $t_R$=0.42 min; [M+1]$^+$=442.23. $^1$H NMR (CDCl$_3$): δ1.11 (t, J=7.0 Hz, 6H), 2.26 (s, 3H), 2.32 (s, 6H), 2.58 (t, J=6.0 Hz, 2H), 2.64 (q, J=7.0 Hz, 4H), 3.55-3.62 (m, 2H), 3.73 (s, 2H), 6.95 (t br, J=4.8 Hz, 1H), 7.68 (s, 1H), 7.92-7.96 (m, 2H), 8.21-8.25 (m, 2H).

Example 230

{4-[5-(5-Diethylaminomethyl-4-methyl-thiophen-2-yl)-[1,2,4]oxadiazol-3-yl]-benzoylamino}-acetic acid ethyl ester The title compound (116 mg) is obtained as a white solid in analogy to Example 189 step b) starting from 4-[5-(5-diethylaminomethyl-4-methyl-thiophen-2-yl)-[1,2,4]oxadiazol-3-yl]-benzoic acid (150 mg, 403 μmol) and glycine ethyl ester (46 mg, 443 μmol); LC-MS: $t_R$=0.55 min; [M+1]$^+$=457.22; $^1$H NMR (D$_6$-DMSO): δ1.04 (t, J=7.0 Hz, 6H), 1.23 (t, J=7.3 Hz, 3H), 2.23 (s, 3H), 2.58 (q, J=7.0 Hz, 4H), 3.74 (s, 2H), 4.04 (d, J=5.5 Hz, 2H), 4.15 (q, J=7.0 Hz, 2H), 7.83 (s, 1H), 8.07 (d, J=8.0 Hz, 2H), 8.17 (d, J=7.8 Hz, 2H), 9.15 (t, J=5.3 Hz, 1H).

Example 231

{4-[5-(5-Diethylaminomethyl-4-methyl-thiophen-2-yl)-[1,2,4]oxadiazol-3-yl]-benzoylamino}-acetic acid A solution of {4-[5-(5-diethylaminomethyl-4-methyl-thiophen-2-yl)-[1,2,4]oxadiazol-3-yl]-benzoylamino}-acetic acid ethyl ester (105 mg, 230 μmol) in 2 M LiOH in methanol (10 mL) is stirred at rt for 20 h. The mixture is acidified by adding aq. HCl before it is extracted twice with EA. The aq. solution is neutralised by adding sat. aq. NaHCO$_3$ solution and concentrated. The remaining solid is suspended in methanol, filtered and the filtrate is concentrated. The remaining residue is again suspended in a small volume of methanol, filtered and the filtrate is again concentrated. The crude product is purified by CC on silica gel eluting with DCM containing 20% of methanol to give the title compound (30 mg) as a white solid; LC-MS: $t_R$=0.48 min; [M+1]$^+$=429.09; $^1$H NMR (D$_6$-DMSO): δ1.04 (t, J=7.0 Hz, 6H), 2.23 (s, 3H), 2.58 (q, J=7.3 Hz, 4H), 3.60 (d, J=4.8 Hz, 2H), 3.74 (s, 2H), 7.84 (s, 1H), 8.02-8.07 (m, 2H), 8.10-8.15 (m, 2H), 8.17 (t, J=4.5 Hz, 1H).

Example 232

GTPγS Assay to Determine EC$_{50}$ Values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 μM GDP (Sigma, G-7127), 2.5% DMSO (Fluka, 41644), 50 pM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 μl MicroScint20 (Packard Biosciences, order #6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Nonspecific binding is the amount of binding in the absence of an agonist in the assay.

$EC_{50}$ values of all exemplified compounds (with the exception of the compounds of Examples 91, 95, 155, 159-161, 163-168, 200-202, 217-219, and 231 which have not been measured) are in the range of 0.2 to 5720 nM with an average of 221 nM. Agonistic activities, determined according to the method described above, of some compounds of the present invention are displayed in Table 1.

TABLE 1

| Compound of Example | $EC_{50}$ [nM] |
|---|---|
| 4 | 11.9 |
| 21 | 3.8 |
| 24 | 11.0 |
| 28 | 0.2 |
| 30 | 10.2 |
| 31 | 8.1 |
| 32 | 11.2 |
| 33 | 9.8 |
| 44 | 12.1 |
| 51 | 1.0 |
| 52 | 2.2 |
| 54 | 2.0 |
| 56 | 2.5 |
| 57 | 2.8 |
| 58 | 3.3 |
| 59 | 7.0 |
| 81 | 2.6 |
| 84 | 0.8 |
| 86 | 9.1 |
| 87 | 0.6 |
| 92 | 0.5 |
| 98 | 17.3 |
| 106 | 8.6 |
| 115 | 10.5 |
| 119 | 2.1 |
| 136 | 18.5 |
| 149 | 1.6 |
| 150 | 5.4 |
| 187 | 22 |
| 194 | 2.5 |
| 195 | 0.2 |
| 196 | 13.0 |
| 198 | 2.1 |
| 205 | 18.4 |
| 210 | 9.6 |
| 214 | 1.7 |
| 220 | 3.4 |
| 223 | 6.2 |
| 225 | 1.1 |
| 226 | 3.5 |

Example 233

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zürich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when $p<0.05$.

As an example, Table 2 shows the effect on lymphocyte counts 3 h after oral administration of 10 mg/kg of some compounds of the present invention to normotensive male Wistar rats as compared to a group of animals treated with vehicle only.

TABLE 2

| Compound of Example | Lymphocyte counts |
|---|---|
| 14 | −58 ± 3% |
| 27 | −52 ± 5% |
| 28 | −68 ± 3% |
| 53 | −69 ± 2% |
| 55 | −60 ± 2% |
| 56 | −68 ± 1% |
| 67 | −56 ± 4% |
| 88 | −68 ± 2% |
| 89 | −67 ± 3% |
| 90 | −65 ± 5% |

What is claimed is:

1. A compound of the Formula (I)

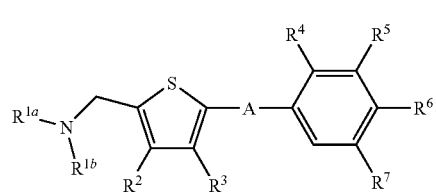

wherein
A represents

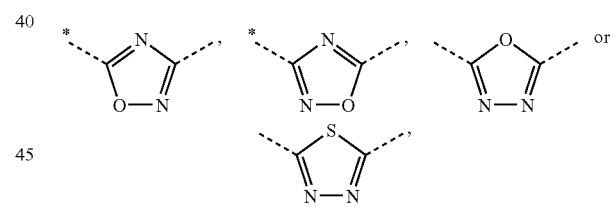

wherein the asterisks indicate the bond that is linked to the thiophene group of Formula (I);

$R^{1a}$ represents $C_{1-5}$-alkyl, $C_{3-5}$-cycloalkyl, or 2-hydroxyethyl;

$R^{1b}$ represents hydrogen or $C_{1-3}$-alkyl;

or $R^{1a}$ and $R^{1b}$, together with the nitrogen to which they are attached, form an azetidine, a pyrrolidine, a piperidine, or a morpholine ring;

$R^2$ represents hydrogen or $C_{1-2}$-alkyl;

$R^3$ represents hydrogen or $C_{1-2}$-alkyl;

$R^4$ represents hydrogen, $C_{1-2}$-alkyl, methoxy, or halogen;

$R^5$ represents hydrogen, $C_{1-4}$-alkyl, or $C_{1-4}$-alkoxy;

$R^6$ represents hydroxy-$C_{1-4}$-alkyl, di-(hydroxy-$C_{1-4}$-alkyl)-$C_{1-4}$-alkyl, 2,3-dihydroxypropyl, —CH$_2$—(CH$_2$)$_n$—NR$^{61}$R$^{62}$, —CH$_2$—(CH$_2$)$_n$—NHCOR$^{64}$, —CH$_2$—(CH$_2$)$_n$—NHSO$_2$R$^{63}$, —CH$_2$—CH$_2$—COOH, —CH$_2$—CH$_2$—CONR$^{61}$R$^{62}$, 1-(3-carboxy-azetidinyl)-3-propionyl, 1-(2-carboxy-pyrrolidinyl)-3-propionyl, 1-(3-carboxy-pyrrolidiny)-3-propionyl, —CH$_2$—CH(OH)—CH—CH$_2$—NR$^{61}$R$^{62}$, —CH$_2$—CH(OH)—CH$_2$—NHCOR$^{64}$, —CH$_2$—CH(OH)—CH$_2$—NHSO$_2$R$^{63}$, —CO—NHR$^{61}$, hydroxy, hydroxy-C$_{2\text{-}4}$-alkoxy, di-(hydroxy-C$_{1\text{-}4}$-alkyl)-C$_{1\text{-}4}$-alkoxy, 2,3-dihydroxypropoxy, 2-hydroxy-3-methoxy-propoxy, —OCH$_2$—(CH$_2$)$_m$—NR$^{61}$R$^{62}$, —OCH$_2$—(CH$_2$)$_m$—NHCOR$^{64}$, —OCH$_2$—(CH$_2$)$_m$—NHSO$_2$R$^{63}$, 2-[(azetidine-3-carboxylic acid)-1-yl]-ethoxy, 2-[(pyrrolidine-2-carboxylic acid)-1-yl]-ethoxy, 2-[(pyrrolidine-3-carboxylic acid)-1-yl]-ethoxy, —OCH$_2$—CH(OH)—CH$_2$—NR$^{61}$R$^{62}$, —OCH$_2$—CH(OH)—CH$_2$—NHCOR$^{64}$, —OCH$_2$—CH(OH)—CH$_2$—NHSO$_2$R$^{63}$, 3-[(azetidine-3-carboxylic acid)-1-yl]-2-hydroxypropoxy, 2-hydroxy-3-[(pyrrolidine-2-carboxylic acid)-1-yl]-propoxy, 2-hydroxy-3-[(pyrrolidine-3-carboxylic acid)-1-yl]-propoxy, —NR$^{61}$R$^{62}$, —NHCO—R$^{64}$, or —SO$_2$NH—R$^{61}$;

R$^{61}$ represents hydrogen, methyl, ethyl, 2-hydroxyethyl, 2-hydroxy-1-hydroxymethyl-ethyl, 2,3-dihydroxy-propyl, 2-C$_{1\text{-}2}$-alkoxyethyl, 3-hydroxypropyl, 2-aminoethyl, 2-(C$_{1\text{-}4}$-alkylamino)ethyl, 2-(di-(C$_{1\text{-}4}$-alkyl)amino)ethyl, carboxymethyl, (C$_{1\text{-}4}$-alkylcarboxy)methyl, 2-carboxyethyl, or 2-(C$_{1\text{-}4}$-alkylcarboxy)ethyl;

R$^{62}$ represents hydrogen or methyl;

R$^{63}$ represents methyl, ethyl, methylamino, ethylamino, or dimethylamino;

R$^{64}$ represents hydroxymethyl, 2-hydroxyethyl, aminomethyl, methylaminomethyl, dimethylaminomethyl, 2-aminoethyl, or 2-methylamino-ethyl;

m represents the integer 1 or 2;

n represents 0, 1, or 2; and

R$^7$ represents hydrogen, C$_{1\text{-}2}$-alkyl, or halogen;

or a salt of such a compound.

2. A compound according to claim 1, wherein A represents

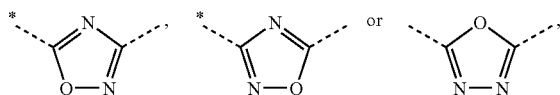

or a salt of such a compound.

3. A compound according to claim 1, wherein R$^{1a}$ represents C$_{4\text{-}5}$-alkyl, or a salt of such a compound.

4. A compound according to claim 1, wherein R$^{1a}$ represents C$_{1\text{-}4}$-alkyl, C$_{3\text{-}4}$-cycloalkyl, or 2-hydroxyethyl, and R$^{1b}$ represents C$_{1\text{-}3}$-alkyl; or R$^{1a}$ and R$^{1b}$, together with the nitrogen to which they are attached, form an azetidine or a pyrrolidine ring; or a salt of such a compound.

5. A compound according to claim 1, wherein R$^{1a}$ represents C$_{1\text{-}4}$-alkyl and R$^{1b}$ represents C$_{1\text{-}2}$-alkyl, or a salt of such a compound.

6. A compound according to claim 1, wherein R$^2$ represents C$_{1\text{-}2}$-alkyl, or a salt of such a compound.

7. A compound according to claim 1, wherein R$^3$ represents hydrogen, or a salt of such a compound.

8. A compound according to claim 1, wherein R$^4$ represents hydrogen, R$^5$ represents C$_{1\text{-}3}$-alkyl or methoxy, and R$^7$ represents C$_{1\text{-}2}$-alkyl or chloro, or a salt of such a compound.

9. A compound according to claim 1, wherein R$^6$ represents di-(hydroxy-C$_{1\text{-}4}$-alkyl)-C$_{1\text{-}4}$-alkyl, 2,3-dihydroxypropyl, —CH$_2$—(CH$_2$)$_n$—NHCOR$^{64}$, —CH$_2$—(CH$_2$)$_n$—NHSO$_2$R$^{63}$, —CH$_2$—CH$_2$—COOH, —CH$_2$—CH$_2$—CONR$^{61}$R$^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, —CH$_2$—CH(OH)—CH$_2$—NR$^{61}$R$^{62}$, —CH$_2$—CH(OH)—CH$_2$—NHCOR$^{64}$, —CH$_2$—CH(OH)—CH$_2$—NHSO$_2$R$^{63}$, —CO—NHR$^{61}$, hydroxy-C$_{2\text{-}4}$-alkoxy, di-(hydroxy-C$_{1\text{-}4}$-alkyl)-C$_{1\text{-}4}$-alkoxy, 2,3-dihydroxypropoxy, 2-hydroxy-3-methoxy-propoxy, —OCH$_2$—(CH$_2$)$_m$—NR$^{61}$R$^{62}$, —OCH$_2$—(CH$_2$)$_m$—NHCOR$^{64}$, —OCH$_2$—(CH$_2$)$_m$—NHSO$_2$R$^{63}$, 2-[(azetidine-3-carboxylic acid)-1-yl]-ethoxy, 2-[(pyrrolidine-2-carboxylic acid)-1-yl]-ethoxy, 2-[(pyrrolidine-3-carboxylic acid)-1-yl]-ethoxy, —OCH$_2$—CH(OH)—CH$_2$—NR$^{61}$R$^{62}$, —OCH$_2$—CH(OH)—CH$_2$—NHCOR$^{64}$, —OCH$_2$—CH(OH)—CH$_2$—NHSO$_2$R$^{63}$, 3-[(azetidine-3-carboxylic acid)-1-yl]-2-hydroxypropoxy, 2-hydroxy-3-[(pyrrolidine-2-carboxylic acid)-1-yl]-propoxy, 2-hydroxy-3-[(pyrrolidine-3-carboxylic acid)-1-yl]-propoxy, or —NR$^{61}$R$^{62}$, or a salt of such a compound.

10. A compound according to claim 1, wherein R$^6$ represents di-(hydroxy-C$_{1\text{-}4}$-alkyl)-C$_{1\text{-}4}$-alkoxy, 2,3-dihydroxypropoxy, —OCH$_2$—(CH$_2$)$_m$—NR$^{61}$R$^{62}$, —OCH$_2$—(CH$_2$)$_m$—NHCOR$^{64}$, —OCH$_2$—CH(OH)—CH$_2$—NR$^{61}$R$^{62}$, or —OCH$_2$—CH(OH)—CH$_2$—NHCOR$^{64}$, or a salt of such a compound.

11. A compound according to claim 1, wherein R$^{64}$ represents hydroxymethyl or 2-hydroxyethyl, or a salt of such a compound.

12. A compound according to claim 1 selected from the group consisting of:

N-(3-{4-[5-(5-dimethylaminomethyl-thiophen-2-yl)-[1,2,4]oxadiazol-3-yl]-2,6-dimethyl-phenoxy}-2-hydroxy-propyl)-2-hydroxy-acetamide;

3-[2,6-dimethyl-4-(5-[4-methyl-5-[(methyl-propyl-amino)-methyl]-thiophen-2-yl]-[1,2,4]oxadiazol-3-yl)-phenoxy]-propane-1,2-diol;

N-(3-{2,6-dimethyl-4-[5-(4-methyl-5-methylaminomethyl-thiophen-2-yl)-[1,2,4]oxadiazol-3-yl]-phenoxy}-2-hydroxy-propyl)-2-hydroxy-acetamide;

2-hydroxy-N-[2-hydroxy-3-(4-{5-[5-(isopropylamino-methyl)-4-methyl-thiophen-2-yl]-[1,2,4]oxadiazol-3-yl}-2,6-dimethyl-phenoxy)-propyl]-acetamide;

N-(3-{4-[5-(5-dimethylaminomethyl-4-methyl-thiophen-2-yl)-[1,2,4]oxadiazol-3-yl]-2,6-dimethyl-phenoxy}-2-hydroxy-propyl)-2-hydroxy-acetamide;

N-{3-[2,6-dimethyl-4-(5-{4-methyl-5-[(methyl-propyl-amino)-methyl]-thiophen-2-yl}-[1,2,4]oxadiazol-3-yl)-phenoxy]-2-hydroxy-propyl}-2-hydroxy-acetamide;

2-hydroxy-N-(2-hydroxy-3-{4-[5-(5-{[(2-hydroxy-ethyl)-methyl-amino]-methyl}-4-methyl-thiophen-2-yl)-[1,2,4]oxadiazol-3-yl]-2,6-dimethyl-phenoxy}-propyl)-acetamide;

N-(3-{4-[5-(5-{[ethyl-(2-hydroxy-ethyl)-amino]-methyl}-4-methyl-thiophen-2-yl)-[1,2,4]oxadiazol-3-yl]-2,6-dimethyl-phenoxy}-2-hydroxy-propyl)-2-hydroxy-acetamide;

N-(3-{2,6-dimethyl-4-[5-(4-methyl-5-pyrrolidin-1-ylmethyl-thiophen-2-yl)-[1,2,4]oxadiazol-3-yl]-phenoxy}-2-hydroxy-propyl)-2-hydroxy-acetamide;

N-(3-{2,6-dimethyl-4-[5-(4-methyl-5-piperidin-1-ylmethyl-thiophen-2-yl)-[1,2,4]oxadiazol-3-yl]-phenoxy 1-2-hydroxy-propyl)-2-hydroxy-acetamide;

3-{4-[5-(5-diethylaminomethyl-4-methyl-thiophen-2-yl)-[1,2,4]oxadiazol-3-yl]-2,6-dimethyl-phenyl}-propionic acid;

N—((S)-3-{4-[5-(5-dimethylaminomethyl-4-methyl-thiophen-2-yl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{5-[(ethyl-methyl-amino)-methyl]-4-methyl-thiophen-2-yl}-[1,2,4]oxadiazol-3-yl)-6-methyl-phenoxy]-2-hydroxy-propyl}-2-hydroxy-acetamide;

N—{(S)-3-[2-ethyl-6-methyl-4-{5-[4-methyl-5-[methyl-propyl-amino)-methyl]-thiophen-2-yl}-[1,2,4]oxadiazol-3-yl)-phenoxy]-2-hydroxy-propyl}-2-hydroxy-acetamide;

N—{(S)-3-[4-(5-{5-[(butyl-methyl-amino)-methyl]-4-methyl-thiophen-2-yl}-[1,2,4]oxadiazol-3-yl)-2-ethyl-6-methyl-phenoxy]-2-hydroxy-propyl}-2-hydroxy-acetamide;

N—{(S)-3-[2-ethyl-4-(5-{5-[(isobutyl-methyl-amino)-methyl]-4-methyl-thiophen-2-yl}-[1,2,4]oxadiazol-3-yl)-6-methyl-phenoxy]-2-hydroxy-propyl}-2-hydroxy-acetamide;

N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{5-[(ethyl-propyl-amino)-methyl]-4-methyl-thiophen-2-yl}-[1,2,4]oxadiazol-3-yl)-6-methyl-phenoxy]-2-hydroxy-propyl}-2-hydroxy-acetamide;

N—{(S)-3-[2-ethyl-4-(5-{5-[(ethyl-isopropyl-amino)-methyl]-4-methyl-thiophen-2-yl}-[1,2,4]oxadiazol-3-yl)-6-methyl-phenoxy]-2-hydroxy-propyl}-2-hydroxy-acetamide;

N—{(S)-3-[4-{5-[(5-[(butyl-ethyl-amino)-methyl]-4-methyl-thiophen-2-yl}-(1,2,4]oxadiazol-3-yl)-2-ethyl-6-methyl-phenoxy]-2-hydroxy-propyl}-2-hydroxy-acetamide;

3-[4-(5-{5-[(butyl-methyl-amino)-methyl]-4-methyl-thiophen-2-yl}-[1,2,4]oxadiazol-3-yl)-2-ethyl-6-methyl-phenyl]-propionic acid; and 3-{4-[5-(5-diethylaminomethyl-4-methyl-thiophen-2-yl)-[1,2,4]oxadiazol-3-yl]-2-ethyl-6-methyl-phenyl}-propionic acid;

or a salt of such a compound.

13. A compound according to claim 1 selected from the group consisting of:

(R)-3-{4-[5-(5-dimethylaminomethyl-4-ethyl-thiophen-2-yl)-[1,2,4]oxadiazol-3-yl]-2-ethyl-6-methyl-phenoxy}-propane-1,2-diol;

(R)-3-[2-ethyl-4-(5-{4-ethyl-5-[(methyl-propyl-amino)-methyl]-thiophen-2-yl}-[1,2,4]oxadiazol-3-yl)-6-methyl-phenoxy]-propane-1,2-diol;

N—((S)-3-{4-[5-(5-dimethylaminomethyl-4-ethyl-thiophen-2-yl)-[1,2,4]oxadiazol-3-yl]-2-ethyl-6-methyl-phenoxy}-2-hydroxy-propyl)-2-hydroxy-acetamide;

N—{(S)-3-[2-ethyl-4-(5-{4-ethyl-5-[methyl-propyl-amino)-methyl]-thiophen-2-yl}-[1,2,4]oxadiazol-3-yl)-6-methyl-phenoxy]-2-hydroxy-propyl}-2-hydroxy-acetamide;

3-{4-[5-(5-dimethylaminomethyl-4-ethyl-thiophen-2-yl)-[1,2,4]oxadiazol-3-yl]-2-ethyl-6-methyl-phenyl}-propionic acid;

3-[2-ethyl-4-(5-{4-ethyl-5-[(methyl-propyl-amino)-methyl]-thiophen-2-yl}-[1,2,4]oxadiazol-3-yl)-6-methyl-phenyl]-propionic acid;

N—((S)-3-{4-[5-(5-dimethylaminomethyl-4-methyl-thiophen-2-yl)-[1,2,4]oxadiazol-3-yl]-2,6-dimethyl-phenoxy}-2-hydroxy-propyl)-2-hydroxy-acetamide;

N—{(S)-3-[4-(5-{5-[(butyl-methyl-amino)-methyl]-4-methyl-thiophen-2-yl}-[1,2,4]oxadiazol-3-yl)-2,6-dimethyl-phenoxy]-2-hydroxy-propyl}-2-hydroxy-acetamide;

2-hydroxy-N—{(S)-2-hydroxy-3-[4-(5-{5-[(isobutyl-methyl-amino)-methyl]-4-methyl-thiophen-2-yl}-[1,2,4]oxadiazol-3-yl)-2,6-dimethyl-phenoxy]-propyl}-acetamide;

N—{(S)-3-[4-(5-{5-[(ethyl-propyl-amino)-methyl]-4-methyl-thiophen-2-yl}-[1,2,4]oxadiazol-3-yl)-2,6-dimethyl-phenoxy]-2-hydroxy-propyl}-2-hydroxy-acetamide;

N—{(S)-3-[4-(5-{5-[(ethyl-isopropyl-amino)-methyl]-4-methyl-thiophen-2-yl}-[1,2,4]oxadiazol-3-yl)-2,6-dimethyl-phenoxy]-2-hydroxy-propyl}-2-hydroxy-acetamide;

N—{(S)-3-[2-ethyl-4-(5-{5-[(ethyl-isobutyl-amino)-methyl]-4-methyl-thiophen-2-yl}-[1,2,4]oxadiazol-3-yl)-6-methyl-phenoxy]-2-hydroxy-propyl}-2-hydroxy-acetamide;

(3-{4-[5-(5-diethylaminomethyl-4-methyl-thiophen-2-yl)-[1,2,4]oxadiazol-3-yl]-2-ethyl-6-methyl-phenyl}-propionylamino)-acetic acid;

{3-[2-ethyl-4-(5-{5-[(ethyl-propyl-amino)-methyl]-4-methyl-thiophen-2-yl}-[1,2,4]oxadiazol-3-yl)-6-methyl-phenyl]-propionylamino}-acetic acid;

3-{3-[2-ethyl-6-methyl-4-(5-{4-methyl-5-[(methyl-propyl-amino)-methyl]-thiophen-2-yl}-[1,2,4]oxadiazol-3-yl)-phenyl]-propionylamino}-propionic acid;

3-(3-{4-[5-(5-diethylaminomethyl-4-methyl-thiophen-2-yl)-[1,2,4]oxadiazol-3-yl]-2-ethyl-6-methyl-phenyl}-propionylamino)-propionic acid;

3-{3-[2-ethyl-4-(5-{5-[(ethyl-propyl-amino)-methyl]-4-methyl-thiophen-2-yl}-[1,2,4]oxadiazol-3-yl)-6-methyl-phenyl]-propionylamino}-propionic acid;

N—((S)-3-{4-[3-(5-dimethylaminomethyl-4-methyl-thiophen-2-yl)-[1,2,4]oxadiazol-5-yl]-2-ethyl-6-methyl-phenoxy}-2-hydroxy-propyl)-2-hydroxy-acetamide;

N—((S)-3-{4-[3-(5-diethylaminomethyl-4-methyl-thiophen-2-yl)-[1,2,4]oxadiazol-5-yl]-2-ethyl-6-methyl-phenoxy}-2-hydroxy-propyl)-2-hydroxy-acetamide;

N—((S)-3-{4-[5-(5-dimethylaminomethyl-4-methyl-thiophen-2-yl)-[1,3,4]oxadiazol-2-yl]-2-ethyl-6-methyl-phenoxy}-2-hydroxy-propyl)-2-hydroxy-acetamide;

N—((S)-3-{4-[5-(5-diethylaminomethyl-4-methyl-thiophen-2-yl)-[1,2,4]oxadiazol-3-yl]-2-methoxy-6-methyl-phenoxy}-2-hydroxy-propyl)-2-hydroxy-acetamide;

N—((S)-3-{2-chloro-4-[5-(5-diethylaminomethyl-4-methyl-thiophen-2-yl)-[1,2,4]oxadiazol-3-yl]-6-methyl-phenoxy}-2-hydroxy-propyl)-2-hydroxy-acetamide;

N—((S)-3-{4-[5-(5-diethylaminomethyl-4-methyl-thiophen-2-yl)-[1,2,4]oxadiazol-3-yl]-3-methyl-phenoxy}-2-hydroxy-propyl)-2-hydroxy-acetamide;

(S)-3-{2-chloro-4-[5-(5-diethylaminomethyl-4-methyl-thiophen-2-yl)-[1,2,4]oxadiazol-3-yl]-6-methyl-phenoxy}-propane-1,2-diol;

(S)-1-{4-[5-(5-diethylaminomethyl-4-methyl-thiophen-2-yl)-[1,2,4]oxadiazol-3-yl]-2-ethyl-6-methyl-phenoxy}-3-(2-hydroxy-ethylamino)-propan-2-ol;

3-((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propylamino)-propan-1-ol;

3-((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propylamino)-propane-1,2-diol;

2-((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propylamino)-propane-1,3-diol;

(S)-1-{4-[5-(5-diethylaminomethyl-4-methyl-thiophen-2-yl)-[1,2,4]oxadiazol-3-yl]-2-ethyl-6-methyl-phenoxy}-3-(2-methoxy-ethylamino)-propan-2-ol;

(S)-1-(2-amino-ethylamino)-3-{4-[5-(5-diethylaminomethyl-4-methyl-thiophen-2-yl)-[1,2,4]oxadiazol-3-yl]-2-ethyl-6-methyl-phenoxy}-propan-2-ol;

((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propylamino)-acetic acid;

[((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-methyl-amino]-acetic acid;

3-((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propylamino)-propionic acid;

N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-3-hydroxy-propionamide;

2-amino-N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-acetamide;

N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-2-methylamino-acetamide;

3-amino-N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-propionamide; and N—((S)-3-{4-[5-(5-diethylaminomethyl-4-methyl-thiophen-2-yl)-[1,2,4]oxadiazol-3-yl]-2-ethyl-6-methyl-phenoxy}-2-hydroxy-propyl)-3-methylamino-propionamide;

or a salt of such a compound.

14. A pharmaceutical composition comprising a compound according to claim 1, or a pharmaceutically acceptable salt thereof, and a pharmaceutically acceptable carrier.

15. A method for the treatment of diseases or disorders comprising administering to a patient in need an effective amount of the compound of claim 1 or a pharmaceutically acceptable salt thereof, wherein the diseases or disorders are selected from the group consisting of rejection of transplanted organs of kidney, liver, heart, lung, pancreas, cornea, and skin; and graft-versus-host diseases brought about by stem cell transplantation.

* * * * *

UNITED STATES PATENT AND TRADEMARK OFFICE
CERTIFICATE OF CORRECTION

PATENT NO. : 8,148,410 B2
APPLICATION NO. : 12/747280
DATED : April 3, 2012
INVENTOR(S) : Martin Bolli et al.

It is certified that error appears in the above-identified patent and that said Letters Patent is hereby corrected as shown below:

Column 83, line 1
"-$CH_2$-CH(OH)-CH-$CH_2$-$NR^{61}R^{62}$" should read "-$CH_2$-CH(OH)-$CH_2$-$NR^{61}R^{62}$"

Column 83, line 21
"2-($C_{1-14}$alkylamino)ethyl," should read "2-($C_{1-4}$alkylamino)ethyl,"

Column 84, line 60
"1-2-hydroxy-propyl)-2-hydroxy-acetamide;" should read
"}-2-hydroxy-propyl)-2-hydroxy-acetamide);"

Signed and Sealed this
Eleventh Day of September, 2012

David J. Kappos
*Director of the United States Patent and Trademark Office*